(12) United States Patent
Gall et al.

(10) Patent No.: US 9,598,456 B2
(45) Date of Patent: Mar. 21, 2017

(54) MODIFIED CYTOSINE POLYNUCLEOTIDE OLIGOMERS AND METHODS

(71) Applicant: CEPHEID, Sunnyvale, CA (US)

(72) Inventors: Alexander A. Gall, Woodinville, WA (US); Sergey G. Lokhov, Bothell, WA (US); Mikhail A. Podyminogin, Lake Forest Park, WA (US); Ekaterina V. Viazovkina, Lynnwood, WA (US); Kevin Patrick Lund, Lynnwood, WA (US)

(73) Assignee: Cepheid, Sunnyvale, CA (US)

( * ) Notice: Subject to any disclaimer, the term of this patent is extended or adjusted under 35 U.S.C. 154(b) by 99 days.

(21) Appl. No.: 14/673,494

(22) Filed: Mar. 30, 2015

(65) Prior Publication Data

US 2015/0275283 A1    Oct. 1, 2015

Related U.S. Application Data

(60) Provisional application No. 61/972,391, filed on Mar. 30, 2014.

(51) Int. Cl.
| | | |
|---|---|---|
| *C07H 19/04* | (2006.01) | |
| *C07H 21/04* | (2006.01) | |
| *C12Q 1/68* | (2006.01) | |
| *C07H 19/10* | (2006.01) | |
| *C12N 15/11* | (2006.01) | |
| *C07H 19/06* | (2006.01) | |
| *C07K 5/065* | (2006.01) | |

(52) U.S. Cl.
CPC ............ *C07H 19/10* (2013.01); *C07H 19/06* (2013.01); *C07K 5/06078* (2013.01); *C12N 15/11* (2013.01); *C12N 15/111* (2013.01); *C12Q 1/6827* (2013.01); *C12Q 1/6858* (2013.01); *C12N 2310/311* (2013.01); *C12N 2310/312* (2013.01); *C12N 2310/314* (2013.01); *C12N 2310/315* (2013.01); *C12N 2310/3125* (2013.01); *C12N 2310/3181* (2013.01); *C12N 2310/32* (2013.01); *C12N 2310/3231* (2013.01); *C12N 2310/334* (2013.01); *C12N 2310/3513* (2013.01); *C12N 2320/52* (2013.01)

(58) Field of Classification Search
CPC ..... C07H 19/073; C07H 21/04; C12Q 1/6813
USPC .................................. 536/4.1, 23.1; 435/6.1
See application file for complete search history.

(56) References Cited

FOREIGN PATENT DOCUMENTS

WO    WO 2007/127992 A2    11/2007

OTHER PUBLICATIONS

International Preliminary Report on Patentability received in International Application No. PCT/US2015/023428, dated Oct. 13, 2016.
International Search Report received in International Application No. PCT/US2015/023428, dated Jul. 10, 2015.
Written Opinion of the International Searching Authority received in International Application No. PCT/US2015/023428, dated Jul. 10, 2015.
Herdewijn, P: "Review Heterocyclic Modifications of Oligonucleotides and Antisense Technology", Antisense & Nucleic Acid Drug Development, vol. 10 (2000), pp. 297-310.
Latham, J. A. et al.: "The Application of a modified nucleotide in aptamer selection: novel thrombin aptamers containing 5-(1-pentynyl)-2'-deoxyuridine", Nucleic Acids Research, vol. 22, No. 14, (1994), pp. 2817-2822.
Roychowdhury, A. et al.: "2'-Deoxycytidines Carrying Amino and Thiol Functionality: Synthesis and Incorporation by Vent (EXO⁻) Polymerase", Organic Letters, American Chemical Society, vol. 6, No. 4, (2004), pp. 489-492.

*Primary Examiner* — Jezia Riley
(74) *Attorney, Agent, or Firm* — Duane Morris LLP; Siegfried J.W. Ruppert

(57) ABSTRACT

Disclosed are modified cytosine bases that provide enhanced base-pairing affinity for guanine bases in polynucleotide hybridization complexes. Also disclosed are polynucleotide oligomers, polynucleotide hybridization complexes that comprise such modified cytosine bases. Also disclosed are various methods of use. For example, in some embodiments, modified polynucleotide oligomers disclosed herein can be used as primers and probes for nucleic acid amplification and/or detection.

119 Claims, 3 Drawing Sheets

MODIFIED CYTOSINE POLYNUCLEOTIDE OLIGOMERS AND METHODS

CROSS REFERENCE TO RELATED APPLICATIONS

This application claims benefit of provisional patent application Ser. No. 61/972,391, filed Mar. 30, 2014, and entitled "MODIFIED CYTOSINE POLYNUCLEOTIDE OLIGOMERS AND METHODS, the disclosure of which is incorporated herein in its entirety by reference for all purposes.

FIELD OF THE INVENTION

The technology herein pertains to nucleic acids.

BACKGROUND OF THE INVENTION

Polynucleotides are useful in a variety of applications such as target detection, diagnostic applications, therapeutic applications, nucleic acid sequencing, forensic analysis, and target amplification, for example. Usually, such applications require polynucleotides that hybridize to complementary polynucleotide strands with high specificity and sensitivity, especially when a target nucleic acid is available in limited quantities.

Nucleotide analogs with modified bases have been developed for inclusion in polynucleotides to change the strength, sensitivity and/or specificity of nucleic acid hybridization, amplification, and/or detection. Nevertheless, new chemical structures and methods are needed to expand the set of tools available for manipulation and analysis of nucleic acids.

BRIEF SUMMARY OF THE INVENTION

The present invention provides, among other things, novel, non-naturally occurring cytosine-like modified bases (also referred to herein as "modified cytosine bases" or simply, "modified bases") that can provide enhanced base-pairing with guanine bases, polynucleotide oligomers comprising such modified bases and uses thereof.

The modified bases of the present invention when incorporated into polynucleotide oligomers have been discovered to surprisingly increase the binding affinity and specificity of those oligomers comprising them for hybridization with complementary sequences as compared to oligomers that do not contain such modified bases. This surprising finding permits the use of shorter oligomers or shorter regions of complementarity between an oligomer and its complementary target sequence. A further advantage of the modified cytosine bases of the invention is that they can enhance aqueous solubility of the oligomers that contain them. This can be especially useful to increase the solubility of polynucleic acid (PNA) oligomers, which are well known to be relatively water-insoluble compared to the solubility of DNA and RNA. The increased water solubility (in addition to increased strength of base-pairing affinity of cytosine for complementary bases such as guanine during hybridization) can also be useful to offset the hydrophobic character of aromatic fluorophores and quencher moieties, which can promote unwanted precipitation or aggregation of labeled polynucleotide oligomers in aqueous conditions. Furthermore, one or more modified bases of the invention may be located anywhere in an oligomer base sequence, depending on the particular needs of a user.

Polynucleotide oligomers of the present invention may comprise any number of modified bases. In some embodiments of the present invention, a polynucleotide oligomer comprises at least one modified base, wherein the modified base is represented by the formula:

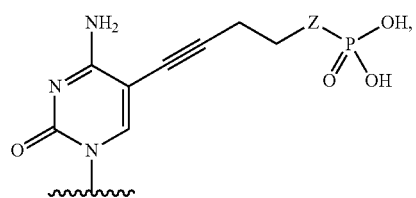

wherein Z is $CH_2$ or O. In a particular embodiment of the present invention, Z is O. A modified base as shown in the formula above, herein is referred to as "modified cytosine base" or simply, "modified base."

Polynucleotide oligomers of the present invention may comprise any number of deoxynucleotide moieties. In some embodiments, a polynucleotide oligomer comprises at least one deoxyribonucleotide moiety. In some embodiments, a modified cytosine base is covalently linked to the deoxyribonucleotide moiety in the polynucleotide oligomer.

Polynucleotide oligomers of the present invention may also comprise any number of peptide nucleic acid (PNA) moieties. In some embodiments, the polynucleotide oligomer comprises at least one peptide nucleic acid (PNA) moiety. In some embodiments, a modified cytosine base is covalently linked to the peptide nucleic acid moiety in the polynucleotide oligomer.

In some embodiments, a polynucleotide oligomer is a PNA/DNA chimera, wherein a modified cytosine base of the invention is included in a PNA segment or in a DNA segment of the chimera, or both a PNA segment and a DNA segment of the chimera each comprise such a modified base.

Polynucleotides of the present invention may comprise any number of modified bases. In some embodiments, a polynucleotide oligomer comprises a plurality of modified bases. In some embodiments, a polynucleotide oligomer comprises at least two modified bases. When a polynucleotide oligomer comprises a plurality of modified cytosine bases, the modified cytosine bases may be the same or different.

There is no limitation as to where within a polynucleotide oligomer a modified cytosine base can be incorporated. In some embodiments of the present invention, a polynucleotide oligomer comprises a modified cytosine base at the 3' end of the polynucleotide oligomer. In some embodiments, a polynucleotide oligomer comprises a modified cytosine base at one base from the 3' end of the polynucleotide oligomer.

A polynucleotide oligomer of the present invention may comprise one or more additional compounds. In some embodiments of the present invention, a polynucleotide oligomer comprises a minor groove binder. In some embodiments, a polynucleotide oligomer comprises an intercalator.

A preferred polynucleotide oligomer of the present invention is a polynucleotide oligomer wherein the backbone comprises 2'-deoxyribose or ribose. However, a polynucleotide oligomer of the present invention may comprise one or more modifications. In some embodiments, a polynucleotide oligomer comprises a sugar modification. Various sugar modifications are useful. Some non-limiting sugar modifications include arabinose, d-arabino-hexitol, 2-fluoroarabinose, xylulose, hexose, or a bicyclic sugar.

A polynucleotide oligomer of the present invention may comprise one or more backbone modifications. In some embodiments, the polynucleotide oligomer comprises a backbone modification. In some embodiments, a backbone modification is selected from the group consisting of a modified sugar phosphate backbone, a locked nucleic acid backbone, a peptidic backbone, a phosphotriester backbone, a phosphoramidate backbone, a siloxane backbone, a carboxymethylester backbone, an acetamidate backbone, a carbamate backbone, a thioether backbone, a bridged methylene phosphonate backbone, a phosphorothioate backbone, a methylphosphonate backbone, an alkylphosphonate backbone, a phosphate ester backbone, an alkylphosphonothioate backbone, a phosphorodithioate backbone, a carbonate backbone, a phosphate triester backbone, a carboxymethyl ester backbone, a methylphosphorothioate backbone, a phosphorodithioate backbone, a backbone having p-ethoxy linkages, and a combination of two or more of any of the foregoing. In a particular embodiment of the present invention, the backbone modification is a modified sugar phosphate backbone.

In some embodiments of the present invention, a polynucleotide oligomer comprises a 3'-terminal nucleotide that is extendable by a DNA or RNA dependent polymerase enzyme.

A polynucleotide oligomer of the present invention may comprise any useful number of nucleotides. In some embodiments, a polynucleotide oligomer comprises fewer than 30 nucleotides. In some embodiments, a polynucleotide oligomer comprises from about 9 to about 25 nucleotides, i.e. 9, 10, 11, 12, 13, 14, 15, 16, 17, 18, 19, 20, 21, 22, 23, 24 or 25 nucleotides.

A polynucleotide oligomer of the present invention may comprise one or more detectable labels. In some embodiments of the present invention, a polynucleotide oligomer comprises at least one detectable label. The detectable labels are not limited. In some embodiments, a detectable label is a fluorophore or a fluorescence quencher. In some embodiments, the polynucleotide oligomer comprises a fluorophore and a fluorescence quencher.

The present invention also provides methods using a modified cytosine base of the present invention in methods for hybridization. Any of the modified cytosine bases described herein may be used in a method for hybridization. In some embodiments of the present invention a method for hybridization of a polynucleotide oligomer of the present invention with a nucleic acid target sequence suspected of being present in a reaction mixture, is provided. In some embodiments, the method comprises the steps of incubating a reaction mixture comprising a polynucleotide oligomer and suspected of comprising a target nucleic acid sequence under conditions favorable for hybridization of the polynucleotide oligomer to the target nucleic acid sequence if present in the reaction mixture. The polynucleotide oligomer used in that method is complementary to a sequence within the nucleic acid target sequence suspected to be present in the reaction mixture and comprises at least one modified base represented by the formula:

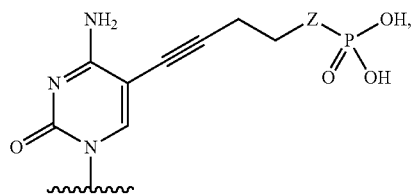

wherein Z is $CH_2$ or O. In a particular embodiment of the present invention, Z is O.

The reaction mixture is incubated, thereby forming a duplex between the polynucleotide oligomer and the target nucleic acid sequence if present in the reaction mixture. In some embodiments, the method comprises the step of detecting the presence or confirming the absence of the target nucleic acid sequence in the reaction mixture. The presence of the target nucleic acid sequence in the reaction mixture is detected as a result of the formation of such duplex. The absence of the target nucleic acid sequence in the reaction mixture is confirmed as a result of the non-formation of such duplex. In some embodiments of the method, the polynucleotide oligomer comprises a moiety selected from the group consisting of a detectable label, a fluorophore and a fluorescence quencher. A detectable label, fluorophore and/or fluorescence quencher facilitates detection of the duplex and/or of the target nucleic acid sequence.

The present invention also provides duplexes comprising any number of polynucleotide oligomers comprising a modified cytosine base of the present invention. In some embodiments of the present invention, a duplex comprises at least one polynucleotide oligomer and a polynucleotide sequence. The at least one polynucleotide oligomer comprises a modified cytosine base, and four or more contiguous bases that are complementary with and are hybridized to at least four contiguous bases of the complementary polynucleotide sequence. Such duplexes can be formed with any polynucleotide oligomer of the present invention. In some embodiments, the polynucleotide oligomer with the duplex comprises at least one modified base represented by the formula

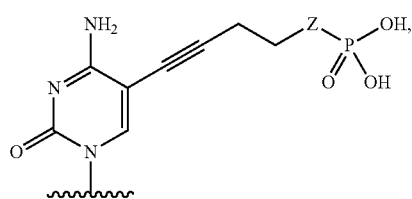

wherein Z is $CH_2$ or O. In a particular embodiment of the present invention, Z is O.

In some embodiments the polynucleotide oligomer within the duplex comprises a moiety selected from the group consisting of a detectable label, a fluorophore and a fluorescence quencher. A detectable label, fluorophore and/or fluorescence quencher facilitates detection of the duplex and/or of the polynucleotide sequence within the duplex.

In some embodiments of the present invention, a modified nucleoside phosphoramidite is provided. In some embodiments of the present invention, the modified nucleoside phosphoramidite represented by the formula:

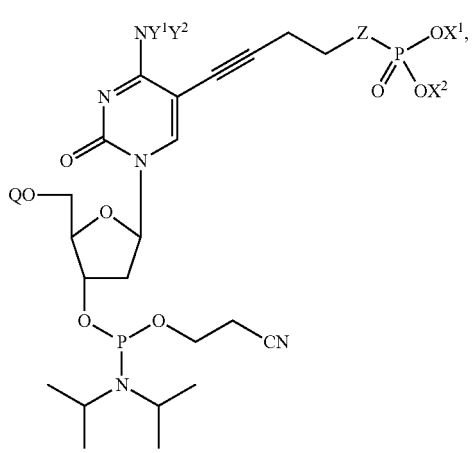

wherein Z is CH$_2$ or O; wherein X$^1$ and X$^2$ taken separately are protecting groups that are the same or different, or X$^1$ and X$^2$ taken together are a bidentate protecting group; wherein Y$^1$ and Y$^2$ are independently H or nitrogen protecting group, or Y$^1$ and Y$^2$ together are nitrogen protecting group; and wherein Q is a hydroxyl protecting group. In a particular embodiment of the present invention, Z is O.

In some embodiments of the present invention, a modified peptide nucleic acid monomer is provided. In some embodiments of the present invention, the modified peptide nucleic acid monomers represented by the formula:

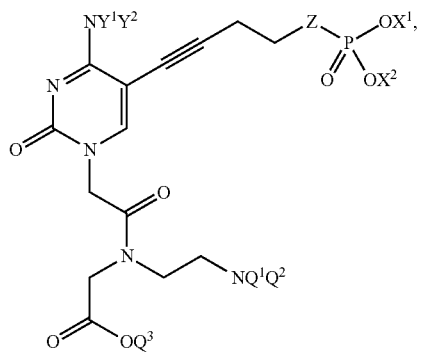

wherein Z is CH$_2$ or O; wherein X$^1$ and X$^2$ taken separately are protecting groups that are the same or different, or X$^1$ and X$^2$ taken together are a bidentate protecting group; wherein Y$^1$ and Y$^2$ are independently H or nitrogen protecting group, or Y$^1$ and Y$^2$ together are nitrogen protecting group; wherein Q$^1$ and Q$^2$ are independently H or nitrogen protecting group, or Q$^1$ and Q$^2$ together are nitrogen protecting group; and wherein Q$^3$ is H or a carboxyl protecting group.

In some embodiments of the present invention, a modified cytosine nucleoside is provided. In some embodiments of the present invention, the modified cytosine nucleoside is represented by the formula:

or

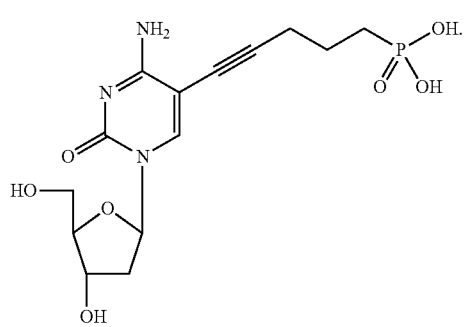

In a particular embodiment of the present invention, the modified cytosine nucleoside is represented by the formula:

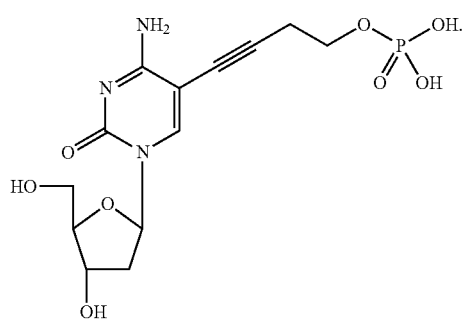 [SMILES: Nc1nc(=O)n(C2CC(O)C(CO)O2)cc1C#CCCOP(=O)(O)O]

In some embodiments of the present invention, a modified cytosine nucleotide 5'-triphosphate is provided. In some embodiments of the present invention, the modified cytosine nucleotide 5'-triphosphate represented by the formula:

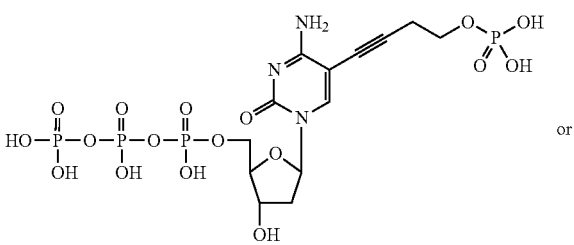

or

-continued

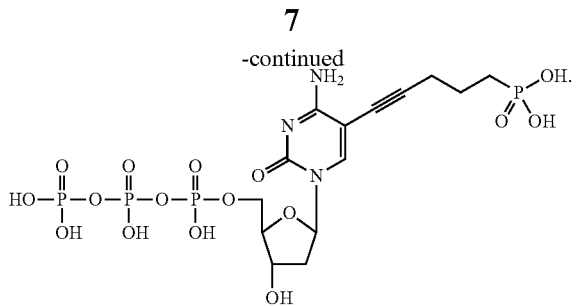

In a particular embodiment of the present invention, the modified cytosine nucleotide 5'-triphosphate is represented by the formula:

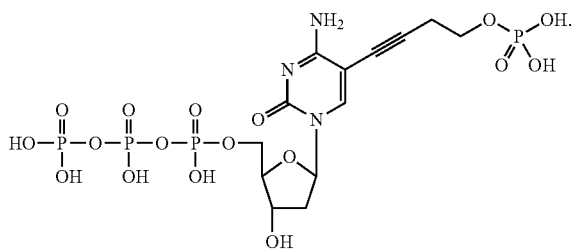 [SMILES: Nc1nc(=O)n(C2CC(O)C(COP(=O)(O)OP(=O)(O)OP(=O)(O)O)O2)cc1C#CCCOP(=O)(O)O]

Some embodiments of the present invention are set forth directly below:

Embodiment 1. A polynucleotide oligomer comprising at least one modified base, wherein the at least one modified base is represented by the formula:

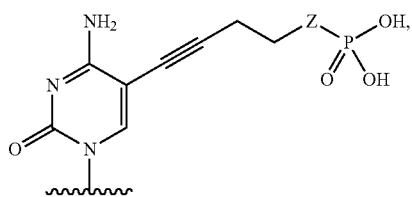

wherein Z is $CH_2$ or O, and preferably, Z is O.

Embodiment 2. The polynucleotide oligomer according to embodiment 1, wherein the polynucleotide oligomer comprises a plurality of deoxyribonucleotide moieties, preferably, at least one deoxyribonucleotide moiety.

Embodiment 3. The polynucleotide oligomer according to embodiment 2, wherein the modified base is covalently linked to the at least one deoxyribonucleotide moiety.

Embodiment 4. The polynucleotide oligomer according to any one of embodiments 1-3, wherein the polynucleotide oligomer comprises a plurality of peptide nucleic acid moieties, preferably, at least one peptide nucleic acid moiety.

Embodiment 5. The polynucleotide oligomer of embodiment 4, wherein the modified base is covalently linked to the at least one peptide nucleic acid moiety.

Embodiment 6. The polynucleotide oligomer according to any one of embodiments 1-5, wherein the polynucleotide oligomer is a PNA/DNA chimera.

Embodiment 7. The polynucleotide oligomer according to any one of embodiments 1-6, wherein the polynucleotide oligomer comprises at least two modified bases and wherein Z in the at least two modified bases is the same or different.

Embodiment 8. The polynucleotide oligomer according to any one of embodiments 1-7, wherein the polynucleotide oligomer comprises the modified base at its 3' end or at one base from its 3' end.

Embodiment 9. The polynucleotide oligomer according to any one of embodiments 1-8, wherein the polynucleotide oligomer further comprises a minor groove binder or an intercalator.

Embodiment 10. The polynucleotide oligomer according to any one of embodiments 1-9, wherein the polynucleotide oligomer further comprises a sugar modification; preferably, the sugar the sugar modification is selected from the group consisting of arabinose, d-arabino-hexitol, 2-fluoroarabinose, xylulose, hexose, and a bicyclic sugar.

Embodiment 11. The polynucleotide oligomer according to any one of embodiments 1-10, wherein the polynucleotide oligomer further comprises a backbone modification, preferably, the backbone modification is selected from the group consisting of a modified sugar phosphate backbone, a locked nucleic acid backbone, a peptidic backbone, a phosphotriester backbone, a phosphoramidate backbone, a siloxane backbone, a carboxymethylester backbone, an acetamidate backbone, a carbamate backbone, a thioether backbone, a bridged methylene phosphonate backbone, a phosphorothioate backbone, a methylphosphonate backbone, an alkylphosphonate backbone, a phosphate ester backbone, an alkylphosphonothioate backbone, a phosphorodithioate backbone, a carbonate backbone, a phosphate triester backbone, a carboxymethyl ester backbone, a methylphosphorothioate backbone, a phosphorodithioate backbone, a backbone having p-ethoxy linkages, and a combinations of two or more of any of the foregoing, preferably, the backbone modification is a modified sugar phosphate backbone.

Embodiment 12. The polynucleotide oligomer according to any of embodiments 1-11, wherein the polynucleotide oligomer further comprises a 3'-terminal nucleotide that is extendable by a DNA or RNA dependent polymerase enzyme.

Embodiment 13. The polynucleotide oligomer according to any one of embodiments 1-2 wherein the polynucleotide oligomer comprises fewer than 30 nucleotides, preferably, the oligonucleotide oligomer comprises from about 9 to about 25 nucleotides.

Embodiment 14. The polynucleotide oligomer according to any one of embodiments 1-13, wherein the polynucleotide oligomer further comprises a moiety selected from the group consisting of a detectable label, a fluorophore, and a fluorescence quencher.

Embodiment 15. A method for hybridization of a polynucleotide oligomer according to any one of embodiments 1-14 with a nucleic acid target sequence suspected of being present in a reaction mixture, the method comprising the steps of:

(a) incubating a reaction mixture comprising a polynucleotide oligomer according to any one of embodiments 1-14 and suspected of comprising a target nucleic acid sequence under conditions favorable for hybridization of the polynucleotide oligomer to the target nucleic acid sequence if present in the reaction mixture; and (b) detecting the presence or confirming the absence of the target nucleic acid sequence in the reaction mixture;

wherein the polynucleotide oligomer is complementary to a sequence within the nucleic acid target sequence, wherein the polynucleotide oligomer comprises at least one modified base, and wherein the at least one modified base is represented by the formula:

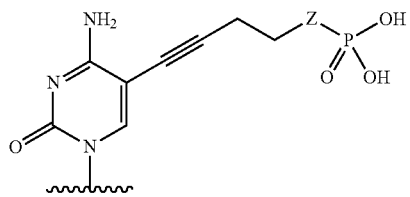

wherein Z is CH$_2$ or O, and preferably, Z is O.

Embodiment 16. The method according to embodiment 15, wherein the polynucleotide oligomer further comprises a moiety selected from the group consisting of a detectable label, a fluorophore, and a fluorescence quencher.

Embodiment 17. A duplex comprising:
(i) at least one polynucleotide oligomer according to any one of embodiments 1-14; and
(ii) a polynucleotide sequence;
wherein the at least one polynucleotide oligomer according to any one of embodiments 1-14 comprises four or more contiguous bases that are complementary with and hybridized to at least four contiguous bases of the polynucleotide sequence.

Embodiment 18. A modified nucleoside phosphoramidite represented by the formula:

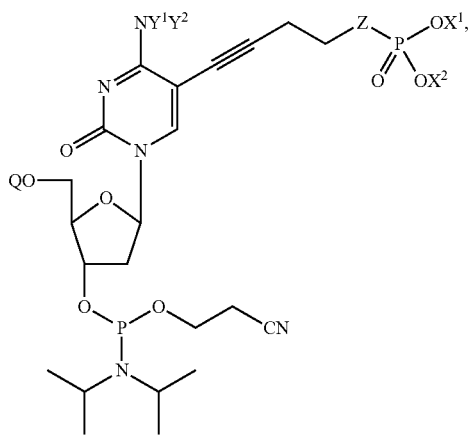

wherein Z is CH$_2$ or O, and preferably, Z is O;
wherein X$^1$ and X$^2$ taken separately are protecting groups that are the same or different, or X$^1$ and X$^2$ taken together are a bidentate protecting group;
wherein and Y$^2$ are independently H or nitrogen protecting group, or Y$^1$ and Y$^2$ together are nitrogen protecting group; and
wherein Q is a hydroxyl protecting group.

Embodiment 19. A modified peptide nucleic acid monomer represented by the formula:

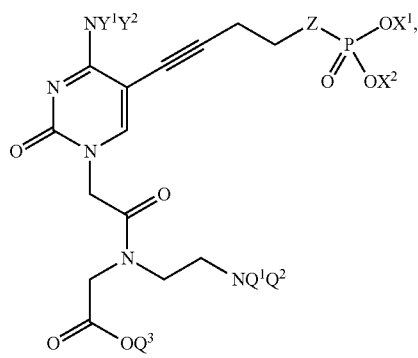

wherein Z is CH$_2$ or O, and preferably, Z is O;
wherein X$^1$ and X$^2$ taken separately are protecting groups that are the same or different, or X$^1$ and X$^2$ taken together are a bidentate protecting group;
wherein and Y$^2$ are independently H or nitrogen protecting group, or Y$^1$ and Y$^2$ together are nitrogen protecting group;
wherein and Q$^2$ are independently H or nitrogen protecting group, or Q$^1$ and Q$^2$ together are nitrogen protecting group; and
wherein Q$^3$ is H or a carboxyl protecting group.

Embodiment 20. A modified thymidine nucleoside represented by the formula:

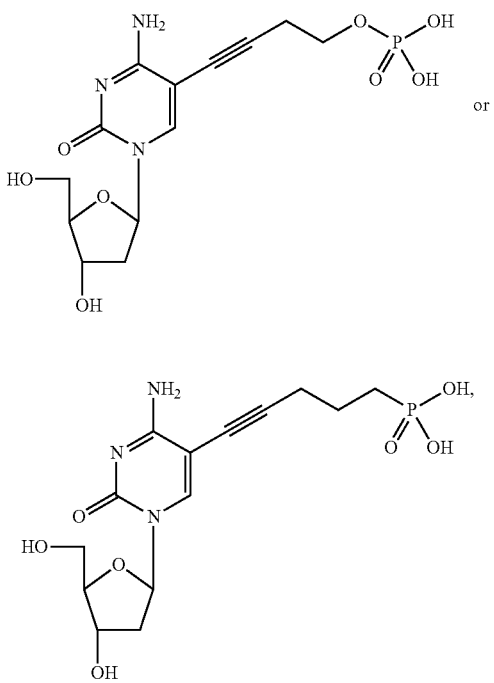 [SMILES: Nc1nc(=O)n(C2CC(O)C(CO)O2)cc1C#CCCOP(=O)(O)O ; Nc1nc(=O)n(C2CC(O)C(CO)O2)cc1C#CCCCP(=O)(O)O]

and preferably, the modified cytosine nucleoside is represented by the formula:

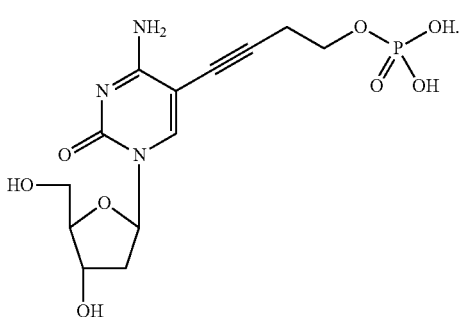 [SMILES: Nc1nc(=O)n(C2CC(O)C(CO)O2)cc1C#CCCOP(=O)(O)O]

Embodiment 21. A modified cytosine nucleotide 5'-triphosphate represented by the formula:

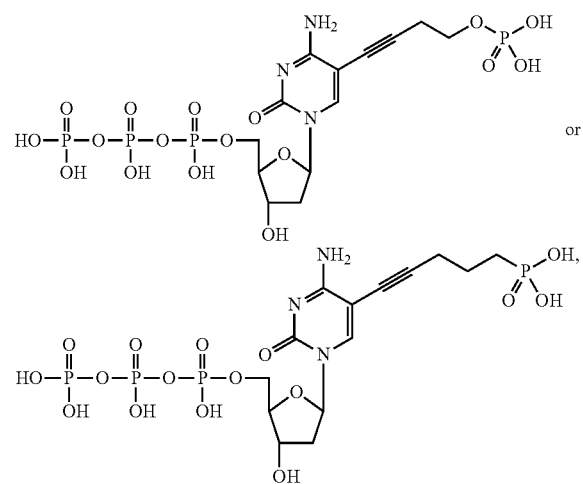

and preferably, the modified cytosine nucleotide 5'-triphosphate represented by the formula:

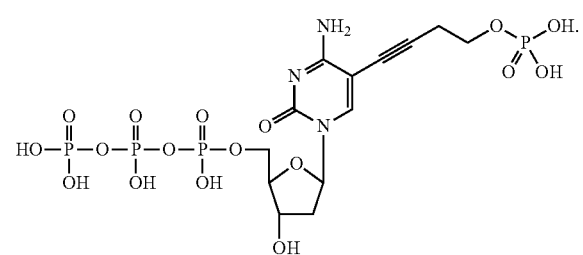 [SMILES: Nc1nc(=O)n(C2CC(O)C(COP(=O)(O)OP(=O)(O)OP(=O)(O)O)O2)cc1C#CCCOP(=O)(O)O]

Additional features and advantages of the present invention are set forth in the description which follows. These and other features of the disclosure will become more fully apparent from the following description or can be learned by the practice of the principles set forth herein.

BRIEF DESCRIPTION OF THE DRAWINGS

FIG. 4B: 8, 10, 13, 16, 20, 30 and 45 seconds). Additional details are provided in Example 7 and in Table 4.

DETAILED DESCRIPTION OF THE INVENTION

I. Definitions

Figure 1:
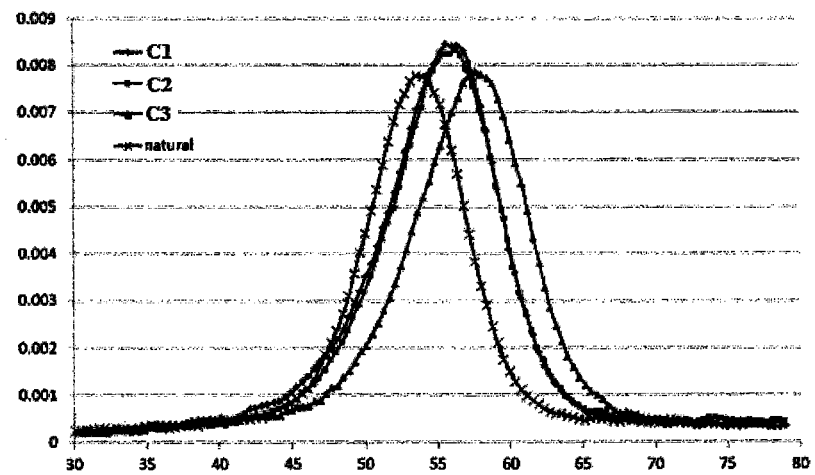
FIG. 1 schematically depicts melting curves (plotted as the first derivative of absorbance at 270 nm (A270) versus temperature (° C.) obtained from a series of same-sequence polynucleotide oligomers 18-mers comprising one modified base (C1 or C2) or two modified bases (C3) of the invention ("$C^{BP}$") at various positions within the polynucleotide oligomer, or comprising a normal C base (designated "natural"), hybridized to a complementary DNA polynucleotide 12-mer. The figure shows that the modified cytosine oligomers of the present invention have significantly stronger hybridization affinities for the complementary sequence than does the natural, same-sequence DNA oligomer, and that the oligomer comprising two $C^{BP}$ moieties (C2) had the highest affinity. Additional details are provided in Example 5 and Table 4.

Throughout the present specification and the accompanying claims the words "comprise" and "include" and variations thereof such as "comprises," "comprising," "includes," and "including" are to be interpreted inclusively. That is, these words are intended to convey the possible inclusion of other elements or integers not specifically recited, where the context allows. No language in the specification should be construed as indicating any non-claimed element essential to the practice of the invention. As used herein, the term "consisting of" is intended to mean including and limited to whatever follows the phrase "consisting of". Thus the phrase "consisting of" indicates that the listed elements are required or mandatory and that no other elements may be present. The term "consisting essentially of" means that the composition, method or structure may include additional ingredients, steps and/or parts, but only if the additional ingredients, steps and/or parts do not materially alter the basic and novel characteristics of the claimed composition, method or structure.

The terms "a" and "an" and "the" and similar referents used in the context of describing the invention (especially in the context of the following claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, each individual value is incorporated into the specification as if it were individually recited herein. Ranges may be expressed herein as from "about" (or "approximate") one particular value, and/or to "about" (or "approximate") another particular value. When such a range is expressed, another embodiment includes from the one particular value and/or to the other particular value. Similarly, when values are expressed as approximations, by use of the antecedent "about" or "approximate" it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that is "less than or equal to the value" or "greater than or equal to the value" possible ranges between these values are also disclosed, as appropriately understood by the skilled artisan. For example, if the value "10" is disclosed the "less than or equal to 10" as well as "greater than or equal to 10" is also disclosed.

All methods described herein can be performed in any suitable order unless otherwise indicated herein or otherwise clearly contradicted by context. Further, all methods described herein and having more than one step can be performed by more than one person or entity. Thus, a person or an entity can perform step (a) of a method, another person or another entity can perform step (b) of the method, and a yet another person or a yet another entity can perform step (c) of the method, etc. The use of any and all examples, or exemplary language (e.g. "such as") provided herein is intended merely to better illuminate the invention and does not pose a limitation on the scope of the invention otherwise claimed.

Units, prefixes, and symbols are denoted in their Système International de Unites (SI) accepted form. Unless otherwise indicated, nucleic acids are written left to right in 5' to 3' orientation; amino acid sequences are written left to right in amino to carboxy orientation.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

The headings used herein are for organizational purposes only and are not meant to be used to limit the scope of the description or the claims, which can be had by reference to the specification as a whole. Accordingly, the terms defined immediately below are more fully defined by reference to the specification in its entirety.

Illustrations are for the purpose of describing a preferred embodiment of the invention and are not intended to limit the invention thereto.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); The Cambridge Dictionary of Science and Technology (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

As used herein, the term "about" refers to a range of values of plus or minus 10% of a specified value. For example, the phrase "about 200" includes plus or minus 10% of 200, or from 180 to 220, unless clearly contradicted by context.

As used herein, the term "amplification" refers to any means by which at least a partial sequence of at least one target nucleic acid or its sequence complement is produced, typically in a template-dependent manner, including without limitation, a broad range of techniques for amplifying nucleic acid sequences, either linearly or exponentially. Non-limiting exemplary amplification methods include polymerase chain reaction (PCR), reverse-transcriptase PCR, real-time PCR, nested PCR, multiplex PCR, quantitative PCR (Q-PCR), nucleic acid sequence based amplification (NASBA), transcription mediated amplification (TMA), ligase chain reaction (LCR), rolling circle amplification (RCA), strand displacement amplification (SDA), ligase detection reaction (LDR), multiplex ligation-dependent probe amplification (MLPA), ligation followed by Q-replicase amplification, primer extension, strand displacement amplification (SDA), hyperbranched strand displacement amplification, multiple displacement amplification (MDA), nucleic acid strand-based amplification (NASBA), two-step multiplexed amplifications, digital amplification, and the like. Descriptions of such techniques can be found in, among other sources, Ausubel et al.; *PCR Primer: A Laboratory Manual*, Diffenbach, Ed., Cold Spring Harbor Press (1995); *The Electronic Protocol Book*, Chang Bioscience (2002); *The Nucleic Acid Protocols Handbook*, R. Rapley, ed., Humana Press, Totowa, N.J. (2002); and Innis et al, *PCR Protocols: A Guide to Methods and Applications*, Academic Press (1990).

As used herein, the terms "amplification condition" or "extension condition," which are used interchangeably herein refer to conditions under which a polymerase can add one or more nucleotides to the 3' end of a polynucleotide. Such amplification or extension conditions are well known in the art, and are described, for example, in Sambrook and Russell, *Molecular Cloning: A Laboratory Manual*, 3rd Edition, 2001, Cold Spring Harbor Laboratory Press and Ausubel, et al, *Current Protocols in Molecular Biology*, 1987-2007, John Wiley & Sons.

As used herein, the term "array" or "microarray" in general refers to an ordered arrangement of hybridizable array elements such as polynucleotide probes on a substrate. An "array" is typically a spatially or logically organized collection, e.g., of oligonucleotide sequences or nucleotide sequence products such as RNA or proteins encoded by an oligonucleotide sequence. The array element may be an oligonucleotide, a DNA fragment, a polynucleotide, or the like. The array element may include any element immobilized on a solid support that is capable of binding with specificity to a target sequence such that gene expression may be determined, either qualitatively or quantitatively.

High-density oligonucleotide arrays are particularly useful for determining gene expression profiles for a large number of RNAs in a sample. Array elements can be prepared either synthetically or biosynthetically. Array elements can be identical or different from each other. The array can assume a variety of formats, e.g., libraries of soluble molecules; libraries of compounds tethered to resin beads, silica chips, or other solid supports. The array could either be a macroarray or a microarray, depending on the size of the sample spots on the array. A macroarray generally contains sample spot sizes of about 300 microns or larger and can be easily imaged by gel and blot scanners. A microarray would generally contain spot sizes of less than 300 microns. A multiple-well array is a support that includes multiple chambers for containing sample spots. A preferred array element is a modified polynucleotide oligomer of the present invention. Preferred molecules on an array are modified polynucleotide oligomers of the present invention. In some embodiments, modified polynucleotide oligomers of the present invention are attached to an array.

As used herein, the terms "attach to" or "attached to" or grammatical equivalents thereof mean to fasten on, fasten together, affix to, mount to, mount on, connect to or to join. "Attachment" means the act of attaching or the condition of being attached. Attachment can be direct or indirectly. For example a part A may be attached directly to part B. Alternatively, part A may be attached indirectly to part B through first attaching part A to part C and then attaching part C to part B. More than one intermediary part can be used to attach part A to part B. Attaching can be permanent, temporarily, or for a prolonged time. For example, a modified polynucleotide oligomer of the present invention may be attached to a solid support or array temporarily for the time necessary to perform a method of the invention or a step of a method of the invention. Alternatively, a modified polynucleotide oligomer of the present invention may be attached to a solid support or array for a prolonged time, e.g., also when a method of the present invention or a step of the method of the present invention is not performed. Also, a modified polynucleotide oligomer of the present invention may be attached permanently to a solid support or array.

As used herein, the term "base" means a nitrogen-containing heterocyclic moiety capable of forming Watson-Crick type hydrogen bonds with a complementary nucleotide base or nucleotide base analog, e.g. a purine, a 7-deazapurine, or a pyrimidine. Typical bases are the naturally occurring bases adenine, cytosine, guanine, thymine, and uracil. Bases also include analogs of naturally occurring bases such as deazaadenine, 7-deaza-8-azaadenine, 7-deazaguanine, 7-deaza-8-azaguanine, inosine, nebularine, nitropyrrole, nitroindole, 2-amino-purine, 2,6-diamino-purine, hypoxanthine, 5-methylcytosine, isocytosine, pseudoisocytosine, 5-bromouracil, 5-propynyluracil, 6-aminopurine, 2-chloro-6-aminopurine, xanthine, hypoxanthine, etc.

As used herein, the term "bead" means "a small mass with some rounded aspect or surface, such as a spherical, cylindrical, elliptical, oval, or dome-shaped mass.

As used herein, the term "biological fluid" refers to a fluid from a host and includes whole blood, serum, plasma, urine, tears, mucus ascites fluid, oral fluid, semen, stool, sputum, cerebrospinal fluid and fetal fluid. A biological fluid may include cells or be devoid of cells.

As used herein, the term "biological sample" means a sample of biological tissue or biological fluid that contains nucleic acids or polypeptides. Such samples are typically from humans, but include tissues isolated from non-human primates, or rodents, e.g., mice, and rats. Biological samples may also include sections of tissues such as surgical biopsy, fine needle aspiration biopsy and autopsy samples, frozen sections taken for histological purposes, blood, plasma, serum, sputum, stool, tears, mucus, hair, skin, etc. Biological samples also include explants and primary and/or transformed cell cultures derived from patient tissues. A "biological sample" also refers to a cell or population of cells or a quantity of tissue or fluid from an animal. Most often, the biological sample has been removed from an animal, but the term "biological sample" can also refer to cells or tissue analyzed in vivo, i.e., without removal from the animal. Typically, a "biological sample" will contain cells from the animal, but the term can also refer to non-cellular biological material, such as non-cellular fractions of blood, saliva, or urine, that can be used to measure expression level of a polynucleotide or polypeptide. Numerous types of biological samples can be used in the present invention, including, but not limited to, a tissue biopsy or a blood sample. As used herein, a "tissue biopsy" refers to an amount of tissue removed from an animal, preferably a mammal, more preferable a primate, and most preferably a human. A "biological sample" encompasses samples that have been manipulated in any way after their procurement, such as by treatment with reagents, washed, treated to produce a nucleic acid sample (a sample comprising nucleic acid suitable for further manipulations), or enrichment for certain cell populations, such as $CD4^+$ T lymphocytes, glial cells, macrophages, tumor cells, peripheral blood mononuclear cells (PBMC), and the like. The term "biological sample" encompasses a clinical sample, and also includes cells in culture, cell supernatants, tissue samples, organs, bone marrow, and the like. As used herein, "providing a biological sample" means to obtain a biological sample for use in methods described in this invention. Most often, this will be done by removing a sample of cells from a subject, but can also be accomplished by using previously isolated cells (e.g., isolated by another person, at another time, and/or for another purpose), or by performing the methods of the invention in vivo. Archival tissues, having treatment or outcome history, will be particularly useful. A biological sample can also be derived from an animal which harbors a xenograft tumor implanted from a patient, another animal or a cancer cell line.

As used herein, the term "complementary" refers to the ability of oligomer sequences to hybridize to and form base pairs with one another. Base pairs are typically formed by hydrogen bonds between nucleotide units in antiparallel polynucleotide (oligomer) strands. Complementary polynucleotide oligomer strands can base pair in the Watson-Crick manner (e.g., A to T, A to U, C to G), or in any other manner that allows for the formation of duplexes. The percentage of "complementarity" of a probe sequence to a target sequence is the percentage "identity" of the probe sequence to the sequence of the target or to the complement of the sequence of the target. In determining the degree of "complementarity" between a probe and a target sequence, the degree of "complementarity" is expressed as the percentage identity between the sequence of the probe and the sequence of the target sequence or the complement of the sequence of the target sequence that best aligns therewith. An exemplary probe is an oligonucleotide oligomer as described herein.

As used herein, the term "different" means not the same, not of the same identity.

As used herein, the term "duplex" refers to a double-stranded hybridization complex formed by annealing (hybridizing) complementary (or partially complementary) single-stranded polynucleotides oligomers, e.g., DNA, RNA, or PNA.

The terms "hybridize" or "hybridization" are used herein with reference to "specific hybridization" which is the binding, duplexing, or annealing of a nucleic acid molecule preferentially to a particular nucleotide sequence, in some embodiments, under stringent conditions. The term "stringent conditions" refers to conditions under which a probe will hybridize preferentially to its target sequence, and to a lesser extent to, or not at all to, other sequences. "Stringent hybridization" and "stringent hybridization wash conditions" in the context of nucleic acid hybridization are sequence-dependent and are different under different environmental parameters. An extensive guide to the hybridization of nucleic acids is found in, e.g., Tijssen (1993) *Laboratory Techniques in Biochemistry and Molecular Biology-Hybridization with Nucleic Acid Probes part I*, Ch. 2, "Overview of principles of hybridization and the strategy of nucleic acid probe assays," Elsevier, NY. Generally, highly stringent hybridization and wash conditions for filter hybridizations are selected to be about 5° C. lower than the thermal melting point, also referred to as "thermal melting temperature" or "$T_m$," for the specific sequence at a defined ionic strength and pH. The dependency of hybridization stringency on buffer composition, temperature, and probe length are well known to those of skill in the art (see, e.g., Sambrook and Russell (2001) *Molecular Cloning: A Laboratory Manual* (3rd ed.) Vol. 1-3, Cold Spring Harbor Laboratory, Cold Spring Harbor Press, NY). The degree of hybridization of an oligomer (or polynucleotide oligomer) to a target sequence, also known as hybridization strength, is determined by methods that are well-known in the art. A preferred method is to determine the $T_m$ of a given hybrid duplex. This can be accomplished by subjecting a formed duplex in solution to gradually increasing temperature and monitoring the denaturation of the duplex, for example, by absorbance of ultraviolet light, which increases with the unstacking of base pairs that accompanies denaturation. $T_m$ is generally defined as the temperature at which half of the DNA strands are in the single-stranded (ssDNA) state. $T_m$ depends on various parameters such as the length of the hybridized complementary strand sequence, their specific nucleotide sequences, base compositions, and the concentrations of the complementary strands.

As used here, the term "label" or "detectable label" refer to a moiety that, when attached to a biomolecule, a nucleoside, a nucleotide, or a polynucleotide oligomer, renders such biomolecule, nucleoside, nucleotide, or polynucleotide oligomer detectable by suitable detection means. Exemplary labels include fluorophores, chromophores, radioisotopes, spin-labels, enzyme labels, chemiluminescent labels, electrochemiluminescent compounds, magnetic labels, microspheres, colloidal metal, immunologic labels, ligands, enzymes, and the like. In some embodiments, the labels are fluorescent dyes such as fluorescein-type or rhodamine-type dyes. In some embodiments, a label is selected from the group consisting of a radiolabel, an enzyme such as horseradish peroxidase or alkaline phosphatase, streptavidin, biotin, an epitope recognized by an antibody, and equivalents thereof.

"Mismatched nucleotide" is used herein with reference to a nucleotide in a sequence of interest that is not complementary to the corresponding nucleotide in a corresponding sequence when the sequence of interest and the target sequence are hybridized, e.g., in an amplification reaction. The complement of C is G and the complement of A is T. In other words, a "C" in a sequence of interest is considered to be mismatched with a "T", "C" or "A" in a target sequence.

As used herein, the terms "modified nucleotide base" or "modified base" refer to a base that does not have the structure of a naturally occurring base and thus, is non-naturally occurring. A preferred modified base disclosed herein, for example, is a modified cytosine base.

As used herein, the terms "modified polynucleotide oligomer" "modified oligonucleotide oligomer," and "modified oligomer" refer to a polynucleotide oligomer of the invention comprising at least one modified base. A preferred modified base disclosed herein, for example, is a modified cytosine base. The terms "modified polynucleotide oligomer," "modified oligonucleotide oligomer," and "modified oligomer," which are considered to be interchangeable as used herein, also refer to linear polymers of non-naturally occurring modified forms of a polynucleotide oligomer, an oligonucleotide oligomer, or an oligomer, including for example, double- and single-stranded deoxyribonucleotides, ribonucleotides, alpha-anomeric forms thereof, and the like. A preferred modified polynucleotide oligomer of the present invention is one that comprises a modified cytosine base. A modified polynucleotide oligomer may be composed entirely of deoxyribonucleotides, ribonucleotides, or analogs thereof, or may contain blocks or mixtures of two or more different monomer types. These terms also encompass sequences that include any of the known base analogs of DNA and RNA, also referred to as "oligonucleotide analogs" or "nucleic acid analogs." A variety of references disclose such nucleic acid analogs, including, for example, phosphoramidate (Beaucage et al., *Tetrahedron* 49(10):1925 (1993) and references therein; Letsinger, *J. Org. Chem.* 35:3800 (1970); Sprinzl et al., *Eur. J. Biochem.* 81:579 (1977); Letsinger et al., *Nucl. Acids Res.* 14:3487 (1986); Sawai et al., *Chem. Lett.* 805 (1984), Letsinger et al., *J. Am. Chem. Soc.* 110:4470 (1988); and Pauwels et al., *Chemica Scripta* 26:141 91986)), phosphorothioate (Mag et al., *Nucleic Acids Res.* 19:1437 (1991); and U.S. Pat. No. 5,644,048), phosphorodithioate (Briu et al., *J. Am. Chem. Soc.* 111:2321(1989), 0 methylphophoroamidite linkages (see, Eckstein, *Oligonucleotides and Analogues: A Practical Approach*, Oxford University Press), and peptide nucleic acid backbones and linkages (see, Egholm, *J. Am. Chem. Soc.* 114:1895 (1992); Meier et al., *Chem. Int. Ed. Engl.* 31:1008 (1992); Nielsen, *Nature* 365:566 (1993); Carlsson et al., *Nature* 380:207 (1996), all of which are incorporated by reference). Other analog nucleic acids include those with positive backbones (Denpcy et al., *Proc. Natl. Acad. Sci. USA* 92:6097 (1995); non-ionic backbones (U.S. Pat. Nos. 5,386,023, 5,637,684, 5,602,240, 5,216,141 and 4,469,863; Kiedrowski et al., *Angew. Chem. Intl. Ed. English* 30:423 (1991); Letsinger et al., *J. Am. Chem. Soc.* 110:4470 (1988); Letsinger et al., *Nucleoside & Nucleotide* 13:1597 (1994); Chapters 2 and 3, ASC Symposium Series 580, "*Carbohydrate Modifications in Antisense Research*", Ed. Y. S. Sanghui and P. Dan Cook; Mesmaeker et al., *Bioorganic & Medicinal Chem. Lett.* 4:395 (1994); Jeffs et al., *J. Biomolecular NMR* 34:17 (1994); *Tetrahedron Lett.* 37:743 (1996)) and non-ribose backbones, including those described in U.S. Pat. Nos. 5,235,033 and 5,034,506, and Chapters 6 and 7, ASC Symposium Series 580, "*Carbohydrate Modifications in Antisense Research*", Ed. Y. S. Sanghui and P. Dan Cook. Nucleic acids containing one or more carbocyclic sugars are also included within one definition of nucleic acids (see, Jenkins et al., *Chem. Soc. Rev. pp* 169 176 (1995)). Several nucleic acid analogs are described in Rawls, C & E News Jun. 2, 1997 page 35. All of these references are hereby expressly incorporated by reference.

As used herein, the term "naturally-occurring" in the context of nucleic acid molecules refers to an RNA or DNA molecule (single-stranded or double-stranded) having a nucleotide sequence that occurs in nature and comprising only components, such as bases, nucleosides and nucleotides that occur in nature.

As used herein, the term "nucleoside" refers to a molecule consisting of a nitrogenous base of the type mentioned herein that is bound to a ribose or deoxyribose sugar via a beta-glycosidic linkage. Examples of nucleosides include adenosine, cytidine, guanosine, thymidine, uridine and inosine. Typically, when the base is A or G, the ribose sugar is attached to the $N^9$-position of the base. When the base is C, T or U, the ribose sugar is attached to the $N^1$-position of the base (Kornberg and Baker, *DNA Replication*, 2nd Ed., Freeman, San Francisco, Calif., (1992)).

As used herein, the term "nucleotide" means a phosphate ester of a nucleoside, either as an independent monomer or as a subunit within a polynucleotide. Nucleotide monomers include for example nucleotide 5'-monophosphate, 5'-diphosphate, 5'-triphosphate, and 3'-monophosphate. Nucleotide triphosphates are sometimes denoted as "NTP", "dNTP" (2'-deoxypentose) or "ddNTP" (2',3'-dideoxypentose) to particularly point out the structural features of the ribose sugar. "Nucleotide 5'-triphosphate" refers to a nucleotide with a triphosphate ester group at the 5' position. The triphosphate ester group may include sulfur substitutions for one or more phosphate oxygen atoms, e.g. alpha-thionucleotide 5'-triphosphates. A nucleotide monophosphate, diphosphate or triphosphate may serve as the substrate for a nucleic acid processing enzyme that catalyzes modifications of nucleic acids or nucleic acid intermediates.

As used herein, the term "nucleotide processing enzyme" refers to an enzyme modifying or processing a nucleotide, an oligonucleotide or a nucleic acid and includes, but is not limited to, a primer extension enzyme, a DNA polymerase, an RNA polymerase, a restriction enzyme, a nicking enzyme, a repair enzyme and a ligation enzyme.

As used herein, the term "plurality" means more than one. For example, a plurality of modified polynucleotide oligomers means at least two modified polynucleotide oligomers, at least three modified polynucleotide oligomers, or at least four modified polynucleotide oligomers, and the like. If an embodiment of the present invention comprises more than one modified polynucleotide oligomers, they may also be referred to as a first modified polynucleotide oligomer, a second modified polynucleotide oligomer, a third modified polynucleotide oligomer, etc.

As used herein, the term "polynucleotide oligomer," "oligonucleotide oligomer", and "oligomer," which are considered to be interchangeable as used herein, refer to linear polymers of naturally occurring nucleotide monomers that are different from the "modified polynucleotide oligomer," "modified oligonucleotide oligomer," and "modified oligomer" of the present invention. Usually, nucleoside monomers of a "polynucleotide oligomer" are linked by phosphodiester linkages. However, modified polynucleotides oligomers containing non-phosphodiester linkages are also contemplated. "Modified polynucleotide oligomer" also encompasses polymers that contain one or more non-naturally occurring monomers and/or intersubunit linkages, such as peptide nucleic acids (PNAs, e.g., polymers comprising a backbone of amide-linked N-(2-aminoethyl)-glycine subunits to which nucleobases are attached via the non-amide backbone nitrogens. See Nielsen et al., *Science* 254:1497-1500 (1991)). Polynucleotide oligomers and modified polynucleotide oligomers typically range in size from a few monomer units, e.g. 8-40, to several thousand monomer units. Whenever a polynucleotide oligomer or modified polynucleotide oligomer is represented by a sequence of letters, such as "ATGCCTG," it will be understood that the nucleotides are in 5'→3' order from left to right and that "A" denotes adenosine, "C" denotes cytidine, "G" denotes guanosine, "T" denotes thymidine, and "U" denotes uridine, unless otherwise noted. For backbones which do not have a conventional 5' and/or 3' end (e.g., PNAs), the base sequence is provided as if in a 5'→3' order such that the sequence would hybridize in an antiparallel fashion to a complementary sequence having a 3'→5' orientation, as is the case in the antiparallel complementary strands of ordinary double stranded DNA.

When used alone, "polynucleotide" and "oligonucleotide" refer to polynucleotide oligomers composed primarily or entirely of conventional DNA or RNA monomer units—i.e., of deoxyribose or ribose sugar rings substituted with A, C, G, T or U bases and which are linked by conventional phosphate backbone moieties.

As used herein, the term "primer" refers to an oligomer or modified oligomer that is effective as a starting point to synthesize a polynucleotide strand that is complementary to a target nucleic acid strand. For example, primers for use in PCR comprise a forward and reverse primer wherein the forward primer contains a sequence complementary to a region of a target nucleic acid strand and guides synthesis of a complementary strand. A reverse primer contains a sequence complementary to the opposite stand and guides synthesis along the opposite strand of the target nucleic acid strand.

As used herein, the term "probe" refers to a labeled oligonucleotide or labeled modified oligonucleotide containing a sequence complementary to a region of a target nucleic acid sequence, allowing the probe to form a duplex with the target sequence and generate a detectable signal indicating the presence of the region of the target sequence. A detectable signal is generated during or after hybridization, either directly or indirectly. In some applications, such as during primer extension in 5'-nuclease PCR, the probes lack an extendable 3' hydroxyl group to prevent polymerase-mediated extension of the probe.

A "primer' or "probe" is typically an oligomer or a modified oligomer that comprises a region that is complementary to a sequence of at least 6 contiguous nucleotides of a target nucleic acid molecule, although primers and probes can comprise fewer than 6 contiguous nucleotides. In some embodiments, a modified oligomer is provided that comprises a sequence that is identical to, or complementary to 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, about 50 or more, or up to about 100 contiguous nucleotides of a target nucleic acid molecule. When a primer or probe comprises a region that is "complementary" to at least x contiguous nucleotides of a target nucleic acid molecule," the primer or probe is at least 95% complementary to at least x contiguous nucleotides of the target nucleic acid molecule. In some embodiments, the primer or probe is at least 96%, at least 97%, at least 98%, at least 99%, or 100% complementary to the target nucleic acid molecule. A preferred "probe" or "primer" is a "probe" or "primer" comprising a modified base, preferably a modified cytosine base.

As used herein, the terms "protecting group," "protective group", or "protected form" refer to a labile chemical modification of a functional group (e.g., a phosphate group or a phosphonate group) meant to preserve its functionality and/or to obtain chemoselectivity in a subsequent chemical reaction. A protecting group is removed from the final product by a deprotective treatment (e.g., treatment with concentrated aqueous ammonia). In some embodiments, phosphate and phosphonate protecting groups $X^1$ and $X^2$ are independently selected from protecting groups used for protection of phosphitylating reagents in automated phosphoramidite oligonucleotide synthesis and/or are compatible with the conditions of automated phosphoramidite oligonucleotide synthesis. In certain embodiments, groups $X^1$ and $X^2$ are independently optionally substituted benzyl, optionally substituted alkyl (e.g., cyanoethyl), and optionally substituted heteroalkyl. Exemplary amino protecting groups include, but are not limited to, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), and nitro-veratryloxycarbonyl (NVOC). Exemplary hydroxy protecting groups include those where the hydroxy group is either acylated or alkylated such as benzyl and trityl ethers as well as alkyl ethers, tetrahydropyranyl ethers, trialkylsilyl ethers and allyl ethers. See also Chapter 1: *Protecting Groups in Oligonucleotide Synthesis* by Etienne Sonveaux in *Methods in Molecular Biology*, Vol. 26, *Protocols for Oligonucleotide Conjugates*, S. Agrawal (Ed.), Humana Press Inc., Totowa, N.J. (1994); *Greene's Protective Groups in Organic Synthesis*, P. Wutz and T. Greene (Eds.), Wiley-Interscience, 4th Edition (2006); Thomson, S. A., et al., "*Fmoc Mediated Synthesis of Peptide Nucleic Acids*", *Tetrahedron* 51:6179-6194 (1995); and "*Solid-Phase Synthesis of Peptide Nucleic Acids*", *J. Peptide Science* 3:175-183 (1995); which are incorporated herein by reference for such disclosure.

As used herein, the term "salt" refers to salts of a compound, such as modified moiety described herein, which is prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., 1977, "Pharmaceutical Salts", *Journal of Pharmaceutical Science*, 66:1-19). Certain specific compounds of the present invention contain both basic and acidic functionalities that allow the compounds to be converted into either base or acid addition salts. The neutral forms of a compound may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As used herein, the term "solid support" refers to any insoluble material including particles (e.g., beads), fibers, monoliths, membranes, filters, plastic strips, arrays, and the like.

As used herein, the term "substantially complementary" refers to a sequence having no more than 20% (e.g., no more than 15%, 10% or 5%) of the nucleotides in the sequence in question mismatched with a target sequence. In some embodiments, the complementary strands of a hybridization complex have 1, 2, 3, 4, 5, or more nucleotide mismatches.

As used herein, the terms "target nucleic acid" or "target nucleic acid molecule" refer to a nucleic acid or polynucleotide oligomer that, in some embodiments, is the target for hybridization, amplification, etc., i.e., for purposes of detection. In some embodiments, target nucleic acids comprise RNA or DNA that is partially or fully complementary to a modified polynucleotide oligomer of the present invention.

As used herein, the terms "target sequence," "target nucleic acid sequence" or "target nucleotide sequence" refer to a sequence within a target nucleic acid. The target sequence can usually be described using the four bases of DNA (A, T, G, and C) or the four bases of RNA (A, U, G, and C).

II. Compositions

The disclosure provides polynucleotide oligomers which comprise one or more modified bases ("modified polynucleotide oligomers") that exhibit improved hybridization properties and are useful in hybridization reactions and as substrates for polymerase enzymes. The disclosure further relates to the use of such modified polynucleotide oligomers as probes and/or primers and in nucleotide arrays, for example.

Compositions, methods and kits comprising such modified polynucleotide oligomers are further provided. The modified polynucleotide oligomers provide for superior stability in base pairing between the modified polynucleotide oligomers and complementary polynucleotide sequences, as compared to oligomers that lack such modified bases.

In some embodiments, modified polynucleotide oligomers described herein comprise DNA, RNA, PNA and DNA/PNA chimeric oligomers. The modified bases and modified polynucleotide oligomers of the invention provide greater duplex stability for complementary sequences, and improved mismatch discrimination when one or more base mismatches are present in a hybridization complex.

Also provided are nucleosides and nucleotides containing modified bases of the invention. Such nucleosides may be used as precursors for synthesis of corresponding mono-, di- and triphosphate esters or as enzyme substrates. Nucleotides of the invention may be incorporated into polynucleotide oligomers by polymerase-mediated primer extension.

Various embodiments of the disclosure are discussed in detail below. While specific implementations are discussed, it should be understood that this is done for illustration purposes only. Other components and configurations may be used without parting from the spirit and scope of the disclosure.

A. Modified Cytosine Bases

The disclosure provides polynucleotide oligomers which comprise one or more modified bases that exhibit improved hybridization properties and are useful in hybridization reactions and as substrates for polymerase enzymes. Modified bases of the present invention are non-naturally occurring.

The modified bases disclosed herein comprise a phosphate or phosphonate group linked by a linker moiety to the 5-position of a pyrimidine ring structure. The modified bases of the invention may be considered to be analogs of the conventional bases cytosine. The 5-hydrogen atom of cytosine is replaced with the linker-phosphate or linker-phosphonate moiety as shown further below. In the present disclosure, the modified bases are sometimes represented as modified cytosine bases (e.g., $C^{BP}$ or $C^{PP}$).

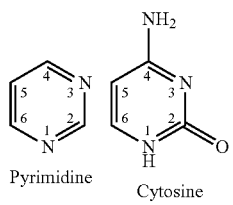

Pyrimidine Cytosine

The modified bases of the invention may be represented generally by the formula:

(Formula I)

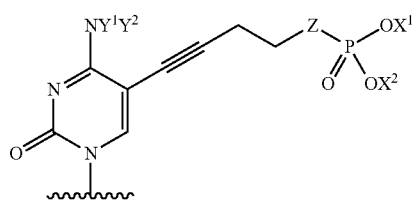

wherein Z is $CH_2$ or O; $Y^1$ and $Y^2$ are independently H or a protecting group; and $X^1$ and $X^2$ are independently H or a protecting group or together are a protecting group, and the wavy line indicates the point of attachment of the modified base to an oligomer backbone or to a monomeric backbone moiety such as a ribose ring of a deoxyribonucleoside, a ribose ring of a deoxyribonucleotide, or the backbone of a PNA amino acid monomer. When both of and $X^2$ are protecting groups, $X^1$ and $X^2$ taken separately can be the same or different, and $X^1$ and $X^2$ taken together can be a bidentate protecting group such as α,α-dimethyl-o-benzylene:

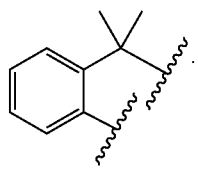 [SMILES: *c1ccccc1C(*)(C)C]

In a particular embodiment of the present invention, a modified base of the invention according to Formula I is a modified base, wherein Z is O and $X^1$ and $X^2$ taken together are α,α-dimethyl-o-benzylene:

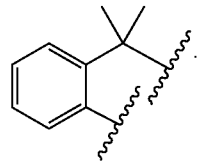 [SMILES: *c1ccccc1C(*)(C)C]

Further illustration of phosphate and phosphonate protecting groups and their methods of introduction can be found in *Greene's Protective Groups in Organic Synthesis*, P. Wutz and T. Greene (Eds), Wiley-Interscience, 4th Edition, 2006, which is incorporated herein by reference for such disclosure.

Typically, both $X^1$ and $X^2$ are protecting groups when it is desirable to protect the phosphate or phosphonate moiety from damage or modification during oligomer synthesis, as in the case of synthesis of as polynucleotide oligomer by the phosphoramidite method or of a PNA oligomer by peptide synthesis. In polynucleotide oligomers containing modified bases of the invention, the protecting groups are typically removed before the oligomer is used to hybridize to a complementary polynucleotide oligomer, in order to provide increased base-pairing affinity and aqueous solubility. Preferably, whenever $X^1$, $X^2$, or both and/or $Y^1$, $Y^2$, or both, are a protecting group or are protecting groups, the protecting group(s) are removable by ammonia treatment.

In some embodiments in which Z is O, the modified base comprises a phosphate moiety.

In some embodiments in which Z is $CH_2$, the modified base comprises a phosphonate moiety.

As described further below, modified polynucleotide oligomers, phosphoramidates, modified PNA monomers, modified nucleosides, and modified nucleotides of the present invention comprise one or more of the modified bases described above (Formula I).

B. Modified Polynucleotide Oligomers

The disclosure provides polynucleotide oligomers which comprise one or more modified bases that exhibit improved hybridization properties and are useful in hybridization reactions and as substrates for polymerase enzymes. They are referred to herein as "modified polynucleotide oligomers" and are non-naturally occurring The disclosure further relates to the use of such modified polynucleotide oligomers as probes and/or primers and in nucleotide arrays, for example.

In some embodiments, the modified polynucleotide oligomers described herein comprise 1, 2, 3, 4, 5, 6 or more modified bases in accordance with the formula above (see, Formula I). The number of modified bases within a modified polynucleotide oligomer will depend on the number of C bases in the oligomer sequence and the amount of increased binding affinity that is desired, which can be determined, as described herein, by melting studies or other experiments on different oligomer constructs to determine what is optimal for the needs of a particular application.

In some embodiments, modified polynucleotide oligomers are represented by the formula:

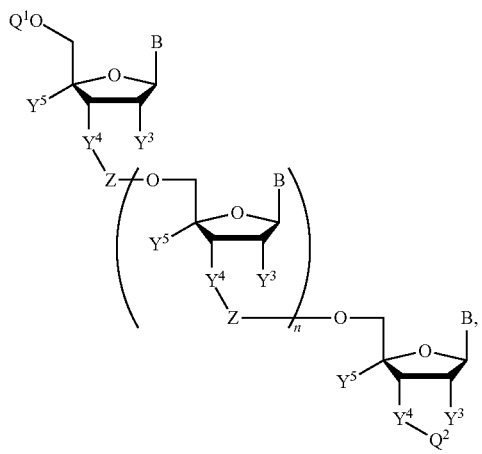

wherein each $Y^5$ is independently H, $C_1$-$C_8$ alkyl, or is optionally combined with $Y^3$ to form a 5- to 7-membered ring;
wherein each $Y^4$ is independently O, S, or NH;
wherein each $Y^3$ is independently H, F, or $OR^a$;
wherein each $R^a$ is independently H, $C_1$-$C_8$ alkyl, or a hydroxyl protecting group;
wherein each Z is independently P(O)OH, P(S)OH or P(O)$CH_3$;
wherein n is 1-98;
wherein $Q^1$ and $Q^2$ are each independently H, a monophosphate, a diphosphate, a triphosphate, a fluorescent reporter dye, or a quencher;
wherein each B is independently adenine, guanine, cytosine, thymine, uridine, diaminopurine, with the proviso that at least one B is a modified cytosine base represented by the formula:

(Formula I)

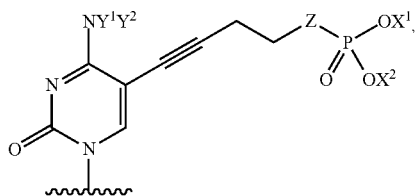

wherein Z is $CH_2$ or 0;
wherein $X^1$ and $X^2$ are the same or different, and taken separately are H or protecting group, or $X^1$ and $X^2$ taken together are a bidentate protecting group, such as α,α-dimethyl-o-benzylene:

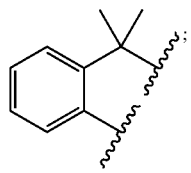 [SMILES: *c1ccccc1C(*)(C)C]

and
wherein and $Y^2$ are independently H or a nitrogen protecting group, or $Y^1$ and $Y^2$ together are a nitrogen protecting group.

In some embodiments, and $Y^2$ are H, and $X^1$ and $X^2$ are H. In some embodiments, Z is O. In some embodiments, Z is $CH_2$. Preferably, whenever $X^1$, $X^2$, or both, and/or $Y^3$, $Y^4$, or both, are a protecting group or are protecting groups, the protecting group(s) are removable by ammonia treatment.

In a particular embodiment, a modified polynucleotide oligomer is represented by the formula:

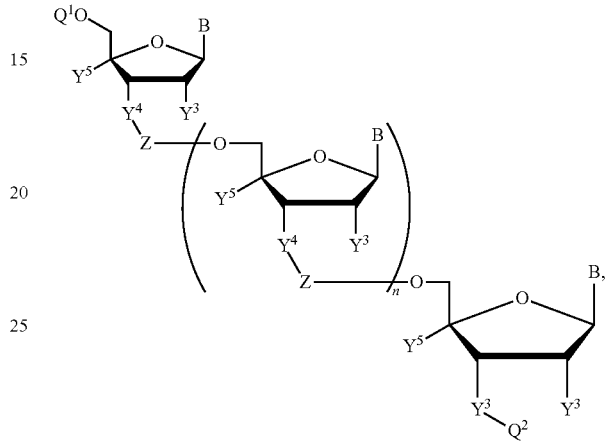

wherein each $Y^1$ is H;
wherein each $Y^2$ is O;
wherein each $Y^3$ is H;
wherein each $R^a$ is H;
wherein each Z is P(O)OH;
wherein n is 1-98;
wherein $Q^1$ and $Q^2$ are each independently H, monophosphate, diphosphate, triphosphate,
a fluorescent reporter dye, or a quencher, preferably a fluorescence quencher;
wherein each B is independently adenine, guanine, cytosine, thymine, uridine, diaminopurine, with the proviso that at least one B is a modified base represented by the formula:

(Formula I)

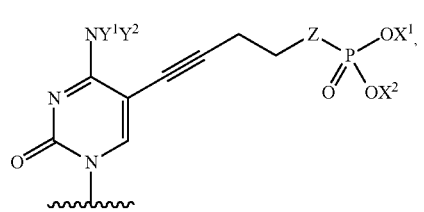

wherein Z is O; and wherein $X^1$ and $X^2$ taken together are α,α-dimethyl-o-benzylene

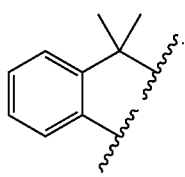 [SMILES: *c1ccccc1C(*)(C)C]

Modified polynucleotide oligomers of the present invention usually comprise or consist of a single-stranded polynucleotide having fewer than 100 nucleotides, although longer sequences of hundreds or thousands or more bases are also contemplated.

In some embodiments, a modified polynucleotide oligomer comprises fewer than 30 nucleotides, preferably, the oligonucleotide oligomer comprises from about 9 to about 25 nucleotides, i.e. 9, 10, 11, 12, 13, 14, 15, 16, 17, 18, 19, 20, 21, 22, 23, 24 or 25 nucleotides.

In some embodiments, a modified polynucleotide oligomer comprises, or consists of, from 2 to about 100, from 2 to about 50, from 2 to about 25, from 2 to about 15, from 5 to about 50, from 5 to about 25, from 5 to about 15, from about 10 to about 50, from about 10 to about 25, from about 10 to about 20, from about 10 to about 15, from about 12 to about 50, from about 12 to about 25 or from about 12 to about 20 nucleotides. Oligomers may be referred to by their length. For example, a 15 nucleotide oligomer may be referred to as a "15-mer."

As one of ordinary skill in the art will appreciate, the position within a modified polynucleotide oligomer, probe, primer or PNA where a modified cytosine base can be incorporated is not limited. Disclosed herein are polynucleotide oligomers, probes, primers and PNAs wherein a modified cytosine base is incorporated at various positions. In some embodiments, a modified cytosine base is in position 1 of a polynucleotide when written in a 5'→3' direction (e.g., see, Pf1-C-1, Pf1-C-4, Pf1-C-6, Pf1-C-8; Table 4). In some embodiments, a modified cytosine base is in position 2 of a polynucleotide when written in a 5'→3' direction. In some embodiments, a modified cytosine base is in position 3 of a polynucleotide when written in a 5'→3' direction (e.g., see, Pf1-C-2; Table 4). In some embodiments, a modified cytosine base is in position 4 of a polynucleotide when written in a 5'→3' direction (e.g., see, Pf1-C-3 Pf1-C-4, Pf1-C-5, Pf1-C-6; Table 4). In some embodiments, a modified cytosine base is in position 5 of a polynucleotide when written in a 5'→3' direction. In some embodiments, a modified cytosine base is in position 6 of a polynucleotide when written in a 5'→3' direction (e.g., see, C-PNA; Table 4). In some embodiments, a modified cytosine base is in position 7 of a polynucleotide when written in a 5'→3' direction (e.g., see, C1, C3, ; Table 4). In some embodiments, a modified cytosine base is in position 8 of a polynucleotide when written in a 5'→3' direction. In some embodiments, a modified cytosine base is in position 9 of a polynucleotide when written in a 5'→3' direction (e.g., see, Pf1-C-5, Pf1-C-6; Table 4). In some embodiments, a modified cytosine base is in position 10 of a polynucleotide when written in a 5'→3' direction (e.g., see, C2, C3, Pf1-C-7, Pf1-C-8; Table 4). In some embodiments, a modified cytosine base is in position 11 of a polynucleotide when written in a 5'→3' direction. In some embodiments, a modified cytosine base is in position 12 of a polynucleotide when written in a 5'→3' direction. In some embodiments, a modified cytosine base is in position 13 of a polynucleotide when written in a 5'→3' direction. In some embodiments, a modified cytosine base is in position 14 of a polynucleotide when written in a 5'→3' direction. In some embodiments, a modified cytosine base is in position 15 of a polynucleotide when written in a 5'→3' direction (e.g., see, Pf1-C-7, Pf1-C-8; Table 4). In some embodiments, a modified cytosine base is in position 16 of a polynucleotide when written in a 5'→3' direction (e.g., see, R1, P1R; Table 4). In some embodiments, a modified cytosine base is in position 17 of a polynucleotide when written in a 5'→3' direction. In some embodiments, a modified cytosine base is in position 18 of a polynucleotide when written in a 5'→3' direction. In some embodiments, a modified cytosine base is in position 19 of a polynucleotide when written in a 5'→3' direction (e.g., see, F1, P1F; Table 4). In some embodiments, a modified cytosine base is in position 20 of a polynucleotide when written in a 5'→3' direction (e.g., see, Pf1-C-7, Pf1-C-8; Table 4).

As one of ordinary skill in the art will appreciate, the number of modified cytosine bases within a polynucleotide oligomer, probe or primer is not limited. Disclosed herein are polynucleotide oligomers, probes, primers and PNAs comprising various numbers of modified cytosine bases. In some embodiments, a polynucleotide oligomer, primer, probe or PNA comprises one modified cytosine base (e.g., see, C-1, C2, F1, R1, Pf1-C-1, Pf1-C-2, Pf1-C-3, P1F, P1R, C-PNA; Table 4). In some embodiments, a polynucleotide oligomer, primer, probe or PNA comprises two modified cytosine bases (e.g., see, C3, Pf1-C-4, Pf1-C-5; Table 4). In some embodiments, a polynucleotide oligomer, primer, probe or PNA comprises three modified cytosine bases (e.g., see, Pf1-C-6, Pf1-C-7; Table 4). In some embodiments, a polynucleotide oligomer, primer, probe or PNA comprises four modified cytosine bases. In some embodiments, a polynucleotide oligomer, primer, probe or PNA comprises five modified cytosine bases (e.g., see, Pf1-C-8; Table 4). In some embodiments, a polynucleotide oligomer, primer, probe or PNA comprises at least one modified cytosine base. In some embodiments, a polynucleotide oligomer, primer, probe or PNA comprises at least two modified cytosine bases. In some embodiments, a polynucleotide oligomer, primer, probe or PNA comprises at least three modified cytosine bases. In some embodiments, a polynucleotide oligomer, primer, probe or PNA comprises at least four modified cytosine bases. In some embodiments, a polynucleotide oligomer, primer, probe or PNA comprises at least five modified cytosine bases. In some embodiments, a polynucleotide oligomer, primer, probe or PNA comprises at least six modified cytosine bases. In some embodiments, a polynucleotide oligomer, primer, probe or PNA comprises at least seven modified cytosine bases. In some embodiments, a polynucleotide oligomer, primer, probe or PNA comprises at least ten modified cytosine bases. In some embodiments, a polynucleotide oligomer, primer, probe or PNA comprises at least twenty modified cytosine bases.

In some embodiments, a modified polynucleotide oligomer of the present invention is attached to a solid support. In some embodiments, a modified polynucleotide oligomer of the present invention is attached to a bead. In some embodiments, a modified polynucleotide oligomer of the present invention is attached to an array. In some embodiments, a modified polynucleotide oligomer of the present invention is attached to a microarray.

1. Modified Polynucleotide Oligomers Comprising Further Modifications

In some embodiments, the modified polynucleotide oligomers comprising one or more modified bases of the invention will further comprise other types of modifications, such as comprising modified bases or base analogs and/or detectable labels, fluorescence and/or chemiluminescence quenchers and/or minor groove binders and/or one or more base modifications, sugar modifications and/or backbone modifications.

While in the following paragraphs, further modifications of a modified polynucleotide oligomer are described individually for clarity, one of ordinary skill in the art will appreciate that each of the individually described modifications can be combined with another one. For example, a further modified polynucleotide oligomer comprises a sugar modification and a backbone modification. In another non-limiting example, a further modified polynucleotide oligomer comprises a sugar modification and a label. In a further example, a further modified polynucleotide oligomer comprises a backbone modification and a label. In yet another non-limiting example, a further modified polynucleotide oligomer comprises a label and a base modification.

(a) Modified Polynucleotide Oligomers Comprising Sugar Modifications

In some embodiments, the modified polynucleotide oligomers described herein comprise one or more modified sugar moieties. A variety of sugar moieties can be used to modify a modified polynucleotide of the present invention. As one of ordinary skill in the art will appreciate, the location of a sugar modification within a modified polynucleotide oligomer of the present invention can vary and is not limited to the disclosure herein. In some embodiments, a sugar moiety for modifying a modified polynucleotide oligomer of the present invention includes, but is not limited to, arabinose, d-arabino-hexitol, 2-fluoroarabinose, xylulose, and a hexose. In some embodiments, a sugar moiety for modifying a modified polynucleotide oligomer of the present invention is selected from the group consisting of arabinose, d-arabino-hexitol, 2-fluoroarabinose, xylulose, and a hexose.

In some embodiments, a modified polynucleotide oligomer of the present invention includes one or more nucleotides having attached a modified sugar moiety. A variety of sugar moieties can be used to attach to a nucleotide which will be incorporated into a modified polynucleotide oligomer of the present invention. In some embodiments, a sugar moiety attached to a nucleotide includes is a 2'-substituted sugar, such as a 2'-O-alkyl-ribose sugar, a 2'-amino-deoxyribose sugar, a 2'-fluoro-deoxyribose sugar, a 2'-fluoro-arabinose sugar, or a 2'-O-methoxyethyl-ribose (2' MOE) sugar. In some embodiments, a sugar moiety attached to a nucleotide is selected from the group consisting of a 2'-substituted sugar, such as a 2'-O-alkyl-ribose sugar, a 2'-amino-deoxyribose sugar, a 2'-fluoro-deoxyribose sugar, a 2'-fluoro-arabinose sugar, and a 2'-O-methoxyethyl-ribose (2' MOE) sugar. In a particular embodiment of the present invention, the sugar moiety attached to the nucleotide is a 2'-O-methoxyethyl-ribose (2' MOE) sugar.

In some embodiments, a modified polynucleotide oligomer comprises a locked nucleic acid ("LNA") sugar. A LNA sugar is a bicyclic sugar, i.e., containing a methylene bridge between C-4' and an oxygen atom at C-2'. In some embodiments, a modified polynucleotide oligomer comprises one or more nucleotides having an LNA sugar. In some embodiments, a modified polynucleotide oligomer contains one or more regions consisting of nucleotides with LNA sugar moieties. In some embodiments, a modified oligonucleotide oligomer contains nucleotides with LNA sugar moieties interspersed with deoxyribonucleotides. See, e.g., Frieden, M. et al. (2008) Curr. Pharm. Des. 14(11): 1138-1142.

(b) Modified Polynucleotide Oligomers Comprising Backbone Modifications

In some embodiments, a modified polynucleotide oligomer comprise a backbone modification. Various backbone modifications can be introduced into a modified oligonucleotide. As one of ordinary skill in the art will appreciate, the location of a backbone modification within a modified polynucleotide oligomer of the present invention can vary and is not limited to the disclosure herein.

In some embodiments, a modified polynucleotide oligomer comprises one or more phosphodiester linkages. In some embodiments, nucleotide analogs include backbone modifications such as the use of a peptide nucleic acid (PNA). In some embodiments, a modified polynucleotide oligomer comprises a modified linkage, such as a phosphotriester, a phosphoramidate, a siloxane, a carboxymethylester, an acetamidate, a carbamate, a thioether, a bridged phosphoramidate, a bridged methylene phosphonate, a phosphorothioate, a methylphosphonate, a alkylphosphonate, a phosphate ester, an alkylphosphonothioate, a phosphorodithioate, a carbonate, a phosphate triester, a carboxymethyl ester, a methylphosphorothioate, a phosphorodithioate, a p-ethoxy linkages, and combinations thereof. In some embodiments, a modified polynucleotide oligomer comprises a modified linkage selected from the group consisting of a phosphotriester, a phosphoramidate, a siloxane, a carboxymethylester, an acetamidate, a carbamate, a thioether, a bridged phosphoramidate, a bridged methylene phosphonate, a phosphorothioate, a methylphosphonate, a alkylphosphonate, a phosphate ester, an alkylphosphonothioate, a phosphorodithioate, a carbonate, a phosphate triester, a carboxymethyl ester, a methylphosphorothioate, a phosphorodithioate, a p-ethoxy linkages, and combinations thereof.

For example, PNAs can be readily synthesized to contain conventional DNA bases (A, C, T and G) or unconventional bases, but the PNA monomer units are linked by a polyamide backbone instead of a sugar-phosphate backbone.

(c) Modified Polynucleotide Oligomers Comprising Base Modifications

In some embodiments, a modified polynucleotide oligomer comprises one or more non-standard bases (i.e., other than adenine, guanine, thymine, cytosine and uracil). Various non-standard bases can be introduced into a modified oligonucleotide. As one of ordinary skill in the art will appreciate, the location of a base modification within a modified polynucleotide oligomer of the present invention can vary and is not limited to the disclosure herein. Such non-standard bases may serve a number of purposes, e.g., to stabilize or destabilize hybridization; to promote or inhibit probe degradation; or as attachment points for detectable moieties or quencher moieties. Numerous examples of modified bases (other than the modified bases of the invention) and base analogs are noted above, are known in the art, and can be used to further modify a modified polynucleotide oligomer.

In some embodiments, a modified oligomer comprises a modified base that is an amine-modified nucleotide, i.e., a nucleotide that has been modified to contain a reactive amine group.

Modified polynucleotide oligomers of the present invention may comprise any combination of normal or modified bases, such as unsubstituted pyrazolo[3,4-d]pyrimidine bases (e.g., PPG and PPA), 3-substituted pyrazolo[3,4-d]pyrimidines, modified purines, modified pyrimidines, 5-substituted pyrimidines or universal bases, for example.

(d) Modified Oligonucleotide Oligomers Comprising A Label

In some embodiments, a modified polynucleotide oligomer comprises a label, preferably a detectable label. A modified polynucleotide oligomer comprising a detectable label is used as a probe or as a primer, for example, as described herein. Various labels can be introduced into a modified oligonucleotide. As one of ordinary skill in the art will appreciate, the location of a label within a modified polynucleotide oligomer of the present invention can vary and is not limited to the disclosure herein.

In some embodiments, a modified polynucleotide oligomer comprises a fluorophore on one end of its sequence and/or a fluorescence quencher on the other end of its sequence so that the fluorescence quencher suppresses the fluorescence signal of the fluorophore in the intact probe (i.e., the modified polynucleotide oligomer being used as a probe) via an energy transfer mechanism such as fluorescence resonance energy transfer ("FRET"). When a polymerase extends a primer along a template to which the probe has also hybridized, the 5'-nuclease activity of the polymerase cleaves the probe (i.e., the modified polynucleotide oligomer), thereby allowing the fluorophore to diffuse away from the fluorescence quencher so that the fluorescent signal is now detected. The signal increases with each PCR cycle proportionally to the amount of probe that is cleaved, and thus, proportionally to the amount of amplification product (amplicon, target sequence). This allows direct detection and quantification of the target DNA sequence. In some embodiments, a fluorophore is attached to base that is at least one nucleotide position away from the end of the sequence of the modified polynucleotide oligomer and/or the fluorescence quencher is attached to a base that is at least one nucleotide position away from the other end of the modified polynucleotide oligomer. In some embodiments, the fluorophore and/or the fluorescence quencher are located internally within a modified polynucleotide oligomer. As one of ordinary skill in the art will appreciate, the location of the fluorophore and/or the fluorescence quencher within a modified polynucleotide oligomer of the present invention can vary and is not limited.

In some embodiments, the fluorophore and fluorescence quencher are not at the ends of a FRET probe. In some embodiments, the emission spectrum of the fluorophore overlaps considerably with the absorption spectrum of the fluorescence quencher. However, such spectral overlap is less important or not required when quenching involves a collisional mechanism, or the overlap is increased due to reaction conditions or probe structure, for example.

In some embodiments, labels that are used on FRET probes (i.e., on modified polynucleotide oligomers that are used as FRET probes) include colorimetric and dyes or fluorophores such as Alexa Fluor dyes, BODIPY dyes, such as BODIPY FL; Cascade Blue; Cascade Yellow; coumarin and its derivatives, such as 7-amino-4-methylcoumarin, aminocoumarin and hydroxycoumarin; cyanine dyes, such as Cy3 and Cy5; eosins and erythrosins; fluorescein and its derivatives, such as fluorescein isothiocyanate; macrocyclic chelates of lanthanide ions, such as Quantum Dye™; Marina Blue; Oregon Green; rhodamine dyes, such as rhodamine red, tetramethylrhodamine and rhodamine 6G; Texas Red; fluorescent energy transfer dyes, such as thiazole orange-ethidium heterodimer; and, TOTAB.

Specific examples of useful dyes that can be used to modify a modified polynucleotide oligomer of the present invention include, but are not limited to, those identified above and the following: Alexa Fluor 350, Alexa Fluor 405, Alexa Fluor 430, Alexa Fluor 488, Alexa Fluor 500. Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODIPY 530/550, BODIPY 558/568, BODIPY 564/570, BODIPY 576/589, BODIPY 581/591, BODIPY 630/650, BODIPY 650/655, BODIPY FL, BODIPY R6G, BODIPY TMR, and, BODIPY-TR; Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'tetrabromosulfone-fluorescein, TET, and Texas Red.

Examples of fluorophore/fluorescence quencher pairs (i.e., donor/acceptor pairs) that can be used to modify a modified polynucleotide oligomer of the present invention include, but are not limited to, fluorescein/tetramethylrhodamine; IAEDANS/fluorescein; EDANS/dabcyl; fluorescein/fluorescein; BODIPY FL/BODIPY FL; fluorescein/QSY 7 or fluorescein/QSY 9. When the donor and acceptor are the same, FRET may be detected, in some embodiments, by fluorescence depolarization. Certain specific examples of fluorophore/quencher pairs (i.e., donor/acceptor pairs) include, but are not limited to, Alexa Fluor 350/Alexa Fluor 488; Alexa Fluor 488/Alexa Fluor 546; Alexa Fluor 488/Alexa Fluor 555; Alexa Fluor 488/Alexa Fluor 568; Alexa Fluor 488/Alexa Fluor 594; Alexa Fluor 488/Alexa Fluor 647; Alexa Fluor 546/Alexa Fluor 568; Alexa Fluor 546/Alexa Fluor 594; Alexa Fluor 546/Alexa Fluor 647; Alexa Fluor 555/Alexa Fluor 594; Alexa Fluor 555/Alexa Fluor 647; Alexa Fluor 568/Alexa Fluor 647; Alexa Fluor 594/Alexa Fluor 647; Alexa Fluor 350/QSY35; Alexa Fluor 350/dabcyl; Alexa Fluor 488/QSY 35; Alexa Fluor 488/dabcyl; Alexa Fluor 488/QSY 7 or QSY 9; Alexa Fluor 555/QSY 7 or QSY9; Alexa Fluor 568/QSY 7 or QSY 9; Alexa Fluor 568/QSY 21; Alexa Fluor 594/QSY 21; and Alexa Fluor 647/QSY 21. In some embodiments, the same quencher may be used for multiple fluorophores, for example, a broad spectrum quencher, such as an Iowa Black® quencher (Integrated DNA Technologies, Coralville, Iowa) or a Black Hole Quencher™ or (BHQ™; Biosearch Technologies, Petaluma, Calif.). Thus, in some embodiments of the present invention, a modified polynucleotide oligomer comprises a fluorophore/fluorescence quencher pair selected from the group consisting of fluorescein/tetramethylrhodamine; IAEDANS/fluorescein; EDANS/dabcyl; fluorescein/fluorescein; BODIPY FL/BODIPY FL; fluorescein/QSY 7 fluorescein/QSY 9, Alexa Fluor 350/Alexa Fluor 488; Alexa Fluor 488/Alexa Fluor 546; Alexa Fluor 488/Alexa Fluor 555; Alexa Fluor 488/Alexa Fluor 568; Alexa Fluor 488/Alexa Fluor 594; Alexa Fluor 488/Alexa Fluor 647; Alexa Fluor 546/Alexa Fluor 568; Alexa Fluor 546/Alexa Fluor 594; Alexa Fluor 546/Alexa Fluor 647; Alexa Fluor 555/Alexa Fluor 594; Alexa Fluor 555/Alexa Fluor 647; Alexa Fluor 568/Alexa Fluor 647; Alexa Fluor 594/Alexa Fluor 647; Alexa Fluor 350/QSY35; Alexa Fluor 350/dabcyl; Alexa Fluor 488/QSY 35; Alexa Fluor 488/dabcyl; Alexa Fluor 488/QSY 7 or QSY 9; Alexa Fluor 555/QSY 7 or QSY9; Alexa Fluor 568/QSY 7 or QSY 9; Alexa Fluor 568/QSY 21; Alexa Fluor 594/QSY 21; and Alexa Fluor 647/QSY 21.

In some embodiments, for example, in a multiplex reaction in which two or more moieties are detected simultaneously, each modified polynucleotide oligomer probe may comprise a detectably different fluorophore such that the fluorophores may be distinguished when detected simultaneously in the same reaction. One skilled in the art can select a set of detectably different fluorophores for use in a multiplex reaction from the above disclosed fluorophore/fluorescence quenchers and others known in the art. As one of ordinary skill in the art will appreciate, the choice of a fluorophore and/or fluorescence quencher and location of the fluorophore and/or fluorescence quencher within a modified polynucleotide oligomer of the present invention can vary and is not limited to the disclosure herein.

(e) Modified Oligonucleotide Oligomers Comprising Other Modifications

In some embodiments, a modified polynucleotide oligomer described herein further comprises one or more pendant groups. A variety of pendant groups can be used for modifying a modified polynucleotide oligomer of the present invention. As one of ordinary skill in the art will appreciate, the choice of a pendant group and location of the pendant group within a modified polynucleotide oligomer of the present invention can vary and is not limited to the disclosure herein. A pendant group can be a moiety, such as a lipophilic group, a minor groove binder, an intercalator, a chelating agent or a cross-linking agent, attached to one or more internally located bases, to a 3'-terminus, to a 5'-terminus, to both termini, or internally and at one or both termini of a modified polynucleotide oligomer. Thus, in some embodiments, a pendant group attached to a modified polynucleotide oligomer is a moiety selected from the group consisting of a lipophilic group, a minor groove binder, an intercalator, a chelating agent and a cross-linking agent. Methods suitable for attaching such pendant groups are generally known in the art.

In some embodiments, a modified polynucleotide oligomer of the present invention comprises a low molecular weight "tail moiety." A variety of "tail moieties" can be used for further modifying a modified polynucleotide oligomer of the present invention. As one of ordinary skill in the art will appreciate, the choice of a "tail moiety" and location of the "tail moiety" within a modified polynucleotide oligomer of the present invention can vary and is not limited to the disclosure herein. In some embodiments, a tail moiety is attached either at the 3' or 5' end, or at both ends of a modified polynucleotide oligomer. A tail molecule can be a phosphate, a phosphate ester, an alkyl group, an aminoalkyl group, or a lipophilic group. Thus, in some embodiments, a tail moiety attached to a modified polynucleotide oligomer is selected from the group consisting of a phosphate, a phosphate ester, an alkyl group, an aminoalkyl group, and a lipophilic group. In some embodiments, a tail moiety links an intercalator, a lipophilic group, a minor groove binder (MGB), a reporter group, a chelating agent or a cross-linking functionality to a modified polynucleotide oligomer. For example, an MGB can be attached at either or both ends of the modified oligonucleotide oligomer. In addition or alternatively, one or more MGBs can be attached in an interior location within the modified oligonucleotide oligomer. As one of ordinary skill in the art will appreciate, such choice may depend on the length of the modified oligonucleotide oligomer.

In some embodiments, a modified polynucleotide oligomer comprises unnatural proportions of an atomic isotope. In some embodiments, a modified polynucleotide oligomer is radiolabeled. Suitable radiolabels include, but are not limited to tritium ($^3$H), iodine-125 ($^{125}$I), phosphor ($^{32}$P) or carbon-14 ($^{14}$C).

In some embodiments, a modified polynucleotide oligomer is provided in a salt form. Modified polynucleotide oligomers can be provided in various salt forms. As one of ordinary skill in the art will appreciate, the salt form of modified polynucleotide oligomer of the present invention can vary and is not limited to the disclosure herein. Salt forms of modified polynucleotide oligomers of the present invention include, but are not limited to, base addition salts such as sodium, potassium, calcium, ammonium, organic amino, or magnesium salt, or a similar salt.

In some embodiments, modified polynucleotide oligomers described herein comprise basic and/or acidic functionalities. The charge state of any ionizable group will depend on the pH of the environment. For example, the non-bridge oxygen atoms of a phosphate group within a modified polynucleotide oligomer will tend to be more protonated under acidic pH conditions than under basic pH conditions. Thus, although structures may be shown with a particular protonation state (e.g., a fully protonated phosphate diacid moiety), the true protonation state of ionizable groups within modified polynucleotide oligomers will depend on factors such as pH, water content, and salt concentration of the solvent.

In some embodiments, modified polynucleotide oligomers possess asymmetric carbon atoms or double bonds, e.g., are provided as racemates, diastereomers, geometric isomers and individual isomers all of which are intended to be encompassed within the scope of the invention. For example, although conventional DNA and RNA comprise D-stereoisomers of nucleotide subunits, the L-stereoisomers of DNA and RNA are also encompassed by the present disclosure.

C. Modified Nucleoside Phosphoramidites

The present invention also provides modified nucleoside phosphoramidites represented by the formulas:

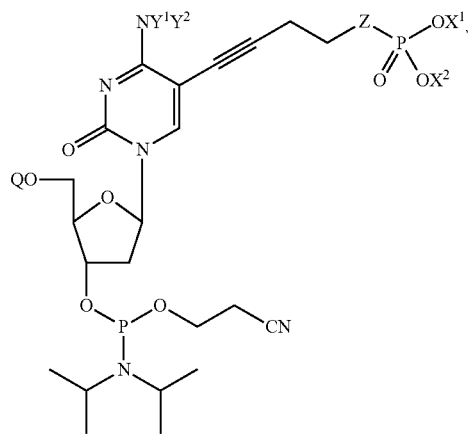

wherein Z is $CH_2$ or O;

wherein $X^1$ and $X^2$ taken separately are protecting groups that are the same or different, or wherein $X^1$ and $X^2$ taken together are a bidentate protecting group;

wherein and $Y^2$ are independently H or nitrogen protecting group, or $Y^1$ and $Y^2$ together are nitrogen protecting group; and wherein Q is a hydroxyl protecting group.

In some embodiments, Z is O. In some embodiments, Z is $CH_2$. In a particular embodiment of the present invention, Z is O.

In some embodiments, Q is trityl, methoxytrityl (MMT), or dimethoxytrityl (DMT). Preferably, Q is removable under acidic conditions.

Preferably, whenever $X^2$, or both, and/or $Y^1$, $Y^2$, or both, are a protecting group or are protecting groups, the protecting group(s) are removable by ammonia treatment. In some embodiments, $X^1$ and $X^2$ taken together are a bidentate protecting group such as o-benzylene, α-methyl-o-benzylene, or α,α-dimethyl-o-benzylene. In some embodiments, $Y^1$ and $Y^2$ together are nitrogen protecting group. In some embodiments, the modified nucleoside phosphoramidite may comprise a combination of any of the foregoing exemplary features.

In some embodiments of the modified nucleoside phosphoramidites, when protecting groups $X^1$ and $X^2$ are taken separately, each may have a structure represented by the formula:

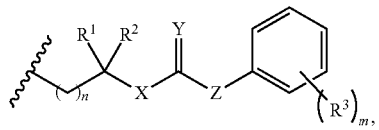

wherein $R^1$ and $R^2$ are independently hydrogen, $C_1$-$C_6$ alkyl, $C_2$-$C_6$ alkenyl, $C_2$-$C_6$ alkynyl, $C_3$-$C_6$ cycloalkyl, or phenyl; n and m are independently 0, 1, 2, 3 or 4; X is O or $NR^4$; Y is O or S; Z is a bond, 0 or $NR^4$; each $R^3$ is same or different and is, independently, $C_1$-$C_6$ alkyl, $C_2$-$C_6$ alkenyl, $C_2$-$C_6$ alkynyl, $C_3$-$C_6$ cycloalkyl, cyano, nitro, halogen, $C_1$-$C_6$ alkyloxy, $C_3$-$C_6$ cycloalkyloxy, $NR^{5a}R^{5b}$, or phenyl; $R^4$, $R^{5a}$ and $R^{5b}$ are each independently $C_3$-$C_6$ cycloalkyl, or phenyl. (See, for example, WO 2000/055179 A1).

In some embodiments of the modified nucleoside phosphoramidites, $X^1$ and $X^2$ independently have the structure:

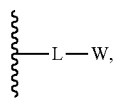

wherein L is a bond, $C_1$-$C_8$ alkylene or $C_2$-$C_8$ heteroalkylene, $C_2$-$C_8$ alkenylene; and W is H, cyano, $C(O)NR^aR^b$, $NO_2$, $N^+R^aR^bR^c$, $C_6H_4NO_2$, $C_6H_4Cl$, $C_6H_3(NO_2)_2$, $C_6H_2(NO_2)_3$, $SO_2R^c$, or $S(O)_2OR^c$; $R^a$ and $R^b$ are independently H, $CF_3$, $C_1$-$C_8$ alkyl or $C_6$-$C_{10}$ aryl; and $R^c$ is $C_1$-$C_8$ alkyl or $C_6$-$C_{10}$ aryl. Such groups are advantageous since they can be removed by conventional ammonia or ammonium hydroxide treatment. In a particular embodiment of the present invention, the modified nucleoside phosphoramidite according to the formula above is a modified nucleoside phosphoramidite, wherein $X^1$ and $X^2$ independently have the structure:

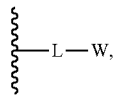

wherein L is a bond and W is H.

In some embodiments, $X^1$ and $X^2$ are each separately pivaloyloxybenzyl groups.

Modified nucleoside phosphoramidates of the present invention are non-naturally occurring. As one of ordinary skill in the art will appreciate, the modified nucleoside phosphoramidites are useful for synthesizing modified polynucleotide oligomers of the invention.

D. Modified PNA Monomers

The present invention also provides protected modified PNA monomers represented by the formula:

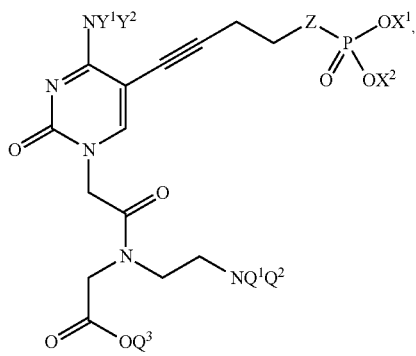

wherein Z is $CH_2$ or 0;

wherein $X^1$ and $X^2$ taken separately are protecting groups that are the same or different, or wherein $X^1$ and $X^2$ taken together are a bidentate protecting group;

wherein and $Y^2$ are independently H or nitrogen protecting group, or $Y^1$ and $Y^2$ together are nitrogen protecting group;

wherein $Q^1$ and $Q^2$ are independently H or nitrogen protecting group, or $Q^1$ and $Q^2$ together are nitrogen protecting group; and wherein $Q^3$ is H or a carboxyl protecting group.

In some embodiments of a modified PNA monomer, Z is O. In some embodiments, Z is $CH_2$. In a particular embodiment of the present invention, a protected modified PNA monomer according to the above formula is a protected modified PNA monomer, wherein Z is O.

In some embodiments, is H and $Q^2$ is Fmoc, and $Q^3$ is H. Preferably, whenever $X^1$, $X^2$, or both, and/or $Y^1$, $Y^2$, or both, are a protecting group or are protecting groups, the protecting group(s) are removable by ammonia treatment.

Modified PNA monomers of the present invention are non-naturally occurring.

E. Modified Nucleosides And Modified Nucleotides

The present invention also provides modified nucleosides represented by the formulas:

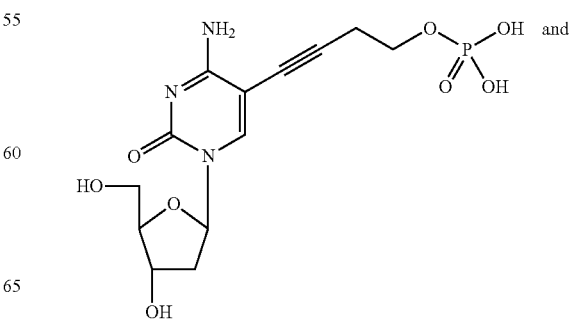

-continued

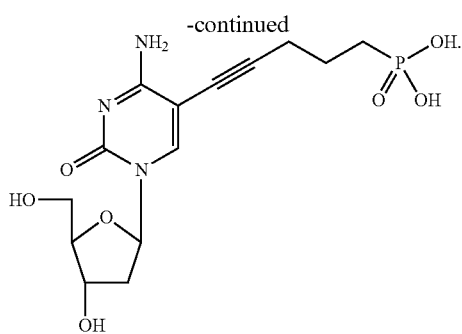

In a particular embodiment of the present invention, a modified nucleoside is represented by the formula:

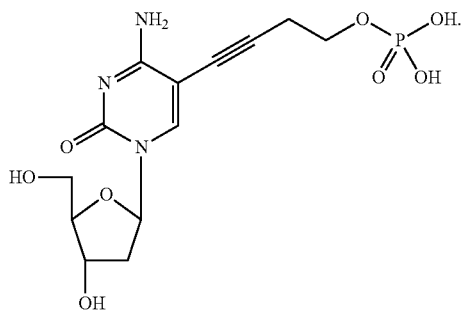 [SMILES: Nc1nc(=O)n(C2CC(O)C(CO)O2)cc1C#CCCOP(=O)(O)O]

The modified nucleosides of the present invention are non-naturally occurring. They are useful, e.g., as substrates in any reaction, whether chemical or enzymatic, for which the corresponding conventional DNA and RNA nucleoside cytosine is the substrate. For example, the nucleosides can be converted to mono-, di-, and triphosphates by the appropriate kinase enzymes. General procedures for making such modified cytosine nucleosides are provided, e.g., in Example 11.

The present disclosure also provides nucleotides represented by the formulas NT1 and NT2 shown in Example 12 below. The present invention also provides modified nucleotides represented by the formulas:

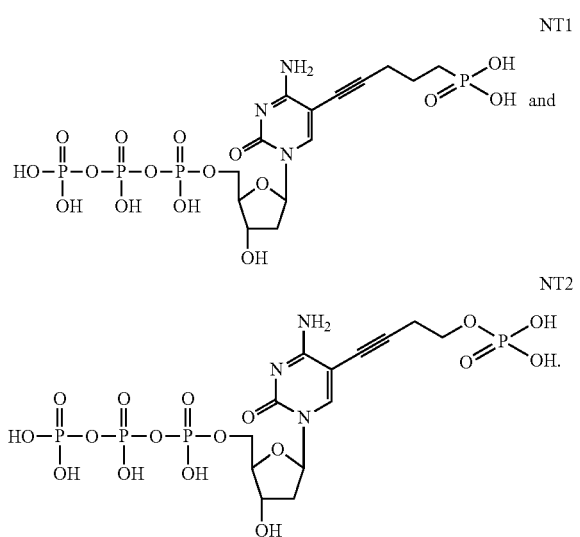

In a particular embodiment of the present invention, a modified cytosine nucleotide is represented by the formula:

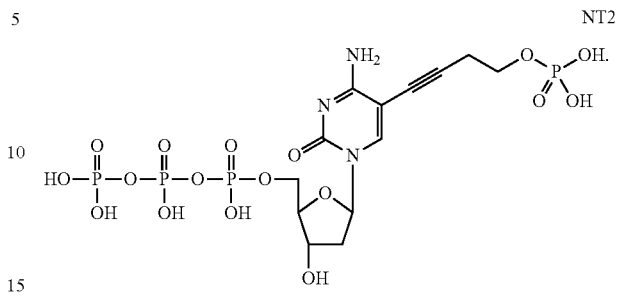

General procedures for making such modified cytosine nucleotide 5'-triphosphates are provided, e.g., in Example 12. Modified nucleotides of the invention can also be introduced into polynucleotide oligomers using nucleotidyl transferase in the same manner as conventional nucleotides and such produce a modified polynucleotide oligomer.

The modified cytosine nucleotides of the present invention are non-naturally occurring. Such nucleotides may be used instead of corresponding conventional cytidine phosphate esters in any enzymatic or synthetic reaction in which it is desirable to use a modified base of the invention. For example, a nucleotide 5'-triphosphate comprising a modified cytosine base of the invention can be incorporated into a modified polynucleotide oligomer by DNA polymerases. This can be done, e.g., to enhance hybridization affinity of the resulting primer extension product(s). In a non-limiting example, this is done as follows: (a) providing a mixture comprising a template-dependent DNA polymerase, a nucleotide 5'-triphosphate of the invention, and optionally one or more deoxynucleotide triphosphates such as dATP, dCTP, dGTP, and/or conventional TTP) and other buffer components, such as $Mg^{2+}$ and/or $Mn^{2+}$ ions; and (b) annealing a primer to a complementary sequence in a template DNA or RNA strand, so that a polymerase can incorporate a modified base (i.e., a modified nucleotide), and other NTPs if present, into an extended primer, thereby forming a polynucleotide oligomer comprising a modified base of the invention. See also, Kutyavin, I., *Biochemistry* 47:13666-13673 (2008), *"Use of Base-Modified Duplex-Stabilizing Deoxynucleoside 5'-Triphosphates to Enhance the Hybridization Properties of Primers and Probes in Detection Polymerase Chain Reaction,"* for suitable reaction conditions for primer extension.

F. Duplexes

In some embodiments, the present invention provides a duplex comprising a modified polynucleotide oligomer and a polynucleotide sequence. In some embodiments, the present invention provides a duplex comprising a plurality of modified polynucleotide oligomers and a polynucleotide sequence. In some embodiments, the present invention provides a duplex comprising at least one modified polynucleotide oligomer and a polynucleotide sequence. While the modified polynucleotide oligomer within such duplex is a non-naturally occurring oligomer, in some embodiments, the polynucleotide sequence within the duplex is a naturally occurring polynucleotide sequence. In some embodiment, both the modified polynucleotide and the polynucleotide sequence are non-naturally occurring. In some embodiments of a duplex of the present invention, the at least one modified polynucleotide oligomer comprises four or more contiguous bases that are complementary with and hybridized to at least four contiguous bases of the polynucleotide sequence.

As one of ordinary skill in the art will appreciate any modified polynucleotide oligomer described herein and any modified polynucleotide comprising any further modification as described herein can be used to form a duplex with a polynucleotide sequence. Also, the polynucleotide sequence is not limiting. Any polynucleotide that has at least four or more contiguous nucleotides of complementarity to a modified polynucleotide can be used.

In some embodiments, the polynucleotide sequence comprises a prokaryotic nucleotide sequence. In some embodiments, the polynucleotide sequence comprises a eukaryotic nucleotide sequence. In some embodiment, the polynucleotide sequence comprises a viral nucleotide sequence.

In some embodiments of a duplex, the polynucleotide sequence is longer than the modified polynucleotide oligomer, i.e., the polynucleotide sequence comprises more nucleotides than the modified polynucleotide oligomer.

In some embodiments, the duplex is attached to a solid support. In some embodiments, a duplex of the present invention is attached to a bead. In some embodiments, a duplex of the present invention is attached to an array. In some embodiments, a duplex of the present invention is attached to a microarray.

III. Methods

A. Synthesizing Modified Polynucleotides, Modified Nucleosides, Modified Nucleotides, and Other Moieties Comprising a Modified Cytosine Base Oligomers, nucleosides, nucleotides, and other moieties containing a modified cytosine base of the present invention can be synthesized by any suitable method and are typically synthesized chemically and/or enzymatically. Preferred methods are described herein, e.g., see Examples 1-4, 8, 9, 11 and 12.

For example, modified polynucleotide oligomers can be synthesized in the laboratory by solid-phase synthesis using a phosphoramidite method and phosphoramidite building blocks derived from suitably protected 2'-deoxynucleosides (dA, dC, dG, and dT), ribonucleosides (A, C, G, and U), or chemically modified nucleosides, e.g. LNA, BNA, etc. Polynucleotide chain assembly typically proceeds in the direction from 3'- to 5'-terminus by following a routine procedure referred to as a "synthetic cycle". Completion of a single synthetic cycle results in the addition of one nucleotide residue to the growing chain. HPLC and other methods known in the art are used to isolate modified polynucleotide oligomers having a desired sequence.

Methods of synthesizing polynucleotides and analogs thereof have been described in numerous publications, are well known and can be used, in addition to the methods described in Examples 1-4, 8, 9, 11, and 12, to synthesize the modified moieties of the present invention. See, for example Gait, Oligonucleotide Synthesis, IRL Press (1990), and S. Agrawal, *Protocols for Oligonucleotides and Analogs, Methods in Molecular Biology* Vol. 20, Humana Press, Totowa, N.J. (1993). For modified PNA oligomer synthesis, conventional peptide synthesis methods may be used as are known in the art (see, for example Nielsen et al., *Science* 254:1497-1500 (1991)). Enzymatic methods can also be used, such as primer extension mediated by DNA polymerases or the phosphorylation of a nucleoside at the 5' position using an appropriate kinase.

Various properties of illustrative polynucleotide oligomers of the invention are further illustrated in Examples 1 through 12 herein.

Examples 8 through 11 herein describe synthesis and characterization of several exemplary PNA oligomers in accordance with the invention.

B. Exemplary Utilities of Modified Polynucleotides, Modified Nucleosides, Modified Nucleotides, and Other Moieties Comprising a Modified Cytosine Base As one of ordinary skill in the art will appreciate upon reading this disclosure, the modified bases, and the modified polynucleotide oligomers, modified nucleosides, modified nucleotides, and other modified moieties containing them and which are described herein, find various uses in the field of nucleic acids processing and manipulation. For example, they are useful to enhance duplex stability, e.g., in hybridization complexes, such as polynucleotide duplexes and triplexes. In some embodiments, the modified polynucleotide oligomers are used as molecular probes, for example, in DNA sequencing, library construction, arrays, Southern blots, ASO analysis, fluorescent in situ hybridization (FISH), artificial gene synthesis, as primers for polymerase chain reaction (PCR) and the like, in ligation assays (e.g., for the detection of known single nucleotide polymorphisms), etc. The above listed methods are known in the art. One of ordinary skill in the art will have no difficulty substituting, e.g., a naturally occurring base, a naturally occurring nucleoside, a naturally occurring nucleotide or a naturally occurring polynucleotide oligomer used in any of those methods with a non-naturally occurring modified cytosine base as described herein, with a non-naturally occurring modified nucleoside as described herein, with a non-naturally occurring modified nucleotide or with a non-naturally occurring modified polynucleotide oligomer as described herein.

In some embodiments, modified polynucleotide oligomers comprising one or more modified cytosine bases of the present invention improve the efficiency of primer extension reactions. The added duplex stability provided by the modified cytosine bases of the present invention enables skilled artisans to perform primer extension at higher temperatures than with naturally occurring polynucleotide oligomers that lack such modified cytosine bases. Thereby, primer extension times and/or the transition ramp times between the denaturation temperature and annealing temperature can be reduced. Higher reaction temperatures are also advantageous for minimizing potentially problematic secondary structures in target molecules and can reduce the formation of primer dimers. Further, without being bound by theory, it is believed that the use of higher reaction temperatures also reduces noise.

The following describes some non-limiting uses of the non-naturally occurring modified cytosine bases, non-naturally occurring modified nucleosides, non-naturally occurring modified nucleotides and non-naturally occurring modified polynucleotide oligomers as described herein.

1. Use of Modified Polynucleotide Oligomers in Array Applications

In some embodiments, modified polynucleotide oligomers are used in applications comprising an array. One of skill in the art is aware of numerous applications involving an array. As one of ordinary skill in the art will appreciate, the choice of an application involving an array to which a modified polynucleotide oligomer of the present invention is attached, can vary and is not limited to the disclosure herein.

In some embodiments, an array application is e.g., for hybridization or array-based analysis of gene expression. Exemplary non-limiting arrays include chip or platform arrays, bead arrays, liquid phase arrays, "zip-code" arrays and the like. The superior stability of the modified polynucleotide oligomers in base pairing with target nucleotide sequences results in improved discrimination of related sequences, in particular at the single-nucleotide level which is advantageous in hybridization or array-based analysis. Materials suitable for construction of arrays such as nitrocellulose, glass, silicon wafers, optical fibers, etc. are known to those of skill in the art.

Thus, in some embodiments of the present invention, an array is provided to which a modified polynucleotide oligomer is attached. In some embodiments of the present invention, an array is provided to which a plurality of modified polynucleotide oligomers are attached. In some embodiments of the present invention, an array is provided to which a plurality of different modified polynucleotide oligomers are attached. The plurality of different modified polynucleotide oligomers may comprise different further modifications of the modified polynucleotide oligomers or modified polynucleotide oligomers having different sequences.

2. Use of Modified Polynucleotide Oligomers as Probes

In some embodiments, a modified polynucleotide oligomer is a probe. In some embodiments, the probe comprises a detectable label or moiety. A detectable label, as used herein, includes both directly detectable moieties, such as fluorescent dyes (fluorophores), and indirectly detectable moieties, such as members of binding pairs. When the detectable moiety is a member of a binding pair, in some embodiments, the probe can be detectable by incubating the probe with a detectable label bound to the second member of the binding pair. In some embodiments, a probe is not labeled, such as when a probe is a capture probe, e.g., on a microarray or bead. In some embodiments, a probe is not extendable, e.g., by a polymerase. In some embodiments, a probe is extendable.

In some embodiments, a modified polynucleotide oligomer is a FRET probe. A FRET probe may be labeled at the 5'-end with a fluorescent dye and at the 3'-end with a fluorescence quencher, a chemical group that absorbs (i.e., suppresses) fluorescence emission from the dye when the groups are in close proximity (i.e., attached to the same probe).

In some embodiments, a modified polynucleotide oligomer is a 5' nuclease PCR probe, a Molecular Beacon™, or a Scorpion™ probe.

3. Use of Modified Polynucleotide Oligomers in Hybridization Methods

Hybridization of oligomers and nucleic acids to complementary modified polynucleotide oligomers are useful in a wide variety of applications as will be understood by a person of ordinary skill in the art. For example, the formation of a hybridized duplex comprising a modified polynucleotide oligomer of the invention can be detected directly as the result of a change in a detectable signal or characteristic of the duplex, as in fluorescence in situ hybridization (FISH) techniques, for example. A modified polynucleotide oligomer of the invention may thus be provided as an unlabeled or labeled probe to facilitate such detection. The duplex may also be subjected to a solid phase or electrophoretic separation, for example, to distinguish true signal from background. In some embodiments, a hybridized modified polynucleotide oligomer is chemically altered in some way as a result of hybridizing to a complementary target sequence. For example, in a primer extension process, such as PCR, a modified polynucleotide oligomer may be referred to as a "modified primer." Such modified primer can be extended to form a primer extension product that may serve as a template for the next PCR cycle. In a 5'-nuclease reaction, a modified polynucleotide oligomer, may be referred to as a "modified oligomer probe." Such modified oligomer probe can be cleaved by an exonuclease activity of a DNA polymerase, such as Taq polymerase, to produce cleaved fragments that can be detected by fluorescence or other means. In such applications, the extension of a primer or cleavage of a probe is evidence that a modified polynucleotide oligomer of the invention formed a duplex by hybridization with a complementary nucleic acid sequence. Furthermore, reaction conditions can be adjusted to determine the most suitable conditions for maximizing hybridization for a particular application. In particular, reaction temperatures are typically chosen to be near, slightly below, or sometimes slightly above, the $T_m$ of the oligomer for its target. If the reaction temperature is too high, the oligomer will not hybridize to its target sequence, and the efficiency of primer extension or probe cleavage will be reduced.

The present invention also provides methods of using a polynucleotide oligomer comprising a modified cytosine base of the present invention (also referred to herein as a "modified polynucleotide oligomer") in methods for hybridization. Any of the modified cytosine bases described herein may be used in a method for hybridization. In some embodiments of the present invention a method for hybridization of a polynucleotide oligomer comprising a modified cytosine base with a nucleic acid target sequence suspected of being present in a reaction mixture, is provided. In some embodiments, this method comprises the steps of incubating a reaction mixture comprising the modified polynucleotide oligomer and suspected of comprising a target nucleic acid sequence under conditions favorable for hybridization of the modified polynucleotide oligomer to the target nucleic acid sequence if present in the reaction mixture. The modified polynucleotide oligomer used in that method is complementary to a sequence within the nucleic acid target sequence suspected to be present in the reaction mixture and comprises at least one modified base represented by the formula:

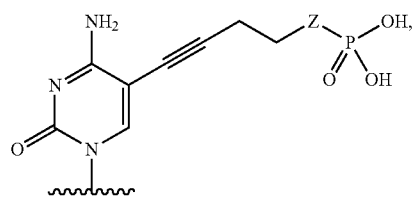

wherein Z is $CH_2$ or O.

In a particular embodiment of the present invention, the modified polynucleotide oligomer used in that method is complementary to a sequence within the nucleic acid target sequence suspected to be present in the reaction mixture and comprises at least one modified base represented by the formula:

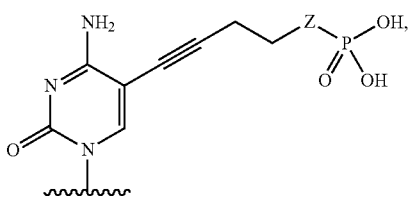

wherein Z is O.

The reaction mixture is incubated, thereby forming a duplex between the modified polynucleotide oligomer and the target nucleic acid sequence if present in the reaction mixture. In some embodiments, the method comprises the step of detecting the presence or confirming the absence of the target nucleic acid sequence in the reaction mixture. The presence of the target nucleic acid sequence in the reaction mixture is detected as a result of the formation of such duplex. The absence of the target nucleic acid sequence in the reaction mixture is confirmed as a result of the non-formation of such duplex. In some embodiments of the method, the modified polynucleotide oligomer comprises a moiety selected from the group consisting of a detectable label, a fluorophore and a fluorescence quencher. A detectable label, fluorophore and/or fluorescence quencher facilitates detection of the duplex and/or of the target nucleic acid sequence.

In some embodiments, the reaction mixture comprises a biological sample. In some embodiments the reaction mixture comprises a nucleic acid sample prepared from a biological sample. Preparing a nucleic acid sample from a biological sample is well known in the art.

The present invention provides methods of detecting a target nucleic acid in a biological sample. In some embodiments, this method comprises the steps of (a) contacting a target nucleic acid of the biological sample with a modified polynucleotide oligomer comprising a modified cytosine base, wherein the target nucleic acid specifically hybridizes to the modified polynucleotide oligomer and (b) detecting duplex formation between the target nucleic acid and the modified polynucleotide oligomer.

In some embodiments, the present invention provides a method comprising the steps of (a) providing a nucleic acid sample suspected of containing a target nucleic acid (b) providing a modified polynucleotide oligomer comprising a modified cytosine base and a nucleotide sequence complementary to the target nucleic acid, and (c) combining the nucleic acid sample and the modified polynucleotide oligomer under hybridization conditions that permit duplex formation between the target nucleic acid and the modified polynucleotide oligomer.

In some embodiments, the present invention provides a method comprising the steps of (a) combining (i) a nucleic acid sample suspected of containing a target nucleic acid and (ii) a modified polynucleotide oligomer comprising a modified cytosine base and a nucleotide sequence complementary to the target nucleic acid under hybridization conditions that permit duplex formation between the target nucleic acid and the modified polynucleotide oligomer and (b) detecting duplex formation between the target nucleic acid and the modified polynucleotide oligomer.

In some embodiments, the present invention provides a method comprising the steps of (a) combining (i) a nucleic acid sample suspected of containing a target nucleic acid and (ii) a modified polynucleotide oligomer comprising a modified cytosine base and a nucleotide sequence complementary to the target nucleic acid under hybridization conditions that permit duplex formation between the target nucleic acid and the modified polynucleotide oligomer and (b) confirming absence of the target nucleic acid in the nucleic acid sample.

As one of ordinary skill in the art will appreciate methods of hybridization and detection the presence or confirming the absence of target nucleic acids in a sample can be performed with any target nucleic acid as long as some information of the target is available so that a modified polynucleotide oligomer can be prepared that has at least four contiguous complementary nucleotides to the target nucleic acid.

4. Use of Modified Polynucleotide Oligomers as Primers

In some embodiments, a modified polynucleotide oligomer is a primer. A primer, as used herein and sometimes referred to as modified primer, is a modified polynucleotide oligomer that is capable of specifically hybridizing to a target sequence and of being extended at one end, usually a 3'-end, by a template-dependent DNA or RNA polymerase. In the presence of a template, a polymerase and suitable buffers and reagents, the modified primer can be extended to form a modified primer extension product (also referred to as an extended primer) that is complementary to the target sequence. In some embodiments, the modified primer comprises a label, or one or more of the precursors for polymerization (e.g., nucleoside triphosphates) can comprise a label. Modified primer extension product(s) can be detected by any of a number of techniques known to those of skill in the art. In some embodiments, the modified primer is not labeled. In some embodiments, a modified polynucleotide oligomer is used as a primer for amplification.

5. Use of Modified Polynucleotide Oligomers for Amplification

In some embodiments, a modified polynucleotide oligomer is used in amplification reactions. As one of ordinary skill in the art will appreciate amplification reactions in which a modified polynucleotide oligomer of the present invention can be used, are not limited. Exemplary, non-limiting examples of amplifications include polymerase chain reaction ("PCR"), reverse-transcriptase PCR, real-time PCR, nested PCR, multiplex PCR, quantitative PCR (Q-PCR), nucleic acid sequence based amplification (NASBA), transcription mediated amplification (TMA), ligase chain reaction (LCR), rolling circle amplification (RCA), or strand displacement amplification (SDA). Thus, in some embodiments, a method for amplification is provided. In some embodiments this method comprises the steps of (a) annealing a modified polynucleotide primer to a target sequence and (b) extending the modified polynucleotide oligomer to form a modified polynucleotide oligomer extension product.

In some embodiments of the method for amplification, the modified polynucleotide oligomer is attached to a solid support. In some embodiments of the method for amplification, the modified polynucleotide oligomer is attached to a bead. In some embodiments of the method for amplification, the modified polynucleotide oligomer is attached to an array. In some embodiments of the method for amplification, the modified polynucleotide oligomer is attached to a microarray.

Many amplification reactions, such as PCR, utilize reiterative primer-dependent polymerization. In some embodiments, a modified polynucleotide oligomer is a primer that is capable of hybridizing to a target nucleic acid sequence and once hybridized, is capable of being extended by a polymerizing enzyme (in the presence of nucleotide substrates, such as nucleotide triphosphates), using the target nucleic acid sequence as a template. Polymerizing enzymes include, but are not limited to, DNA and RNA polymerases, reverse transcriptases, etc. Conditions favorable for polymerization by different polymerizing enzymes are well-known to those of skill in the art.

The amplification reaction is preferably carried out in an automated thermal cycler to facilitate incubation times at desired temperatures. In some embodiments, amplification comprises at least one cycle of the sequential procedures of: annealing at least one primer (i.e., a modified polynucleotide oligomer) with a complementary or substantially complementary sequence in at least one target nucleic acid; synthesizing at least one strand of nucleotides in a template-dependent manner using a polymerase; and denaturing the newly-formed nucleic acid duplex to separate the strands. The cycle may or may not be repeated. Amplification can comprise thermocycling or can be performed isothermally.

In some embodiments, amplification comprises an initial denaturation at about 90° C. to about 100° C. for about 1 to about 10 minutes, followed by cycling that comprises annealing at about 55° C. to about 75° C. for about 1 to about 30 seconds, extension at about 55° C. to about 75° C. for about 5 to about 60 seconds, and denaturation at about 90° C. to about 100° C. for about 1 to about 30 seconds. Other times and profiles may also be used. For example, primer annealing and extension may be performed in the same step at a single temperature.

In some embodiments, the cycle is carried out at least 5 times, at least 10 times, at least 15 times, at least 20 times, at least 25 times, at least 30 times, at least 35 times, at least 40 times, or at least 45 times.

The particular cycle times and temperatures will depend on the particular nucleic acid sequence being amplified and can readily be determined by a person of ordinary skill in the art.

6. Use of Modified Polynucleotide Oligomers in Therapeutic Applications

In some embodiments, a modified polynucleotide oligomer finds utility in therapeutic applications. As one of ordinary skill in the art will appreciate therapeutic applications in which a modified polynucleotide oligomer of the present invention can be used, are not limited. Exemplary, non-limiting examples of therapeutic applications include use of a modified polynucleotide as an antisense oligomer or siRNA that binds to RNA, use of a modified polynucleotide as an antisense oligonucleotide that binds to DNA, use of a modified polynucleotide as an aptamer, use of a modified polynucleotide as a decoy, or use of a modified polynucleotide as a CpG oligomer that binds to proteins. Modified polynucleotide oligomers can been used to regulate gene expression and in antisense gene therapy.

IV. Kits

For use in diagnostic, research, and therapeutic applications suggested above, kits are also provided by the invention. In the diagnostic and research applications such kits may include any or all of the following: one or more modified cytosine bases, one or more modified polynucleotide oligomers comprising a modified cytosine base, one or more modified nucleosides comprising a modified cytosine base, one or more modified nucleotides comprising a modified cytosine base, one or more modified PNA comprising a modified cytosine base; one or more modifier moieties comprising a modified cytosine base, one or more assay reagents, one or more buffers, and the like. A therapeutic product may include sterile saline or another pharmaceutically acceptable emulsion and suspension base. Optionally, the kit includes an instruction manual describing the making and/or using of a modified moiety as described herein. Typically, these components, other than the instruction manual, are provided in one or more containers.

In some embodiments, the invention provides a kit comprising a modified moiety as described herein. In some embodiments, the invention provides a kit comprising a modified polynucleotide oligomer as described herein. In some embodiments, a kit further comprises at least one polymerase, such as a thermostable polymerase enzyme. In some embodiments, a kit further comprises dNTPs. In some embodiments, a kit further comprises a primer and/or a probe.

In some embodiments, the present invention provides kits comprising compositions for practicing methods of the present invention, including, but not limited to, processing a nucleic acid sample, performing an enzymatic reaction, performing a hybridization, forming a duplex, etc. as described herein.

An instructional material may contain directions (i.e., protocols) for the practice of the methods of this invention. The instructions may be present in the subject kits in a variety of forms, one or more of which may be present in the kit. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

As one of ordinary skill in the art will appreciate, a wide variety of kits and components can be prepared according to the present invention, depending upon the intended user of the kit and the particular needs of the user. Additional kit embodiments of the present invention include optional functional components that would allow one of ordinary skill in the art to perform any of the method variations described herein.

Preferred embodiments of this invention are described herein, including the best mode known to the inventors for carrying out the invention. Of course, variations, changes, modifications and substitution of equivalents on those preferred embodiments will become apparent to those of ordinary skill in the art upon reading the foregoing description. The inventors expect skilled artisans to employ such variations, changes, modifications and substitution of equivalents as appropriate, and the inventors intend for the invention to be practiced otherwise than specifically described herein. Those of skill in the art will readily recognize a variety of non-critical parameters that could be changed, altered or modified to yield essentially similar results. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

The referenced patents, patent applications, and scientific literature referred to herein are hereby incorporated by reference in their entirety as if each individual publication, patent or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As can be appreciated from the disclosure above, the present invention has a wide variety of applications. The invention is further illustrated by the following examples, which are only illustrative and are not intended to limit the definition and scope of the invention in any way.

V. EXAMPLES

General Methods and Recommendations

The following examples are provided to illustrate, but not limit, the invention described herein.

All air and moisture sensitive reactions were carried out under argon (Ar). Anhydrous solvents and reagents were obtained from commercial sources unless otherwise noted. Flash chromatography was performed on 230-400 mesh silica gel (VWR).

$^1$H NMR spectra were run at 20° C. on a Bruker 400 spectrometer and reported in ppm relative to standards Me$_4$Si for $^1$H and H$_3$PO$_4$ for $^{31}$P.

Melting points were determined using a Mel-Temp melting point apparatus in open capillary and are uncorrected.

UV-visible absorption spectra were recorded in the 200-400-nm range on a Cary Varian spectrophotometer.

Thin-layer chromatography was performed on silica gel 60 F-254 aluminum-backed TLC plates (EM Reagents).

HPLC analyses were done on an Agilent 1100 instrument equipped with a quaternary pump, autosampler, and diode array detector, and, unless otherwise noted, absorbance at 270 nm was monitored.

Oligonucleotide synthesis was performed on a MerMade 12 DNA Synthesizer (BioAutomation). Standard phosphoramidite synthesis cycles were used, and coupling time was increased to 360 seconds for modified phosphoramidites. For all melting experiments, the concentration of each oligonucleotide was 1 uM, and the buffer content was 3 mM MgCl$_2$, 15 mM KCl, 25 mM HEPES, pH 8. Cleavage from the solid support and deprotection were carried out in concentrated aqueous ammonia at RT for 24 hrs.

The practice of the present invention will employ, unless otherwise indicated herein, conventional techniques of cell biology, molecular biology, microbiology, virology, recombinant DNA, and so forth which are within the skill of the art. Such techniques are explained fully in the literature. See e.g., Sambrook, Fritsch, and Maniatis, *Molecular Cloning: A Laboratory Manual*, Second Edition (1989), *Oligonucleotide Synthesis* (M. J. Gait Ed., 1984), *Animal Cell Culture* (R. I. Freshney, Ed., 1987), the series *Methods In Enzymology* (Academic Press, Inc.); *Gene Transfer Vectors For Mammalian Cells* (J. M. Miller and M. P. Calos eds. 1987), *Current Protocols Ii Molecular Biology* (F. M. Ausubel, R. Brent, R. E. Kingston, D. D. Moore, J. G. Siedman, J. A. Smith, and K. Struhl, eds., 1987).

In the following specific examples, the relevant reaction schemes follow the examples.

Example 1

Synthesis of DMT-C$^{BP}$ Phosphoramidite (M6)

Example 1 describes a synthetic procedure for preparing a protected form of a modified cytosine 3'-phosphoramidite monomer M6, which comprises a protected phosphate moiety linked to the pyrimidine 5-carbon by a 1-butynyl linker (the modified base is sometimes designated herein as "C$^{BP}$"). The 5'-hydroxyl of M6 is protected by a DMT group, and the two hydroxyl groups of the phosphate moiety are protected by pivaloyloxybenzyl groups.

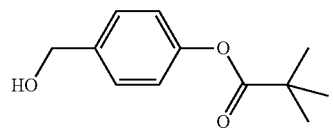

4-Pivaloyloxybenzyl alcohol (Compound M1).

To a stirred solution of 4-hydroxybenzyl alcohol (6.21 g, 50 mmol) in anhydrous THF (50 mL) containing triethylamine (10.43 mL, 75 mmol) pivaloyl chloride (6.79 mL, 55 mmol) was added drop wise at room temperature under argon atmosphere. After being stirred for 60 min, the reaction mixture was quenched with water (0.2 mL) and left overnight. It was then diluted with EtOAc (~400 mL) and washed with saturated NaHCO$_3$ (3×100 mL) and brine (100 mL). It was then dried over Na$_2$SO$_4$, filtered and concentrated. The product (TLC: R$_f$~0.4 in ethyl acetate/hexanes (4:6)) was isolated using flash chromatography on silica gel column (4×20 cm) eluting with ethyl acetate/hexanes (4:6). Pure fractions were pooled, concentrated and dried in vacuum to give 7.75 g (74%) of colorless oil. $^1$H NMR (DMSO-d$_6$): δ 7.35 (d, 2H, J=8.6 Hz), 7.04 (d, 2H, J=8.6 Hz), 5.22 (t, 1H), 4.50 (d, 2H), 1.31 (s, 9H).

Compound M2

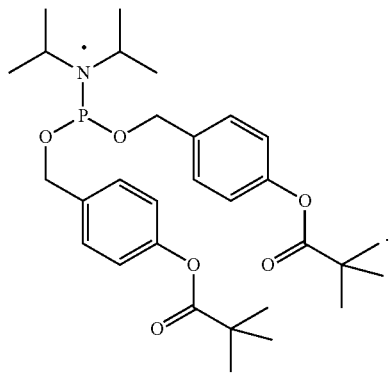

Compound M1 (see below; 7.79 g, 37.4 mmol) was dissolved in anhydrous THF (50 mL) containing N,N-diisopropylethylamine (8.14 mL, 46.8 mmol) under argon, and the resulting solution was chilled down to 0° C. in an ice-water bath. Diisopropylphosphoramidous dichloride (3.46 mL, 18.8 mmol) was added drop wise via syringe over a period of 5 minutes with stirring and cooling. The reaction mixture was allowed to warm up to room temperature and stirred overnight. Precipitated salts were removed by filtration, and the filtrate was concentrated in vacuum. The residue was dissolved in ethyl acetate (~150 mL) and washed with 5% NaHCO$_3$ (3×50 mL) followed by brine (50 mL). The organic layer was separated, dried over Na$_2$SO$_4$, filtered and concentrated. The product (TLC: $R_f$~0.6 in ethyl acetate/hexanes/triethylamine (20:80:2)) was isolated using flash chromatography on silica gel column (4×20 cm) loading from hexanes/triethylamine (100:2) and eluting with acetate/hexanes/triethylamine (20:80:2). Pure fractions were pooled and concentrated to give 8.1 g (79%) of colorless oil. $^1$H NMR (DMSO-d$_6$): δ 7.37 (d, 4H, J=8.6 Hz), 7.07 (d, 4H, J=8.6 Hz), 4.76-4.63 (m, 4H), 3.70-3.61 (m, 2H), 1.30 (s, 18H), 1.16 (d, 12H, J=6.8 Hz). $^{31}$P NMR (DMSO-d6): δ 147.30.

Compound M3

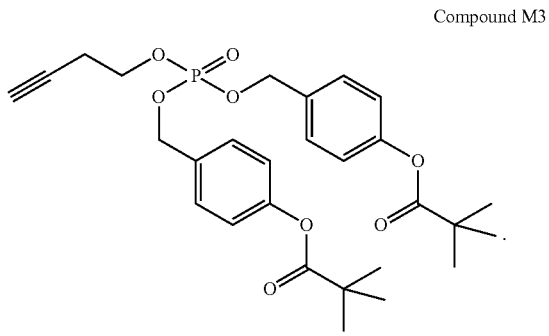 [SMILES: C#CCCOP(=O)(OCc1ccc(OC(=O)C(C)(C)C)cc1)OCc1ccc(OC(=O)C(C)(C)C)cc1]

3-Butyn-1-ol (1.18 mL, 15.0 mmol) and compound M2 (see below; 8.1 g, 14.8 mmol) were dissolved in anhydrous THF under argon atmosphere. A solution of 5-(ethylthio)-1H-tetrazole (66 mL, 0.25 M in acetonitrile) was added at once, and the reaction mixture was stirred for 1 h at room temperature. tert-Butyl hydroperoxide solution (4.0 mL, 5-6 M in decane) was added and the mixture was stirred for additional 2 hours. The solvents were then removed under vacuum, and the residue was dissolved in ethyl acetate (200 mL), washed with saturated NaHCO$_3$ (3×50 mL), and brine (50 mL). The organic phase was dried over Na$_2$SO$_4$, filtered and concentrated. The product (TLC: $R_f$~0.35 in ethyl acetate/hexanes (1:1)) was isolated by flash chromatography on silica gel using a step gradient 20-50% ethyl acetate in hexanes. Amorphous solid 5.3 g (67%) was obtained. $^1$H NMR (DMSO-d$_6$): δ 7.42 (d, 4H, J=8.6 Hz), 7.11 (d, 4H, J=8.6 Hz), 5.07 (d, 4H, J=8.2 Hz), 4.07-4.01 (m, 2H), 2.93 (t, 1H, J=2.6 Hz), 2.56-2.52 (m, 2H), 1.31 (s, 18H). $^{31}$P NMR (DMSO-d6): δ −1.2.

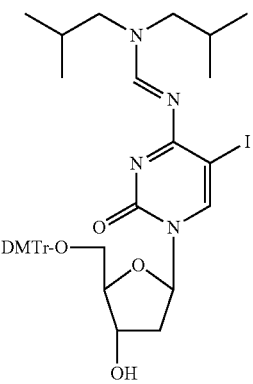

5'-DMT-N$^4$-DIBF-5-I-dC (Compound M4).

5-Iodo-2'-deoxycytidine (1.06 g, 3 mmol) was rendered anhydrous by co-evaporation with anhydrous pyridine (3×20 mL) and suspended in anhydrous MeOH (10 mL). N,N-Diisobutylformamide dimethylacetal (810 mg, 3.9 mmol) was added under argon atmosphere, and the reaction mixture was stirred at room temperature. The suspension turned into a clear solution within about an hour. At that point the HPLC analysis revealed complete disappearance of the starting nucleoside. The reaction mixture was quenched with water (0.1 mL) and the solvents were evaporated in vacuum. The residue was co-evaporated with anhydrous pyridine (3×20 mL), dissolved in anhydrous pyridine (20 mL) and treated with DMT-Cl as a solid. The mixture was stirred at room temperature overnight. Solvents were evaporated, the residue was treated with TEA:MeOH (10 mL, (1:10)) and evaporated again. The residue was dissolved in ethyl acetate (150 mL) and washed sequentially with 10% citric acid, 5% NaHCO$_3$, and brine.

The organic layer was separated, dried over Na$_2$SO$_4$, and filtered. The product (TLC: $R_f$~0.3 in ethyl acetate/acetone (8:2)) was isolated by flash chromatography eluting with a step gradient 0-20% acetone in ethyl acetate. White foam (1.81 g, 76%) was obtained. $^1$H NMR (DMSO-d$_6$): δ 8.63 (s, 1H), 8.14 (s, 1H), 7.42-7.20 (m, 9H), 6.92-6.89 (m, 4H), 6.11 (t, 1H), 5.29 (d, 1H), 4.23-4.18 (m, 1H), 3.96-3.93 (m, 1H), 3.74 (s, 6H), 3.45-3.41 (m, 2H), 3.33-3.29 (m, 2H), 3.22-3.19 (m, 2H), 2.32-1.93 (m, 4H), 0.93-0.85 (m, 12H).

Compound M5

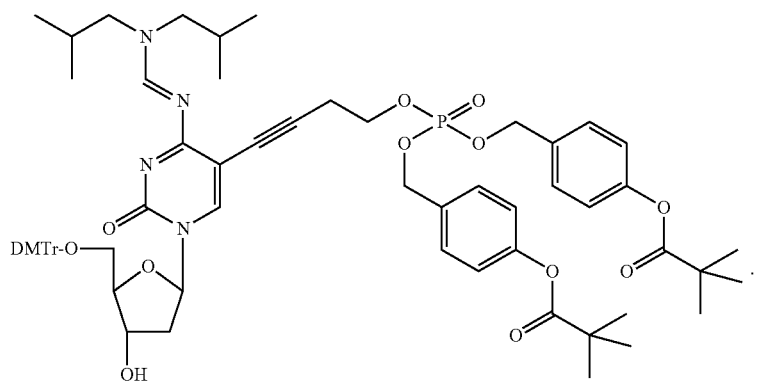

794 mg (1.0 mmol) of compound M4 (see above) and compound M3 (above; 637 mg, 1.2 mmol) were combined with Pd(PPh$_3$)$_4$ (116 mg, 0.1 mmol), copper(I) iodide (38 mg, 0.2 mmol) in a round bottom flask equipped with a magnetic stirring bar. The flask was evacuated and filled with argon gas, sealed with a septum and an argon balloon. N,N-Dimethylformamide (10 mL) and triethylamine (697 μL, 5 mmol) were added using syringe through the septum and the mixture was stirred at ambient temperature under Ar atmosphere. The progress of the reaction was controlled using C$_{18}$ RP HPLC or TLC monitoring the disappearance of the starting nucleoside. After 12 to 72 hours the reaction mixture was diluted with ethyl acetate (150 mL) and washed with 0.1 M Na$_2$EDTA (2×50 mL), saturated aqueous NaHCO$_3$ (3×50 mL), and brine (50 mL).

The organic layer was separated, dried over Na$_2$SO$_4$, and concentrated to oil. The reaction product (TLC: R$_f$~0.35 in ethyl acetate/acetone (8:2)) was isolated by flash chromatography on silica gel column (3×20 cm) loading from ethyl acetate and eluting with a step gradient 0-20% acetone in ethyl acetate. Yellowish glassy solid was obtained (834 mg, 70%). $^1$H NMR (DMSO-d$_6$): δ 8.61 (s, 1H), 8.04 (s, 1H), 7.42-7.18 (m, 13H), 7.08-7.04 (m, 4H), 6.91-6.86 (m, 4H), 6.12 (t, 1H), 5.33 (d, 1H), 5.03 (d, 4H), 4.31-4.26 (m, 4H), 3.99-3.89 (m, 3H), 3.71 (s, 6H), 3.33-3.22 (m, 5H), 3.13-3.09 (m, 1H), 2.57-2.52 (m, 2H), 2.33-2.07 (m, 3H), 1.96-1.86 (m, 1H), 1.29 (s, 18H), 0.84 (d, 12H). $^{31}$P NMR (DMSO-d6): δ −1.3.

triethylamine (100:2). Creamy foam (803 mg, 85%) was obtained. $^{31}$P NMR (DMSO-d6): δ 147.47, 147.23, −1.29.

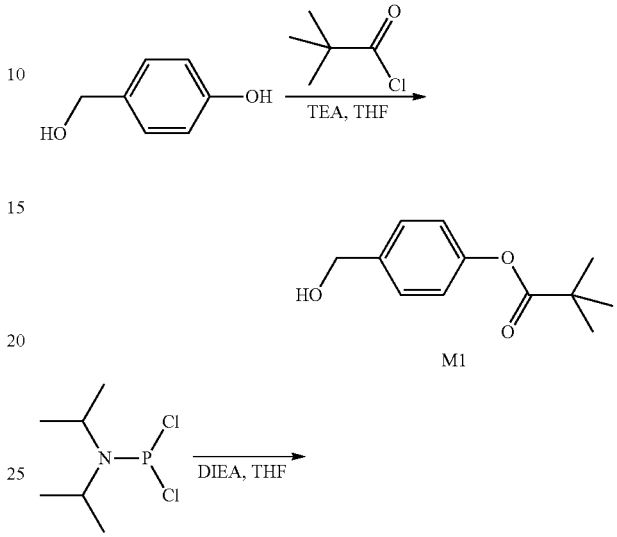

M1

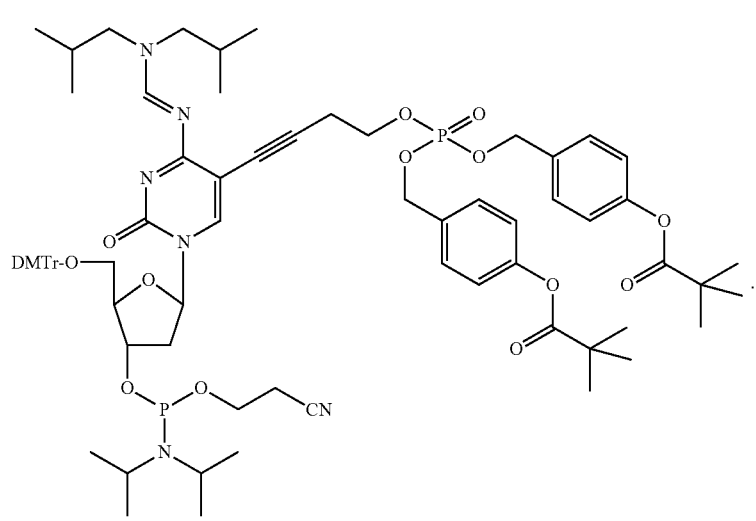

Compound M6

To a stirred solution of compound M5 (above; 814 mg) in anhydrous CH$_2$Cl$_2$ (10 mL) containing N,N-diisopropylethylamine (348 μL, 2.0 mmol) kept at 0° C. 2-cyanoethyl N,N-diisopropylchlorophosphoramidite (159 μL, 0.71 mmol) was added dropwise under argon. The reaction mixture was allowed to warm up to room temperature and methanol (0.1 mL) was added after 30 min. The reaction mixture was diluted with ethyl acetate (150 mL) and washed with 5% aqueous NaHCO$_3$ (3×50 mL), and brine (50 mL). The organic layer was separated, dried over Na$_2$SO$_4$, and concentrated to oil. The product was purified using flash chromatography on silica gel column (3×15 cm) loading from ethyl acetate/hexanes/triethylamine (50:50:2) and eluting with a step gradient 50-100% ethyl acetate in hexane/

-continued

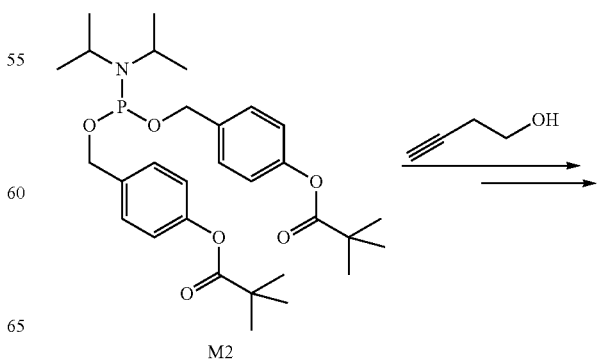

M2

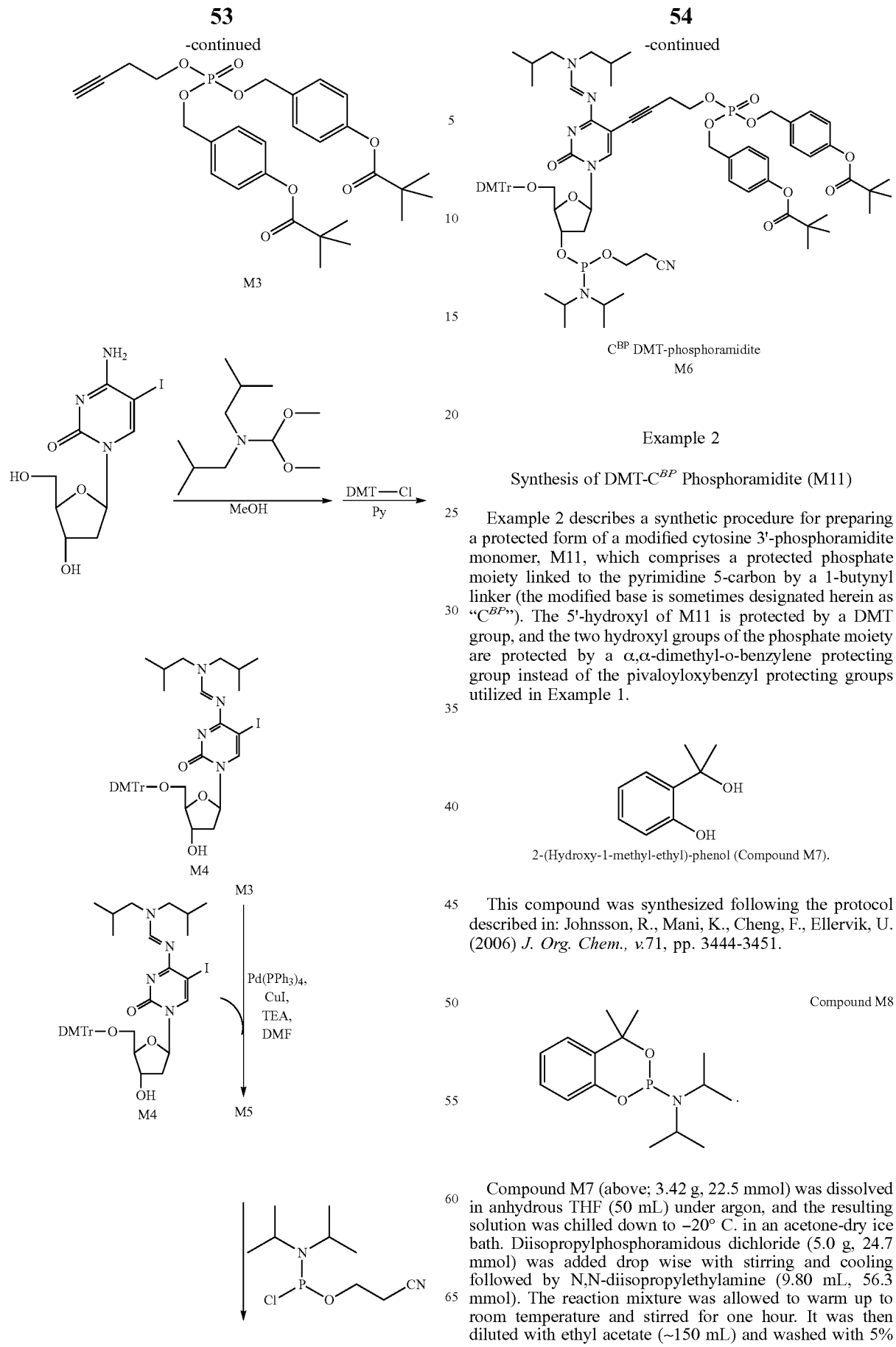

Example 2

Synthesis of DMT-C$^{BP}$ Phosphoramidite (M11)

Example 2 describes a synthetic procedure for preparing a protected form of a modified cytosine 3'-phosphoramidite monomer, M11, which comprises a protected phosphate moiety linked to the pyrimidine 5-carbon by a 1-butynyl linker (the modified base is sometimes designated herein as "C$^{BP}$"). The 5'-hydroxyl of M11 is protected by a DMT group, and the two hydroxyl groups of the phosphate moiety are protected by a α,α-dimethyl-o-benzylene protecting group instead of the pivaloyloxybenzyl protecting groups utilized in Example 1.

This compound was synthesized following the protocol described in: Johnsson, R., Mani, K., Cheng, F., Ellervik, U. (2006) *J. Org. Chem.*, v.71, pp. 3444-3451.

Compound M7 (above; 3.42 g, 22.5 mmol) was dissolved in anhydrous THF (50 mL) under argon, and the resulting solution was chilled down to −20° C. in an acetone-dry ice bath. Diisopropylphosphoramidous dichloride (5.0 g, 24.7 mmol) was added drop wise with stirring and cooling followed by N,N-diisopropylethylamine (9.80 mL, 56.3 mmol). The reaction mixture was allowed to warm up to room temperature and stirred for one hour. It was then diluted with ethyl acetate (~150 mL) and washed with 5%

NaHCO₃ (3×50 mL) followed by brine (50 mL). The organic layer was separated, dried over Na₂SO₄, filtered and concentrated. The product (TLC: R$_f$~0.85 in hexanes/triethylamine (100:2)) was isolated using flash chromatography on silica gel column (4×20 cm) eluting with hexanes/triethylamine (100:2). Pure fractions were pooled and concentrated to give 5.58 g (88%) of colorless oil which solidified upon storage at −20° C. ¹H NMR (DMSO-d₆): δ7.23-7.13 (m, 2H), 6.97-6.82 (m, 2H), 3.67-3.54 (m, 2H), 1.69 (s, 3H), 1.56 (s, 3H), 1.19-1.14 (m, 12H). ³¹P NMR (DMSO-d6): δ 130.75.

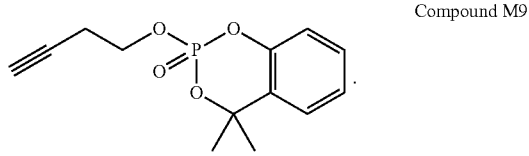 [SMILES: C#CCCOP1(=O)Oc2ccccc2C(C)(C)O1]

Compound M9

3-Butyn-1-ol (1.50 mL, 18.9 mmol) and compound M8 (5.58 g, 19.8 mmol) were dissolved in anhydrous acetonitrile (50 mL) under argon atmosphere. A solution of 5-(ethylthio)-1H-tetrazole (87 mL, 0.25 M in acetonitrile) was added at once, and the reaction mixture was stirred for 1 h at room temperature. tert-Butyl hydroperoxide solution (5.0 mL, 5-6 M in decane) was added and the mixture was stirred for additional 2 hours. The solvents were then removed under vacuum, and the residue was dissolved in ethyl acetate (200 mL), washed with saturated NaHCO₃ (3×50 mL), and brine (50 mL). The organic phase was dried over Na₂SO₄, filtered and concentrated. The product (TLC: R$_f$~0.33 in ethyl acetate/hexanes (1:1)) was isolated by flash chromatography on silica gel using a step gradient 30-50% ethyl acetate in hexanes. Colorless oil 4.79 g (91%) was obtained. ¹H NMR (DMSO-d₆): δ 7.45-7.35 (m, 2H), 7.25-7.13 (m, 2H), 4.13-4.05 (m, 2H), 2.85 (t, 1H, J=2.7 Hz), 2.55-2.49 (m, 2H), 1.79 (s, 3H), 1.73 (s, 3H). ³¹P NMR (DMSO-d6): δ −12.45.

(Compound M10)

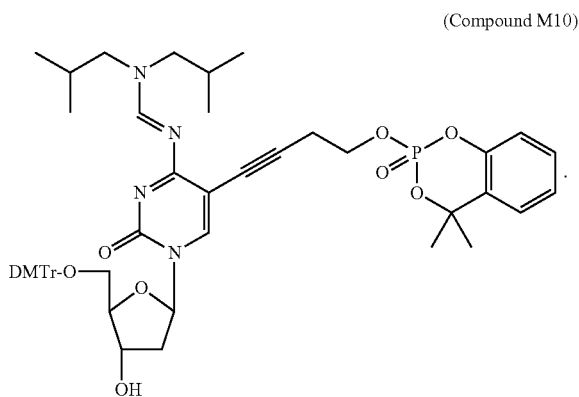

This compound was synthesized following the procedure described for compound M5 starting with 2.38 g (3.0 mmol) of compound M4 and compound M9 (1.04 g, 3.9 mmol). The reaction product (TLC: R$_f$~0.3 in ethyl acetate/acetone (8:2)) was isolated by flash chromatography on silica gel column (4×20 cm) loading from ethyl acetate and eluting with a step gradient 0-20% acetone in ethyl acetate. Brownish foam was obtained (2.27 g, 81%). ¹H NMR (DMSO-d₆): δ 8.62 (s, 1H), 8.00 (s, 1H), 7.42-7.03 (m, 13H), 6.91-6.86 (m, 4H), 6.12 (t, 1H), 5.34 (d, 1H), 4.30-4.25 (m, 1H), 3.99-3.90 (m, 3H), 3.71 (s, 6H), 3.34-3.22 (m, 5H), 3.14-3.09 (m, 1H), 2.56-2.50 (m, 4H), 2.33-2.08 (m, 3H), 1.97-1.90 (m, 1H), 1.72 (s, 3H), 1.69 (s, 3H), 0.89-0.81 (m, 12H). ³¹P NMR (DMSO-d6): δ −12.57.

Compound M11

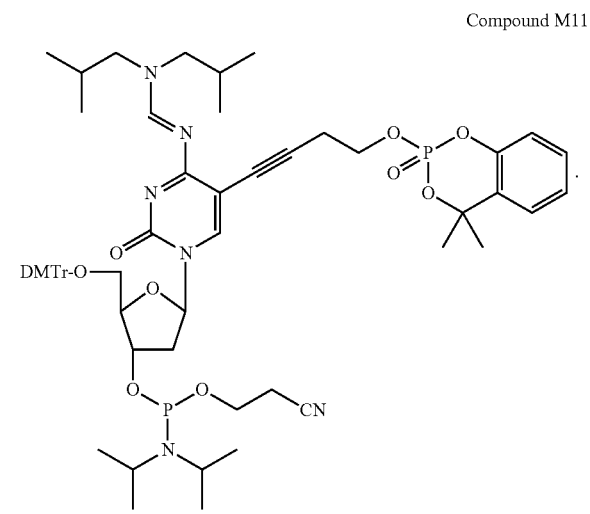

Phosphoramidite compound M11 was synthesized following the procedure described for compound M6 starting with 2.24 g (2.4 mmol) of compound M10. The product was purified using flash chromatography on silica gel column (4×20 cm) loading from ethyl acetate/hexanes/triethylamine (60:40:2) and eluting with a step gradient 60-100% ethyl acetate in hexane/triethylamine (100:2). Creamy foam was obtained (2.38 g, 87%) was obtained. ³¹P NMR (DMSO-d6): δ 147.44, 147.15, −12.58.

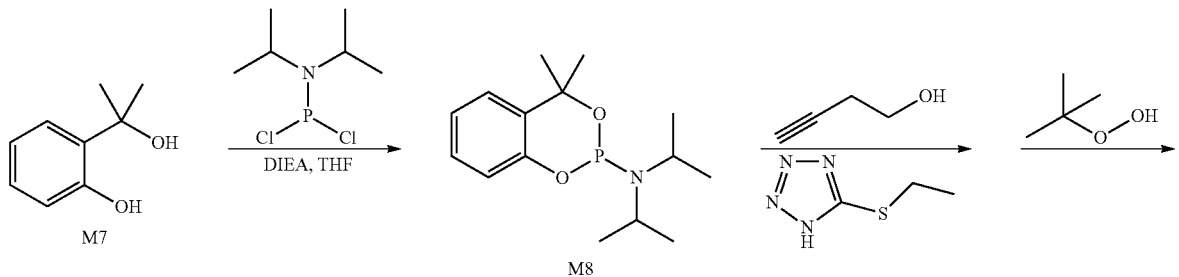

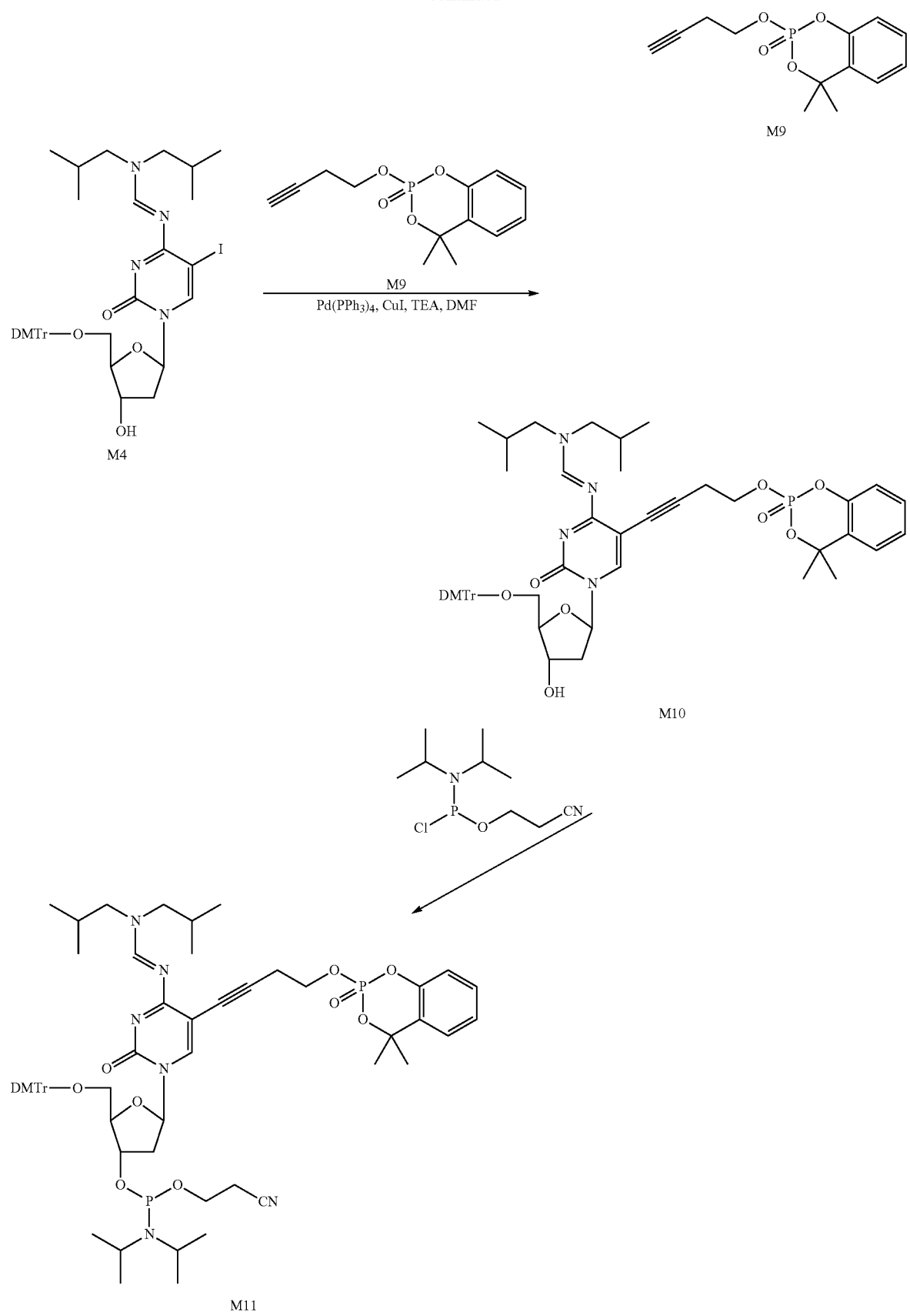

Example 3

Synthesis of C$^{BP}$-PNA (M18)

Example 3 describes a synthetic procedure for preparing a protected form of a modified cytosine PNA monomer, M18, which comprises a C$^{BP}$ moiety linked to a PNA monomer backbone. The monomer comprises a phosphate moiety that is protected by an α,α-dimethyl-o-benzylene protecting group, an Fmoc-protected amino group, and a free carboxlylic acid group for incorporation into a polynucleotide oligomer by PNA peptide coupling methods.

Compound M12

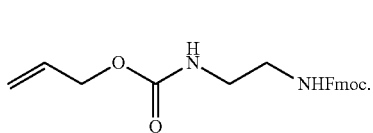

Compound M12 was prepared according to the literature procedure (*J. Org. Chem.*, 2008, 73, p. 3807-3816).

Compound M13

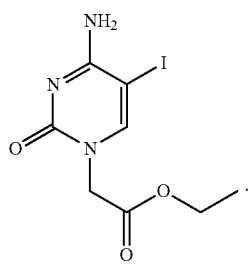

5-Iodocytosine (5.10 g, 21.5 mmol) was dissolved in 125 mL of anhydrous DMF under argon, and the solution was cooled to 0° C., then NaH (95%, 0.544 g, 21.5 mmol) was added. After 1 hour of stirring at ambient temperature, the solution became clear, and after 4 hr precipitate formed. Ethyl bromoacetate (2.38 mL, 21.5 mmol) was added drop wise over 2 min, and the reaction mixture was allowed to proceed at ambient temperature overnight. Solvent was removed by rotary evaporation under high vacuum, and to the residual oil 100 mL of water was added. The solidified residue was collected by filtration, dried, and recrystallized from ethanol to yield 5.19 g (75%) of the product. $^1$H NMR (DMSO-d$_6$): δ 1.18 (t, 3H), 4.12 (q, 2H), 4.44 (s, 2H), 6.65 (s, 1H), 7.83 (s, 1H), 8.09 (s, 1H).

Compound M14

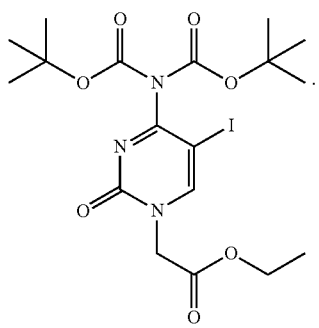

Compound M13 (above; 5.11 g, 15.8 mmol) was suspended in 250 mL of anhydrous THF, and DMAP (193 mg, 1.6 mmol), triethylamine (4.40 mL, 31.6 mmol), Boc$_2$O (7.59 g, 34.8 mmol) were added to the solution. After 6 hours of stirring at ambient temperature, additional 1.5 g of Boc$_2$O was added, the reaction mixture was heated to 60° C. for 2 hr, and then allowed to stir overnight at ambient temperature. Solvents were removed by evaporation under vacuum, and the reaction product was isolated by flash chromatography on silica gel column (5×18 cm) eluting with a step gradient 30-50% ethyl acetate in hexanes to yield 5.49 g (66%). $^1$H NMR (DMSO-d$_6$): δ 1.21 (t, 3H), 1.42 (s, 18H), 4.18 (q, 2H), 4.72 (s, 2H), 8.69 (s, 1H).

Compound M15

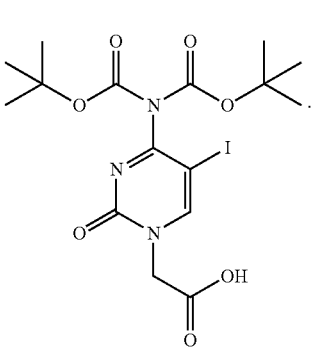

Compound M14 (above; 5.46 g, 10.4 mmol) was dissolved in 90 mL of THF and cooled to 0° C. 30 mL of 2.5 M NaOH solution was added drop wise via an addition funnel over 20 min to the stirring THF solution. After 45 min, the reaction mixture was poured into a separatory funnel containing 150 mL of 1M NaHSO$_4$ and 150 mL of ethyl acetate. The mixture was shaken, and the organic layer was separated. The aqueous layer was extracted with ethyl acetate (2×100 mL), and the combined organic layers were dried over Na$_2$SO$_4$. The solvent was removed under vacuum, and the residue (5.54 g) was used in the next step without further purification or characterization.

Compound M16

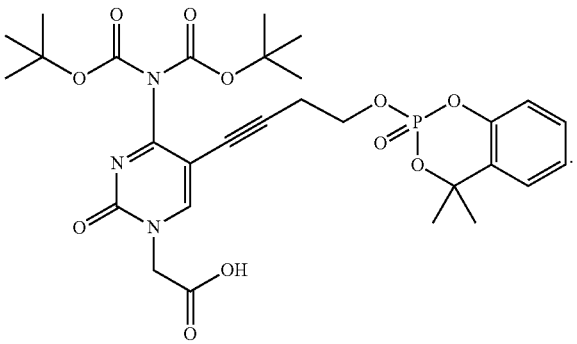

Compound M15 from the previous step (10.4 mmol) and compound M9 (above; 2.77 g, 10.4 mmol) were dissolved in 100 mL of anhydrous DMSO under argon in a round-bottomed flask equipped with a magnetic stirring bar, and Pd(PPh$_3$)$_4$ (1.12 g, 1.04 mmol), copper(I) iodide (199 mg, 1.04 mmol) and triethylamine (7.5 mL, 52 mmol) were added. The solution was heated to 65° C. and stirred at 65°

C. for 4 hr. The reaction mixture was diluted with dichloromethane (300 mL), stirred at ambient temperature for 30 min under air, and then the mixture was washed with water (300 mL), 0.1 M Na$_2$EDTA (2×250 mL), water (250 mL), and brine (250 mL). The organic layer was separated, dried over Na$_2$SO$_4$, filtered and concentrated to oil. The reaction product was isolated by flash chromatography on silica gel column (7×18 cm) eluting with a step gradient 1-4% water in acetonitrile to yield 3.97 g, (60% for 2 steps). $^1$H NMR (DMSO-d$_6$): δ 1.37 (s, 9H), 1.42 (s, 9H), 1.73 (s, 3H), 1.79 (s, 3H), 4.05-4.12 (m, 4H), 4.63 (d, 2H), 7.12-7.44 (m, 5H).

chromatography on silica gel column (5×18 cm) eluting with a step gradient 1-4% methanol in dichloromethane to yield 1.32 g, (48%). $^1$H NMR (DMSO-d$_6$): δ 1.39 (s, 18H), 1.72 (s, 3H), 1.77 (s, 3H), 2.72 (t, 2H), 3.18-3.49 (m, 4H), 4.09-4.42 (m, 5H), 4.59-4.97 (m, 5H), 5.19-5.33 (m, 2H), 5.8-6.1 (m, 1H), 7.12-7.20 (m. 2H), 7.31-7.43 (m, 7H), 7.64-7.74 (m, 3H), 7.88-7.90 (m, 2H).

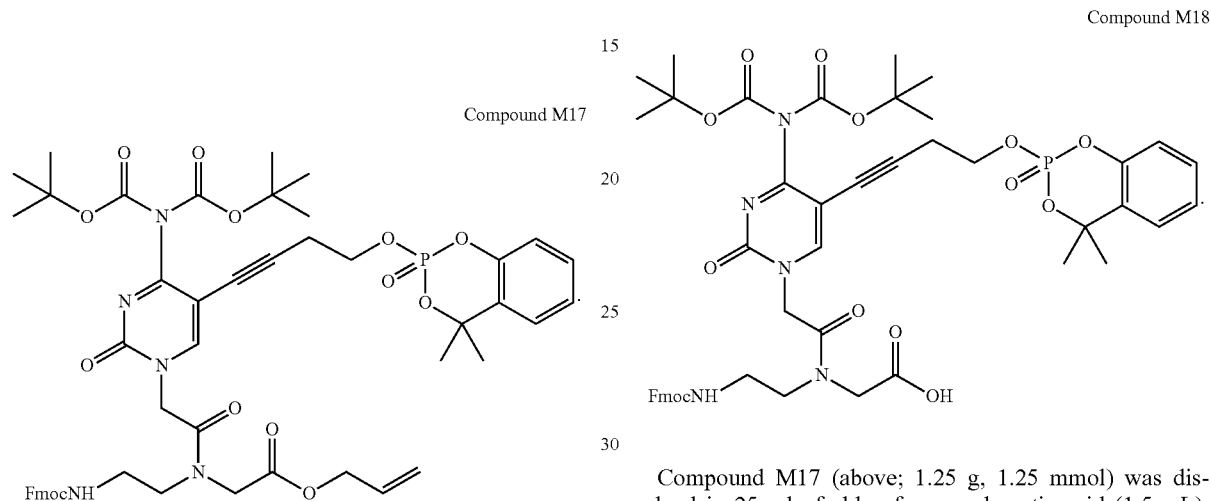

Compound M16 (above; 1.91 g, 3.0 mmol) and Compound M12 (above; 1.05 g, 2.7 mmol) were dissolved in 40 mL of anhydrous DMF under argon, and the resulting solution was cooled to 0° C. DIEA (1.60 mL, 9 mmol) was added, followed by HATU (1.43 g, 3.8 mmol), and after stirring at 0° C. for 10 min, the mixture was allowed to warm up to ambient temperature and stirred at ambient temperature for 1.75 hr. The reaction mixture was diluted with dichloromethane (200 mL) and washed with 1M HCl (200 mL), water (2×150 mL), and brine (150 mL). The organic layer was separated, dried over Na$_2$SO$_4$, filtered and concentrated to oil. The reaction product was isolated by flash Compound M17 (above; 1.25 g, 1.25 mmol) was dissolved in 25 ml of chloroform, and acetic acid (1.5 mL), 4-methylmorpholine (0.75 mL), and Pd(PPh$_3$)$_4$ (145 mg, 0.13 mmol), were added under argon. The reaction mixture was stirred at ambient temperature for 5 hrs. The reaction mixture was diluted with dichloromethane (150 mL) and was washed with 1M NaHSO$_4$ and brine. The organic layer was separated, dried over Na$_2$SO$_4$, filtered and concentrated to oil. The reaction product was isolated by flash chromatography on silica gel column (3×15 cm) eluting with a step gradient 2-10% methanol in dichloromethane to yield 0.788 g (65%). $^1$H NMR (DMSO-d$_6$): δ 1.39 (s, 18H), 1.72 (s, 3H), 1.77 (s, 3H), 2.52 (m, 2H), 3.18-3.49 (m, 4H), 4.09-4.42 (m, 4H), 4.59-4.97 (m, 4H), 5.19-5.33 (m, 2H), 5.8-6.1 (m, 1H), 7.12-7.20 (m. 2H), 7.31-7.43 (m, 7H), 7.64-7.74 (m, 3H), 7.88-7.90 (m, 2H).

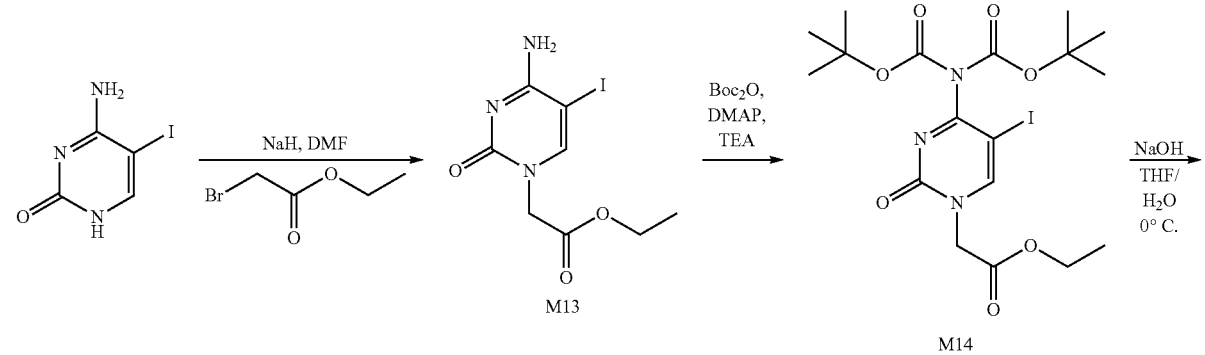

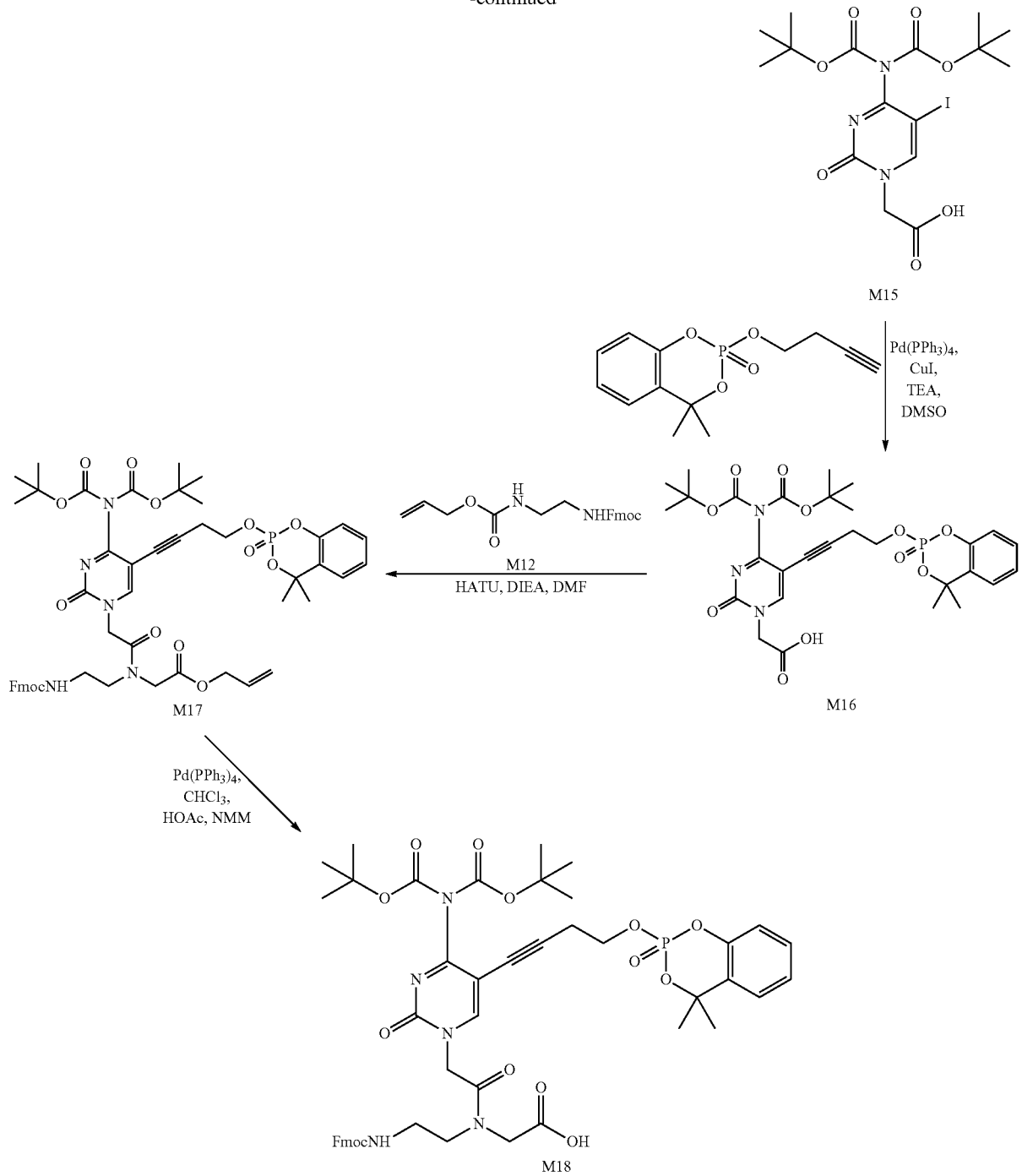

Example 4

Synthesis of DMT-$C^{PP}$-1 Phosphoramidite (M24)

Example 4 describes a synthetic procedure for preparing a protected form of a modified cytosine 3'-phosphoramidite monomer M24, which comprises a protected phosphonate (i.e., Z is $CH_2$) whose phosphorus atom is linked to the pyrimidine 5-carbon by a 1-pentynyl linker (this modified base is sometimes designated herein as $C^{PP}$). This example illustrates a method of making a protected nucleoside phosphoramidite comprising a phosphonate moiety.

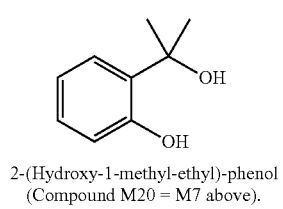

2-(Hydroxy-1-methyl-ethyl)-phenol
(Compound M20 = M7 above).

This compound was synthesized following the protocol described in: Johnsson, R., Mani, K., Cheng, F., Ellervik, U. (2006) *J. Org. Chem.*, v.71, pp. 3444-3451.

Compound M21

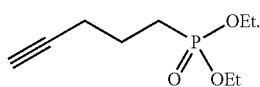

A 100-mL round-bottomed flask fitted with an air condenser was charged with 5-chloro-1-pentyne (15.0 mL, 0.14 mol) and triethyl phosphite (25.7 mL, 0.15 mol). The content of the flask was heated up to reflux (120° C. mineral oil bath). Refluxing was continued intermittently for 2 weeks, during which time the boiling temperature rose gradually to 180° C. At that time only traces of triethyl phosphite were detectable in the reaction mixture by $^{31}$P NMR. The heating was discontinued, and the mixture was cooled down to an ambient temperature and vacuum distilled at ~1 mm, Hg. The fraction boiling at 91-92° C./~1 mm was collected affording 14.0 g (48%) of colorless liquid. $^1$H NMR (DMSO-$d_6$): δ 4.04-3.93 (m, 4H), 2.82 (t, 1H), 2.26 (dt, 2H), 1.85-1.74 (m, 2H), 1.69-1.58 (m, 2H), 1.23 (t, 6H). $^{31}$P NMR (DMSO-d6): δ 31.20).

Compound M22

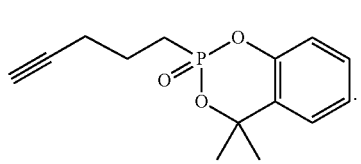

Compound M20 (above; 2.04 g, 10.0 mmol) was dissolved in bromotrimethylsilane (3.96 mL, 30.0 mmol) at room temperature under Ar atmosphere, and was kept sealed overnight in a 50-mL, round-bottomed flask. The volatiles were removed under reduced pressure, and the residue was desiccated in a high vacuum for half an hour. The content of the flask was dissolved in anhydrous dichloromethane (10 mL) containing N,N-dimethylformamide (0.1 mL), and chilled to −20° C. under argon. The solution was treated with oxalyl chloride (3.43 mL, 40.0 mmol) dropwise with stirring. The reaction mixture was allowed to warm up to room temperature, and was stirred for 2 hours. It was then evaporated under reduced pressure, and the residue was desiccated for 1 h in a high vacuum. The remaining yellowish solid was dissolved in anhydrous dichloromethane (5.0 mL), and the resulting solution was chilled to −20° C. A solution of compound M6 (above; 1.52 g, 10.0 mmol) in dichloromethane (5 mL) containing N,N-diisopropylethylamine (6.96 mL, 40.0 mmol) was added drop wise with stirring. The reaction mixture was allowed to warm up to ambient temperature, stirred overnight, and was then diluted with ethyl acetate (150 mL). The resulting solution was washed with 5% NaHCO$_3$ (3×50 mL) and brine (50 mL). The organic layer was separated, dried over Na$_2$SO$_4$, filtered and concentrated. The product (TLC: R$_f$~0.2 in ethyl acetate/hexanes (1:1) or R$_f$~0.6 in ethyl acetate) was isolated by flash chromatography on silica gel using a step gradient 20-80% ethyl acetate in hexanes. Yield: 2.05 g (78%; slightly colored oil). $^1$H NMR (DMSO-$d_6$): δ 7.43-7.35 (m, 2H), 7.23-7.13 (m, 2H), 2.79 (t, 1H), 2.24 (bt, 2H), 1.99-1.89 (m, 2H), 1.73 (ds, 6H), 1.68-1.57 (m, 2H). $^{31}$P NMR (DMSO-d6): δ 22.34.

Compound M23

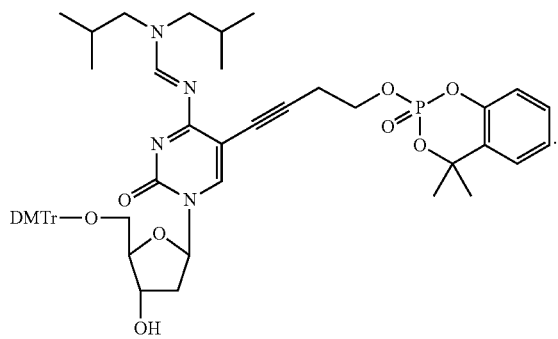

Compound M4 (above) is combined with Pd(PPh$_3$)$_4$, copper(I) iodide in a round-bottomed flask equipped with a magnetic stirring bar. The flask is evacuated and filled with argon gas, sealed with a septum and an argon balloon. A solution of compound M22 (above) and triethylamine is added using a syringe through the septum, and the mixture is stirred at ambient temperature under Ar atmosphere. After 15 hours the reaction mixture is diluted with ethyl acetate and washed with 0.1 M Na$_2$EDTA, saturated aqueous NaHCO$_3$ (3×50 mL), and brine (50 mL). The organic layer is separated, dried over Na$_2$SO$_4$, and concentrated to oil. The reaction product is isolated by flash chromatography on silica gel.

Compound M24

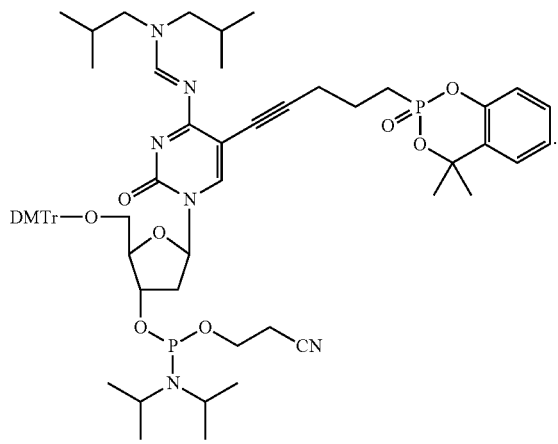

To a stirred solution of Compound M23 (above) in anhydrous CH$_2$Cl$_2$ containing N,N-diisopropylethylamine kept at 0° C., 2-cyanoethyl N,N— is added drop wise under argon. The reaction mixture is allowed to warm up to room temperature, and methanol is added after 30 min. The reaction mixture is diluted with ethyl acetate and washed with 5% aqueous NaHCO$_3$ and brine. The organic layer is separated, dried over Na$_2$SO$_4$, and concentrated to oil. The product M24 is purified using flash chromatography on silica gel column.

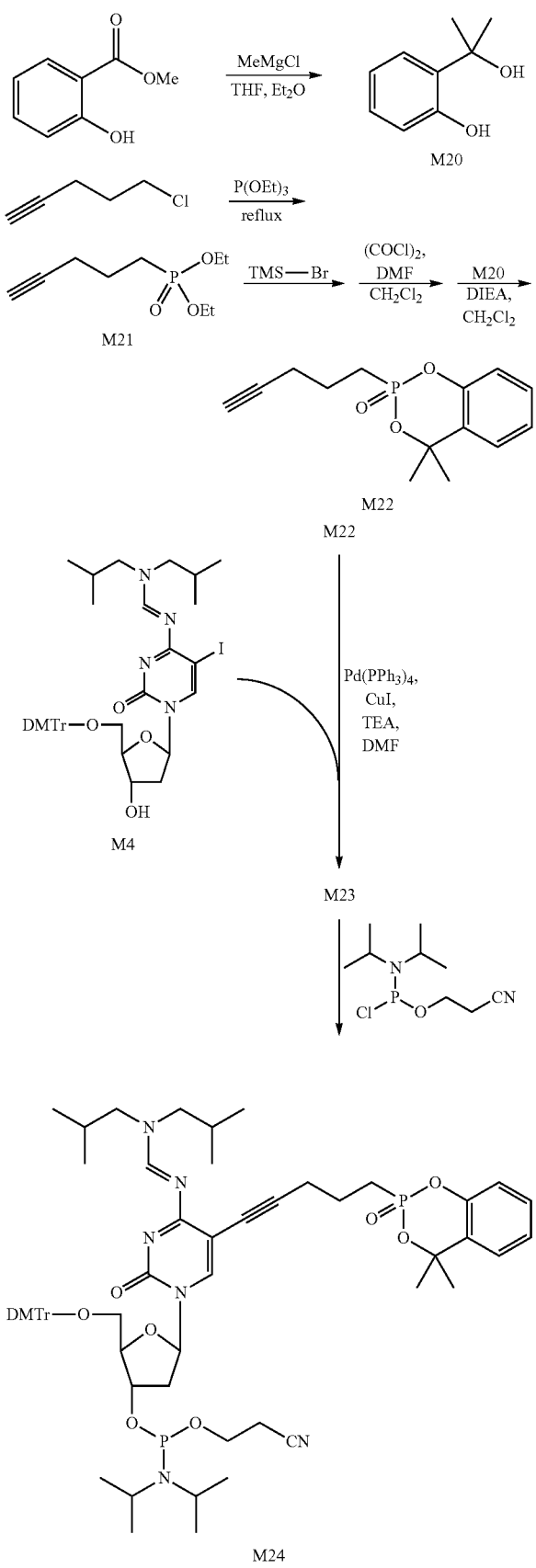

Example 5

Hybridization of $C^{BP}$ Substituted Oligomers

Example 5 describes an experiment in which the affinity of an 18-mer DNA oligomer comprising one or two $C^{BP}$ moieties (with deprotected phosphate groups) was compared with the hybridization affinity of a corresponding 18-mer DNA oligomer comprising only conventional A, C, G and T nucleotides, when each was hybridized to a complementary 12-mer DNA oligomer ("Short Complement") or complementary 18-mer DNA oligomer ("Long Complement"). As shown by the melting curve data in FIG. 1 (hybridization of the modified and unmodified oligomers to the Short Complement), and as summarized in Tables 1 and 2, the modified oligomer that comprised two $C^{BP}$ moieties was observed to have a $T_m$ that was substantially greater than the $T_m$ values observed for hybridization of the unmodified 18-mer and the 18-mers comprising a single $C^{BP}$ moiety. The $T_m$ values of the oligomers comprising a single $C^{BP}$ moiety were substantially higher than the $T_m$ values observed with the unsubstituted oligomer, conveying a stabilization of 2.2° C. and 2.8° C. when hybridized to the complementary 12-mer, and a stabilization of 1.9° C. and 2.0° C. when hybridized to the complementary 18-mer (see Tables 1 and 2). The $T_m$ values observed for the doubly modified C3 oligomer were 4.6° C. and 3.6° C. for hybridization to the complementary 12-mer and 18-mer, respectively, indicating that the individual stabilizing effects of each modified base substitution are almost additive in this example.

The hybridization of oligomers comprising $C^{BP}$ substitutions were characterized and compared with the hybridization properties of unmodified oligomers comprising only conventional cytosine bases. Oligomers C1 and C2 comprised one $C^{BP}$ moiety, and oligomer C3 comprised two $C^{BP}$ moieties. The oligomer sequences are set forth below:

```
C1
                                         (SEQ ID NO: 1)
5'-TTT AGA (C^BP)TT CTT GGA TTT-3'

C2
                                         (SEQ ID NO: 2)
5'-TTT AGA CTT (C^BP)TT GGA TTT-3'

C3
                                         (SEQ ID NO: 3)
5'-TTT AGA (C^BP)TT (C^BP)TT GGA TTT-3'
```

The sequences of the short and long complements are set forth below:

```
Short Complement
                                         (SEQ ID NO: 4)
5'-TCC AAG AAG TCT-3'

Long Complement
                                         (SEQ ID NO: 5)
5'-AAA TCC AAG AAG TCT AAA-3''
```

In their 3'→5' directions, Short Complement and Long Complement sequences read 3'-TCTGAAGAACCT-5' and 3'-AAATCTGAAGAACCTAAA-5', respectively (showing better the complementary regions to C1, C2, and C3).

$T_m$ data were obtained using standard melting conditions (1 uM for each oligo, 3 mM $MgCl_2$, 15 mM KCl, 25 mM HEPES, pH 8), and absorbance at 270 nm vs. temperature (° C.) was recorded.

FIG. 1 shows melting curves (plotted as the first derivative of absorbance at 270 nm versus temperature in ° C.) observed for oligomers C1, C2, and C3 hybridized to the short complement sequence described above. $T_m$ values that were calculated from the data in FIG. 1 are tabulated below in Table 1:

TABLE 1

Hybridization to Short Complement Sequence

| Oligomer | $T_m$ (° C.) | $\Delta T_m$ (° C.) |
|---|---|---|
| Unsubstituted | 45.0 | NA |
| C1 | 47.8 | 2.8 |
| C2 | 47.2 | 2.2 |
| C3 | 49.6 | 4.6 |

$\Delta T_m$ is the $T_m$ (modified oligomer) minus $T_m$ (unsubstituted oligomer)
NA = not applicable.

In the same way explained above, melting curves were also recorded for hybridization of the oligomers to the long complement, and the resulting $T_m$ values are tabulated below in Table 2:

TABLE 2

Hybridization to Long Complement Sequence

| Oligomer | $T_m$ (° C.) | $\Delta T_m$ (° C.) |
|---|---|---|
| Unsubstituted | 54.2 | NA |
| C1 | 56.1 | 1.9 |
| C2 | 56.2 | 2.0 |
| C3 | 57.8 | 3.6 |

$\Delta T_m$ is the $T_m$ (modified oligomer) minus $T_m$ (unsubstituted oligomer)
NA = not applicable.

Example 6

Performance of Modified Probes in 5'-Nuclease PCR

In Example 6, 5'-nuclease PCR reactions were performed using cleavable quenched fluorescent probes comprising 0, 1, 2, 3 or 5 modified ($C^{BP}$) bases of the invention. The PCR profiles shown in FIGS. 2A and 2B demonstrate that all of the oligomers comprising $C^{BP}$ moieties performed efficiently as detection probes. Furthermore, oligomers comprising $C^{BP}$ moieties have a greater affinity for complementary oligomer sequences than do unmodified oligomers, allowing higher PCR extension temperatures and shorter PCR cycle times.

5'-Nuclease PCR probes comprising one to five $C^{BP}$ substitutions were evaluated. Human genome DNA beta-globulin housekeeping gene was used as the target. PCR was performed on a Stratagene Mx3005P instrument, with each reaction tested in triplicate. The following PCR protocol was used:

Amplicon length—96 bp, 10,000 copies/reaction;
Primer concentrations—200 nM;
Probe concentration—200 nM;
First denaturation for 60 sec at 95° C.
Cycle: annealing—extension for 30 sec at 68° C.; denature for 8 sec at 95° C.

The forward and reverse primers had the following sequences:

F1
(SEQ ID NO: 6)
5'-AATTCCTGAAGCTGACAG($C^{BP}$)A-3'

R1
(SEQ ID NO: 7)
5'-AAATAGCCTCCAGGC($C^{BP}$)A-3'

The oligomer probes had the following sequences: Table 3

TABLE 3

| Name | 5' | Sequence | 3' | SEQ ID |
|---|---|---|---|---|
| Pf1-C-1 | FAM | 5'-($C^{BP}$)TC CGT GGC CTT AGC TGT GCT C-3' | BHQ1 | 8 |
| Pf1-C-2 | FAM | 5'-CT($C^{BP}$) CGT GGC CTT AGC TGT GCT C-3' | BHQ1 | 9 |
| Pf1-C-3 | FAM | 5'-CTC ($C^{BP}$)GT GGC CTT AGC TGT GCT C-3' | BHQ1 | 10 |
| Pf1-C-4 | FAM | 5'-($C^{BP}$)TC ($C^{BP}$)GT GGC CTT AGC TGT GCT C-3' | BHQ1 | 11 |
| Pf1-C-5 | FAM | 5'-CTC ($C^{BP}$)GT GG($C^{BP}$) CTT AGC TGT GCT C-3' | BHQ1 | 12 |
| Pf1-C-6 | FAM | 5'-($C^{BP}$)TC ($C^{BP}$)GT GG($C^{BP}$) CTT AGC TGT GCT C-3' | BHQ1 | 13 |
| Pf1-C-7 | FAM | 5'-CTC CGT GGC ($C^{BP}$)TT AG($C^{BP}$) TGT G($C^{BP}$)T C-3' | BHQ1 | 14 |
| Pf1-C-8 | FAM | 5'-($C^{BP}$)TC ($C^{BP}$)GT GGC ($C^{BP}$)TT AG($C^{BP}$) TGT G($C^{BP}$)T C-3' | BHQ1 | 15 |

Figure 2A:
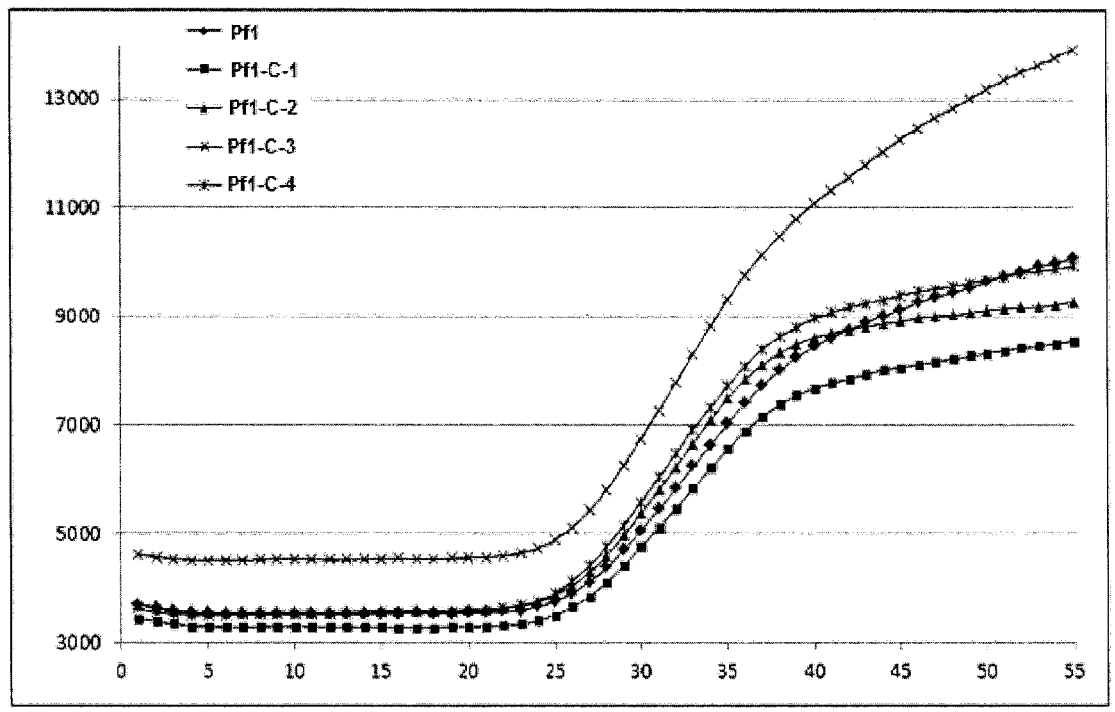
FIGS. 2A and 2B schematically depicts plots of fluorescence (516 nm, FAM (Em)) as a function of cycle number ($C_n$) obtained from 5' nuclease PCR reactions using fluorescent probes comprising one to five $C^{BP}$ moieties, and forward and reverse primers that comprised only conventional cytosine bases. The following probes were used: Pf1-C-1 (one modified cytosine base), Pf1-C-2 (one modified cytosine base), Pf1-C-3 (one modified cytosine base), Pf1-C-4 (two modified cytosine bases), Pf1-C-5 (two modified cytosine bases; "Pf1-5"), Pf1-C-6 (three modified cytosine bases; "Pf1-6"), Pf1-C-7 (three modified cytosine bases; "Pf1-7"), and Pf1-C-8 (five modified cytosine bases; "Pf1-8"). Primer Pf1 has the same nucleotide sequence as the modified cytosine probes, however, only natural bases, i.e., no modified cytosine base. Additional details are provided in Example 6 and Table 4.
Figure 2B:
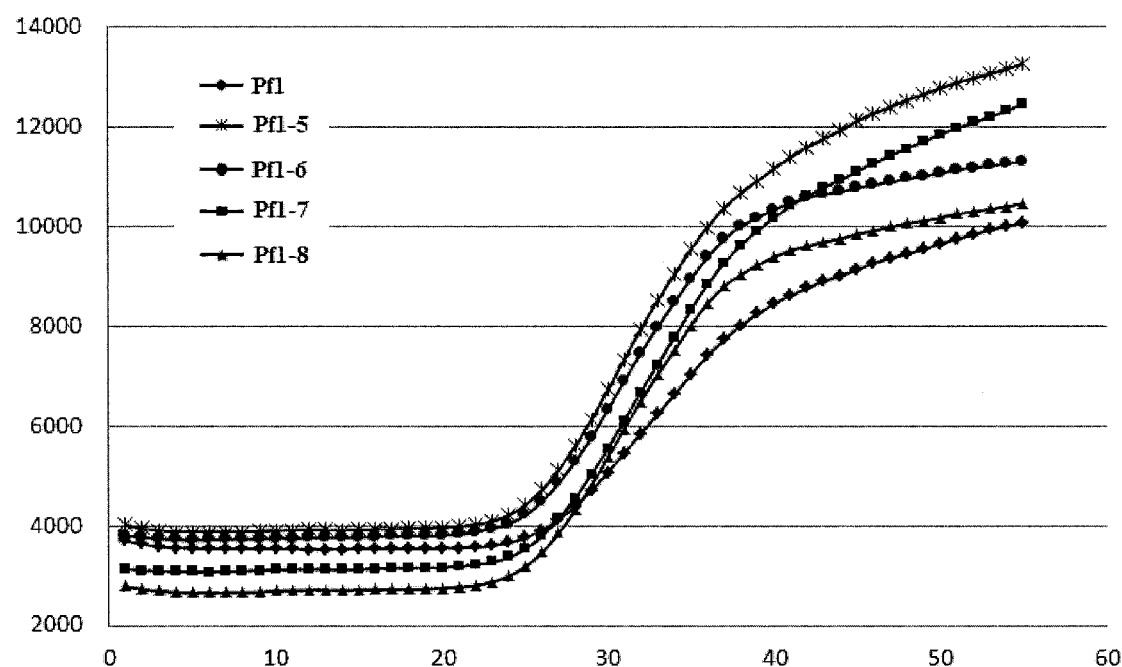

PCR fluorescence profiles as a function of cycle number are shown in FIGS. 2A and 2B. As can be seen, $C^{BP}$ substitutions at one or multiple locations across the oligomer, even close to the 5' end, do not affect the efficiency of 5' cleavage of the probe by the 5'-nuclease activity of the polymerase (modification at the 3' end is not shown since it has no effect on 5'-nuclease cleavage). In addition, probes comprising modified bases of the invention instead of conventional cytosine bases generally have a higher binding affinity for the complementary target sequence than do probes comprising.

Example 7

Performance of 5' Nuclease PCR Probes

Figure 3:
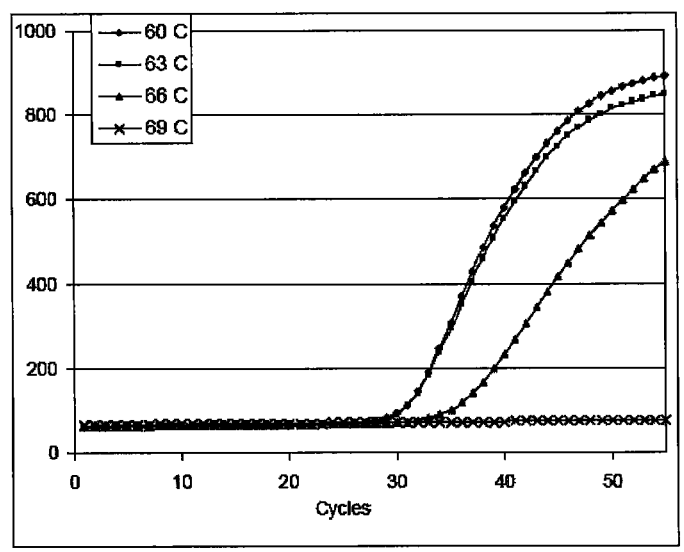
FIG. 3 schematically depicts plots of fluorescence (516 nm, FAM (Em)) as a function of cycle number ($C_n$) from 5' nuclease PCR reactions that were performed using various primer extension temperatures (60° C., "60 C"; 63° C., "63 C"; 66° C., "66 C"; and 69° C., "69 C") with forward and reverse primers each comprising one $C^{BP}$ moiety. Additional details are provided in Example 7 and in Table 4.

Example 7 describes studies in which 5'-nuclease PCR reactions were performed using a pair of forward and reverse primers containing either no $C^{BP}$ moiety (primers P2F and P2R) or one $C^{BP}$ moiety (P1F and P1R). FIG. 3 shows PCR profiles obtained using the modified primers P1F and P1R with a series of different extension temperatures. As can be seen, the primers performed well with extension temperatures of 60° C. and 63° C., but PCR efficiency was reduced at 66° C. and undetectable at 69° C. These results demonstrate how modified oligomers of the invention can be characterized to determine optimal PCR conditions and whether further modifications should be made to the primers, probes, or reaction conditions if desired.

Figure 4A:
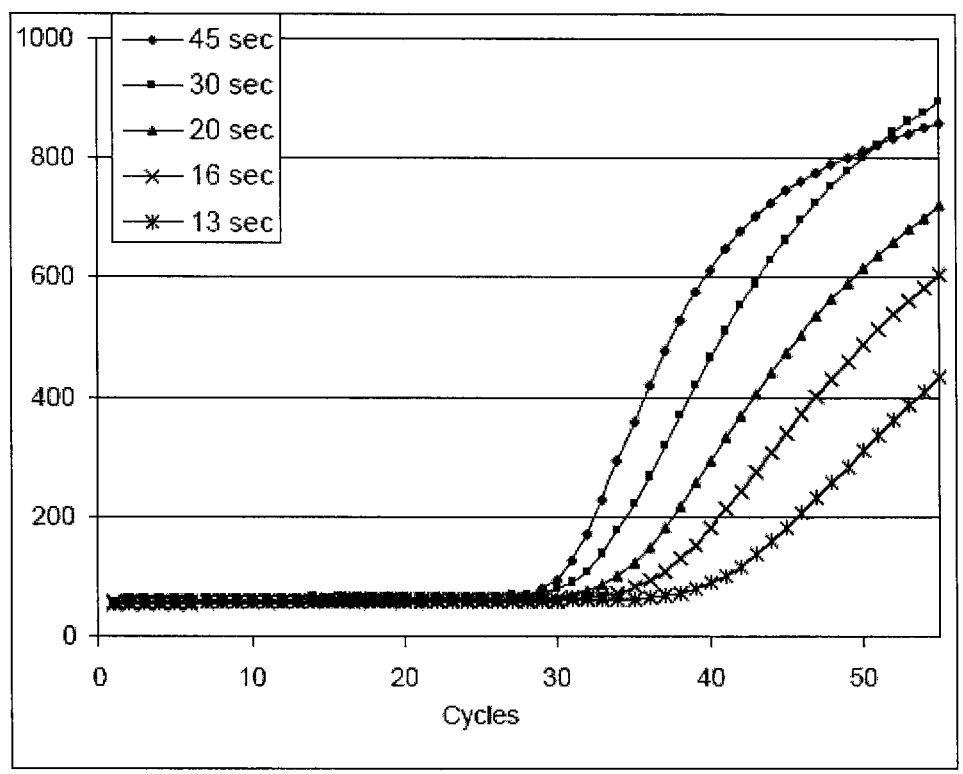
FIGS. 4A and 4B schematically depict plots of fluorescence as a function of cycle number from 5' nuclease PCR reactions using unmodified primers (FIG. 4A) or modified cytosine primers each comprising one $C^{BP}$ moiety (FIG. 4B) and various annealing times (FIG. 4A: 13, 16, 20, 30 and 45 seconds.
Figure 4B:
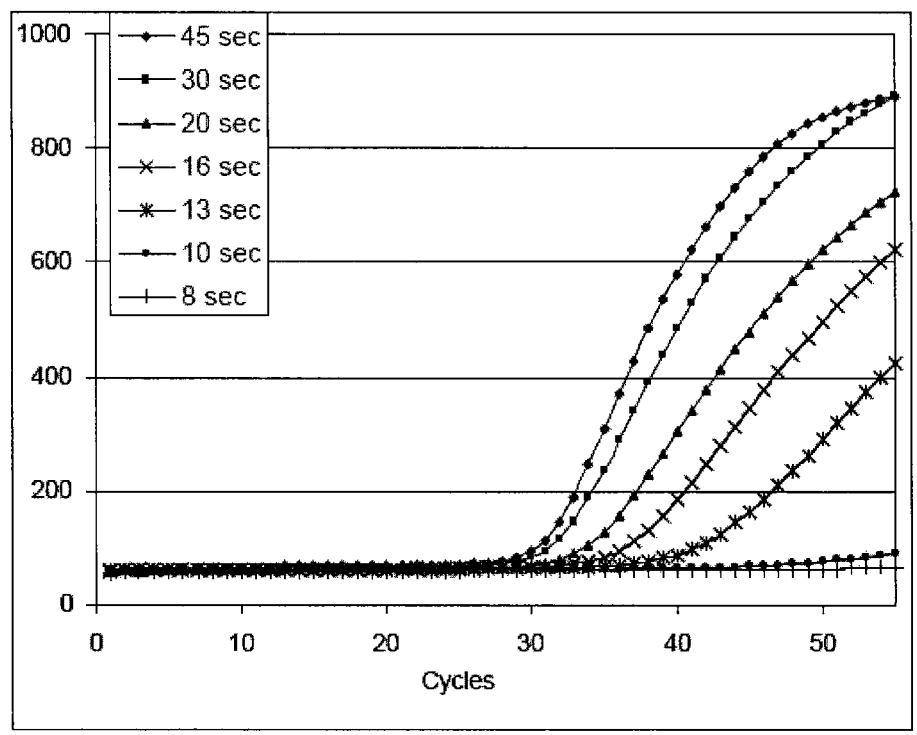

The modified oligomer primers in Example 7 were also evaluated at different annealing times, relative to the performance of the unmodified primers. The resulting PCR profiles are shown in FIGS. 4A and 4B. As can be seen, the modified primers performed efficiently as polymerase substrates in PCR.

Oligomers comprising $C^{BP}$ moieties were also evaluated as 5'-nuclease PCR primers. In this study, both forward and reverse primers comprised a single $C^{BP}$ substitution near the 3' end with the following sequences:

```
P1F
                                        (SEQ ID NO: 16)
5'-AATTCCTGAAGCTGACAG(C^BP)A-3'

P1R
                                        (SEQ ID NO: 17)
5'-AAATAGCCTCCAGGC(C^BP)A-3'
```

In one study, 5'-nuclease PCR reactions were performed using four different extension temperatures under the following conditions:

Target: 10,000 copies/reaction;
Primer concentration—200 nM;
Probe concentration—200 nM;
First denaturation for 60 sec at 95° C.;
Cycle: annealing—extension for 30 sec at 60, 63, 66, or 69° C.; denature for 8 sec at 95° C.

PCR fluorescence profiles as a function of cycle number are shown in FIG. 3. As can be seen, the primers performed well with extension temperatures of 60° C. and 63° C., but PCR efficiency was reduced at 66° C. and non-existent at 69° C. These results demonstrate how modified oligomers of the invention can be characterized to determine optimal PCR conditions and whether further modifications should be made if desired.

In a second study, the modified primers above were subjected to 5'-nuclease PCR with a range of different annealing times, and the results were compared with results obtained using corresponding unmodified primers whose sequences are shown below:

```
P2F
                                        (SEQ ID NO: 18)
5'-AATTCCTGAAGCTGACAGCA-3'

P2R
                                        (SEQ ID NO: 19)
5'-AAATAGCCTCCAGGCCA-3'
```

In particular, the unmodified forward and reverse primers were evaluated at five different annealing times (13, 16, 20, 30 and 45 seconds—see FIG. 4A), and the $C^{BP}$ modified primers P1F and P1R set forth above were evaluated at seven different annealing times (8, 10, 13, 16, 20, 30 and 45 seconds—see FIG. 4B). The results demonstrate that in addition to increasing hybridization affinity, the primers were good substrates for the primer extension activity of the DNA polymerase enzyme. These results demonstrate that there is no "slow-down" effect detected at shorter annealing times for the modified primers. The amplification curve threshold cycle (Ct) and EPR are identical to natural primers at appropriately low annealing temperatures for both modified and unmodified primers.

Example 8

Synthesis of PNA Oligomers Comprising CBP Moieties

Example 8 provides a synthetic protocol by which PNA oligomers comprising modified and/or unmodified bases were prepared using Fmoc-PAL-PEG-PS resin.

PNA synthesis was performed manually using Fmoc-PAL-PEG-PS resin (0.16 mmol/g) from Applied Biosystems. Fmoc-protected monomers and HATU were obtained from PolyOrg, Inc. Solvents were from EMD. Piperidine, TFA, DIEA, and m-cresol were from Aldrich. Resin was swelled in DCM for at least 2 hours before use, and then washed with DCM (5×) and DMF (5×).

Synthetic Protocol:
Deprotection: 20% piperidine in DMF, 2×5 min
Washing: DMF (5×), DMF/DCM (1:1) (5×)
Preactivation: HATU (4 eq), DIEA (4.5 eq), PNA-monomer (1 eq), DMF, 3 min
Coupling: 30 min
Washing: DMF/DCM (1:1) (5×)
Capping: 5% Ac2O/5% DIEA, 10 min
Washing: DMF (5×)

Cleavage from the solid support was performed with TFA/m-cresol (9:1) for 90 minutes at room temperature followed by precipitation in Et$_2$O. The solid was collected by centrifugation, and the Et$_2$O wash/centrifugation was repeated two times. After purification by reversed phase HPLC, the PNAs were characterized by ESI(+) mass spectrometry.

Example 9

Synthesis of PNA-DNA Chimerae

Example 9 provides a general method by which PNA-DNA chimeric oligomers can be made, wherein a PNA monomer comprising a modified base of the invention is incorporated either by means of a nucleoside phosphoramidite or a modified PNA monomer.

The PNA oligomers and DNA-PNA chimerae are synthesized via solid phase strategy using Fmoc protected PNA monomers and nucleoside phosphoramidites as previously reported (Petraccone et al., J. Am. Chem. Soc., 2005, 16125-16223). Tentagel-OH resin functionalized with N-Fmoc glycine is reacted with the first PNA unit followed by reacting with 5'-O-DMT-3'-O-(2-cyanoethyl)phosphoramidite guanosine, thymidine, adenosine, and cytidine units to obtain the chimerae. The chimerae are detached from the solid support and deprotected with concentrated aqueous ammonia at 55° C. for 12-16 hr. The solutions are evaporated to remove ammonia, and the products are isolated via preparative reversed-phase HPLC.

Example 10

Hybridization of $C^{BP}$-Modified PNA to DNA

Example 10 describes an experiment in which melting temperatures were determined for PNA oligomers which had been made by the protocol of Example 8 and which comprised a $C^{BP}$ moiety. The duplex of C-PNA with the target DNA had a $T_m$ of 47° C. versus a $T_n$ of 38.4° C. for the control duplex. These results show that the $C^{BP}$-containing PNA oligomer had a higher $T_m$ value, and thus, higher binding affinity, than the $T_m$ value observed for the control DNA oligomer.

A PNA oligomer having a $C^{BP}$ substitution was prepared, and its hybridization affinity ($T_m$) for a complementary target DNA sequence was compared to that of a corresponding unmodified control DNA oligomer. $T_m$ data were obtained using standard melting conditions (1 uM for each oligo, 3 mM MgCl$_2$, 15 mM KCl, 25 mM HEPES, pH 8). The following sequences were used:

```
C-PNA
                                (SEQ ID NO: 20)
5'-CGATAC^BP TGC-3'

Control DNA
                                (SEQ ID NO: 21)
5'-CGATACTGC-3'

Target DNA
                                (SEQ ID NO: 22)
5'-TTTGCAGTATCGTTT-3'
```

The duplex of C-PNA with the target DNA had $T_m$ of 47° C. versus the control duplex $T_m$ of 38.4° C. Accordingly, the modified PNA showed a $T_m$ enhancement of about 8.6° C. for hybridization to a complementary DNA strand, relative to the $T_m$ observed for hybridization of a corresponding DNA oligomer (lacking any base modification) to the same complementary DNA strand.

Example 11

General Method for Synthesis of Nucleosides

Compound NS1 illustrates a modified nucleoside comprising a modified base comprising a phosphonate moiety. Compound NS1 is prepared analogously to Compound M23 via Pd(PPh$_3$)$_4$ and copper(I) iodide-catalyzed coupling followed by the removal of the protecting groups with 25% aqueous ammonia.

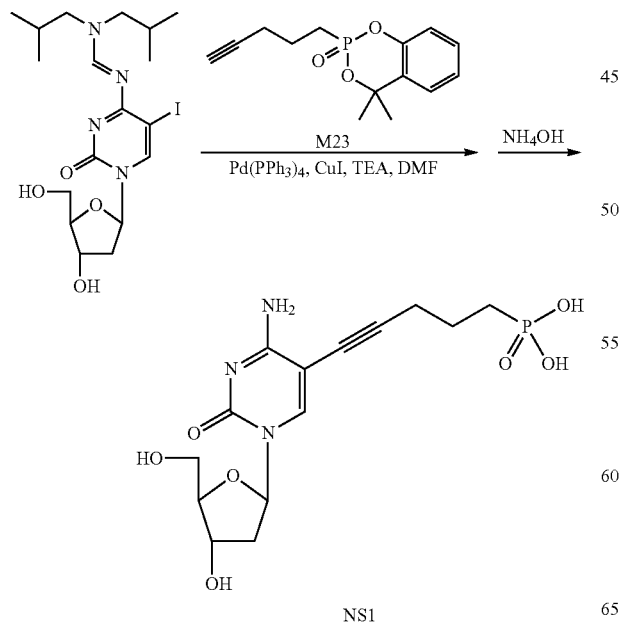

NS1

Compound NS2 illustrates a modified nucleoside comprising a modified base comprising a phosphate moiety. Compound NS2 is prepared analogously to Compound M23 via Pd(PPh$_3$)$_4$ and copper(I) iodide-catalyzed coupling followed by the removal of the protecting groups with 25% aqueous ammonia.

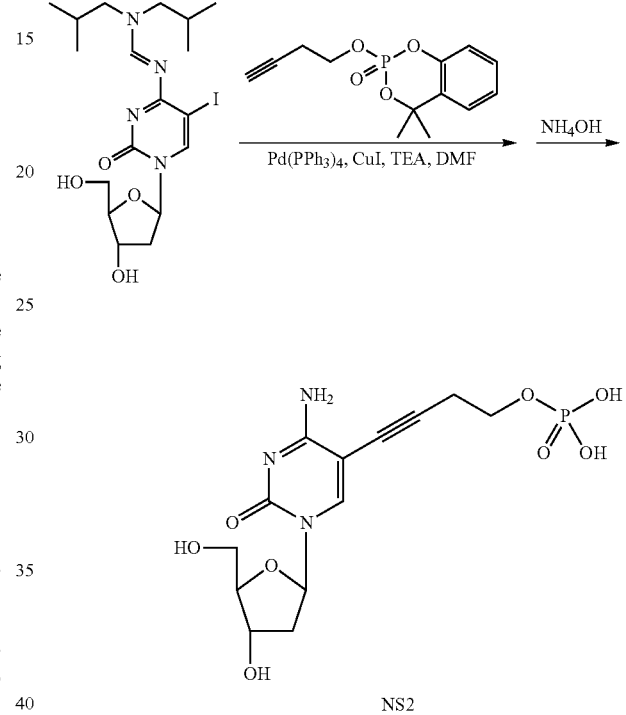

NS2

Example 12

General Method for Synthesis of Nucleotide 5'-Triphosphates

Triphosphates NT1 and NT2 are synthesized from the corresponding 5'-DMTr derivatives M23 and M5 by acetylation of the 3'-hydroxy group, followed by the removal of the 5'-DMTr group and conversion to the corresponding triphosphates using the protocol described by Hollenstein (Hollenstein M., *Synthesis of Deoxynucleoside Triphosphates that Include Proline, Urea, or Sulfonamide Groups and Their Polymerase Incorporation into DNA, Chem. Eur. J.* 2012, 18, 13320-13330). Compound NT1 illustrates a modified nucleotide 5'-triphosphate comprising modified base comprising a phosphate moiety. Compound NT2 illustrates a modified nucleotide 5'-triphosphate comprising modified base comprising a phosphonate moiety).

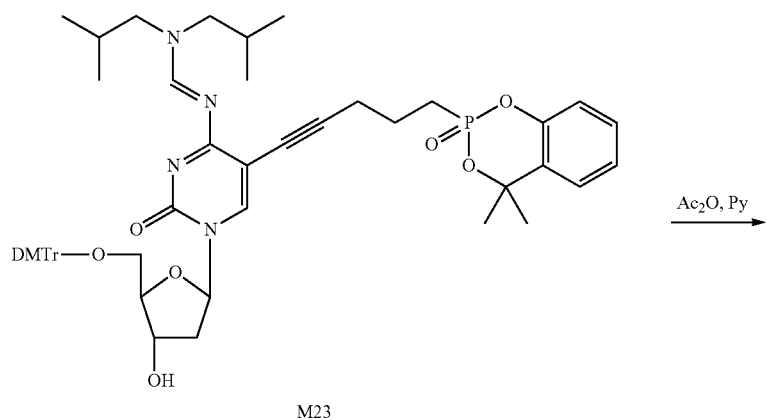
M23
Ac₂O, Py →
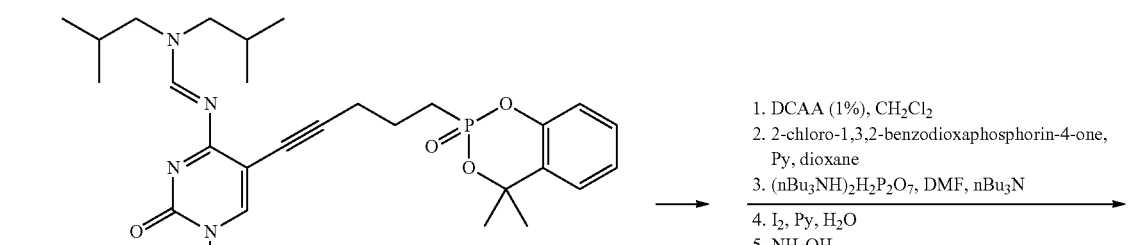
NT1-1
1. DCAA (1%), CH₂Cl₂
2. 2-chloro-1,3,2-benzodioxaphosphorin-4-one, Py, dioxane
3. (nBu₃NH)₂H₂P₂O₇, DMF, nBu₃N
4. I₂, Py, H₂O
5. NH₄OH
→
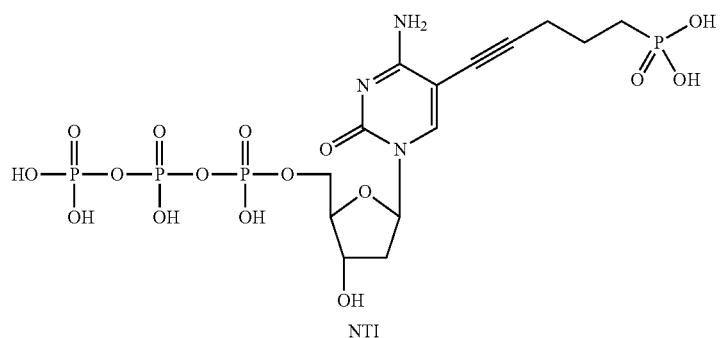
NTI
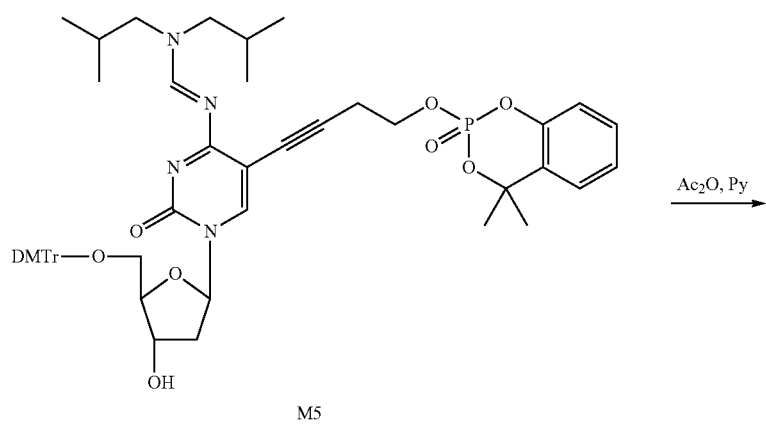
M5
Ac₂O, Py →

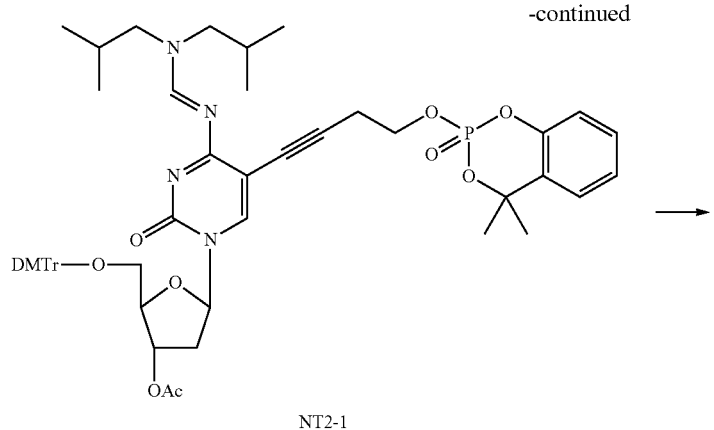

NT2-1

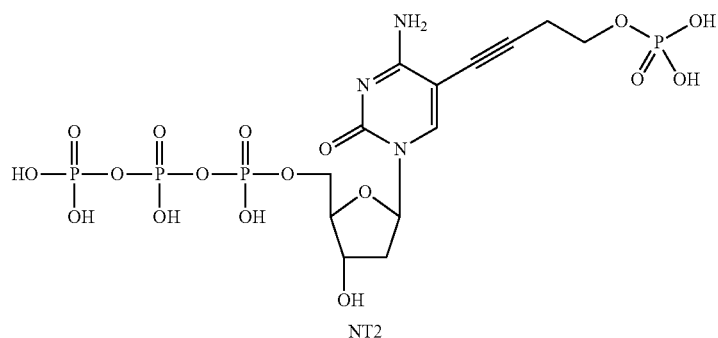

NT2

Example 13

Consolidated List of Sequences

Table 4 below provides a consolidated list of sequences prepared and used herein as described. Table 4

TABLE 4

Consolidated List of Sequences.

| SEQ ID NO | Name | Sequence |
|---|---|---|
| 1 | C1 | 5'-TTT AGA ($C^{BP}$)TT CTT GGA TTT-3' |
| 2 | C2 | 5'-TTT AGA CTT ($C^{BP}$)TT GGA TTT-3' |
| 3 | C3 | 5'-TTT AGA (CBP)TT ($C^{BP}$)TT GGA TTT-3' |
| 4 | Short complement | 5'-TCC AAG AAG TCT-3' |
| 5 | Long complement | 5'-AAA TCC AAG AAG TCT AAA-3' |
| 6 | F1 | 5'-AATTCCTGAAGCTGACAG($C^{BP}$)A-3' |
| 7 | R1 | 5'-AAATAGCCTCCAGGC($C^{BP}$)A-3' |
| 8 | Pfl-C-1 | 5'-FAM-($C^{BP}$)TC CGT GGC CTT AGC TGT GCT C-BHQ1-3' |
| 9 | Pfl-C-2 | 5'-FAM-CT($C^{BP}$) CGT GGC CTT AGC TGT GCT C-BHQ1-3' |
| 10 | Pfl-C-3 | 5'-FAM-CTC ($C^{BP}$)GT GGC CTT AGC TGT GCT C-BHQ1-3' |
| 11 | Pfl-C-4 | 5'-FAM-($C^{BP}$)TC ($C^{BP}$)GT GGC CTT AGC TGT GCT C-BHQ1-3' |
| 12 | Pfl-C-5 | 5'-FAM-CTC ($C^{BP}$)GT GG($C^{BP}$) CTT AGC TGT GCT C-BHQ1-3' |
| 13 | Pfl-C-6 | 5'-FAM-($C^{BP}$)TC ($C^{BP}$)GT GG($C^{BP}$) CTT AGC TGT GCT C-BHQ1-3' |
| 14 | Pfl-C-7 | 5'-FAM-CTC CGT GGC ($C^{BP}$)TT AG($C^{BP}$) TGT G($C^{BP}$)T C-BHQ1-3' |
| 15 | Pfl-C-8 | 5'-FAM-($C^{BP}$)TC ($C^{BP}$)GT GGC ($C^{BP}$)TT AG($C^{BP}$) TGT G($C^{BP}$)T C-BHQ1-3' |
| 16 | P1F | 5'-AATTCCTGAAGCTGACAG($C^{BP}$)A-3' |
| 17 | P1R | 5'-AAATAGCCTCCAGGC($C^{BP}$)A-3' |
| 18 | P2F | 5'-AATTCCTGAAGCTGACAGCA-3' |
| 19 | P2R | 5'-AAATAGCCTCCAGGCCA-3' |
| 20 | C-PNA | 5'-CGATAC$^{BP}$TGC-3' |
| 21 | Control DNA | 5'-CGATACTGC-3' |
| 22 | Target DNA | 5'-TTTGCAGTATCGTTT-3' |

Although a variety of examples and other information are provided above to explain aspects within the scope of the claims, no limitation of the claims should be implied based on particular features or arrangements in such examples, as one of ordinary skill would be able to use these examples to derive a wide variety of implementations. Furthermore, although some subject matter may have been described in language specific to examples of structural features, conditions or uses, it is to be understood that the subject matter defined in the claims is not necessarily so limited.

What is claimed is:

1. A polynucleotide oligomer comprising at least one modified base, wherein the at least one modified base is represented by the formula:

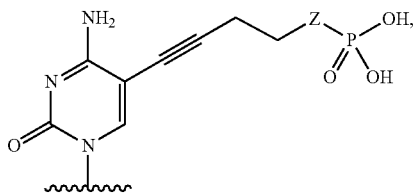

and wherein Z is $CH_2$ or O.

2. The polynucleotide oligomer of claim 1, wherein the polynucleotide oligomer further comprises at least one deoxyribonucleotide moiety.

3. The polynucleotide oligomer of claim 2, wherein the modified base is covalently linked to the deoxyribonucleotide moiety.

4. The polynucleotide oligomer of claim 1, wherein the polynucleotide oligomer further comprises at least one peptide nucleic acid moiety.

5. The polynucleotide oligomer of claim 4, wherein the modified base is covalently linked to the at least one peptide nucleic acid moiety in the polynucleotide oligomer.

6. The polynucleotide oligomer of claim 1, wherein the polynucleotide oligomer is a PNA/DNA chimera.

7. The polynucleotide oligomer of claim 1, wherein the polynucleotide oligomer further comprises at least two modified bases and wherein Z in the at least two modified bases is the same or different.

8. The polynucleotide oligomer of claim 1, wherein the polynucleotide oligomer further comprises the modified base at its 3' end or at one base from its 3' end.

9. The polynucleotide oligomer of claim 1, wherein the polynucleotide oligomer further comprises a minor groove binder or an intercalator.

10. The polynucleotide oligomer of claim 1, wherein the polynucleotide oligomer further comprises a sugar modification.

11. The polynucleotide oligomer of claim 10, wherein the sugar modification is selected from the group consisting of arabinose, d-arabino-hexitol, 2-fluoroarabinose, xylulose, hexose, and a bicyclic sugar.

12. The polynucleotide oligomer of claim 1, wherein the polynucleotide oligomer further comprises a backbone modification.

13. The polynucleotide oligomer of claim 12, wherein the backbone modification is selected from the group consisting of a modified sugar phosphate backbone, a locked nucleic acid backbone, a peptidic backbone, a phosphotriester backbone, a phosphoramidate backbone, a siloxane backbone, a carboxymethylester backbone, an acetamidate backbone, a carbamate backbone, a thioether backbone, a bridged methylene phosphonate backbone, a phosphorothioate backbone, a methylphosphonate backbone, an alkylphosphonate backbone, a phosphate ester backbone, an alkylphosphonothioate backbone, a phosphorodithioate backbone, a carbonate backbone, a phosphate triester backbone, a carboxymethyl ester backbone, a methylphosphorothioate backbone, a phosphorodithioate backbone, a backbone having p-ethoxy linkages, and a combinations of two or more of any of the foregoing.

14. The polynucleotide oligomer of claim 1, wherein the polynucleotide oligomer further comprises a 3'-terminal nucleotide that is extendable by a DNA or RNA dependent polymerase enzyme.

15. The polynucleotide oligomer of claim 14, wherein the polynucleotide oligomer further comprises fewer than 30 nucleotides.

16. The polynucleotide oligomer of claim 15, wherein the oligonucleotide oligomer further comprises from about 9 to about 25 nucleotides.

17. The polynucleotide oligomer of claim 1, wherein the polynucleotide oligomer further comprises at least one detectable label.

18. The polynucleotide oligomer of claim 17, wherein the detectable label is a fluorophore.

19. The polynucleotide oligomer claim 1, wherein the polynucleotide oligomer further comprises a fluorescence quencher.

20. A method for hybridization of a polynucleotide oligomer comprising a modified base with a nucleic acid target sequence suspected of being present in a reaction mixture, the method comprising the steps of:

(a) incubating a reaction mixture comprising a polynucleotide oligomer and suspected of comprising a target nucleic acid sequence under conditions favorable for hybridization of the polynucleotide oligomer to the target nucleic acid sequence if present in the reaction mixture; and (b) detecting the presence or confirming the absence of the target nucleic acid sequence in the reaction mixture;

wherein the polynucleotide oligomer is complementary to a sequence within the nucleic acid target sequence, wherein the polynucleotide oligomer comprises at least one modified base, wherein the at least one modified base is represented by the formula:

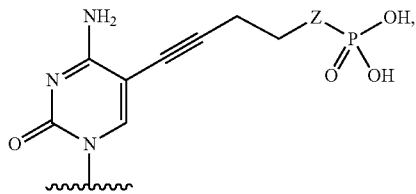

and wherein Z is $CH_2$ or O.

21. The method of claim 20, wherein the polynucleotide oligomer further comprises a moiety selected from the group consisting of a detectable label, a fluorophore and a fluorescence quencher.

22. A duplex comprising:

(i) at least one polynucleotide oligomer; and (ii) a polynucleotide sequence wherein the at least one polynucleotide oligomer comprises four or more contiguous bases that are complementary with and hybridized to at least four contiguous bases of the polynucleotide sequence, wherein the at least one polynucleotide oligomer further comprises at least one modified base, wherein the at least one modified base is represented by the formula

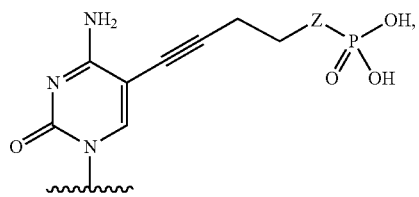

and
wherein Z is CH$_2$ or O.

23. The duplex of claim 22, wherein the polynucleotide oligomer further comprises a moiety selected from the group consisting of a detectable label, a fluorophore and a fluorescence quencher.

24. A modified nucleoside phosphoramidite represented by the formula:

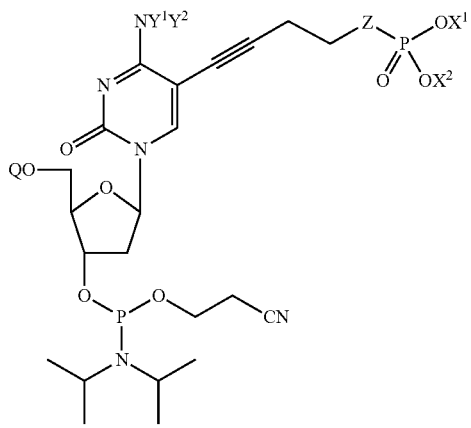

wherein Z is CH$_2$ or 0;
wherein X$^1$ and X$^2$ taken separately are protecting groups that are the same or different, or X$^1$ and X$^2$ taken together are a bidentate protecting group;
wherein Y$^1$ and Y$^2$ are independently H or nitrogen protecting group, or Y$^1$ and Y$^2$ together are nitrogen protecting group; and
wherein Q is a hydroxyl protecting group.

25. A modified peptide nucleic acid monomer represented by the formula:

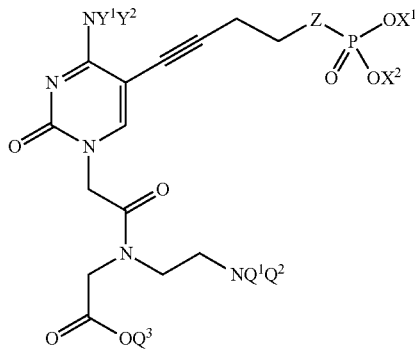

wherein Z is CH$_2$ or O;
wherein X$^1$ and X$^2$ taken separately are protecting groups that are the same or different, or X$^1$ and X$^2$ taken together are a bidentate protecting group;
wherein Y$^1$ and Y$^2$ are independently H or nitrogen protecting group, or Y$^1$ and Y$^2$ together are nitrogen protecting group;
wherein Q$^1$ and Q$^2$ are independently H or nitrogen protecting group, or Q$^1$ and Q$^2$ together are nitrogen protecting group; and
wherein Q$^3$ is H or a carboxyl protecting group.

26. A modified cytosine nucleoside represented by the formula:

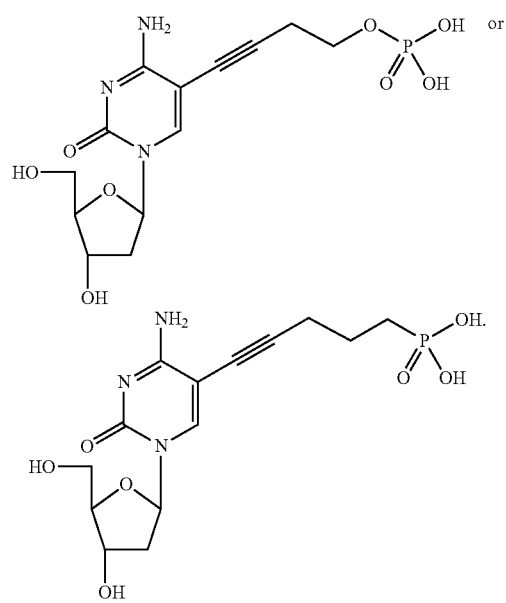

27. A modified cytosine nucleotide 5'-triphosphate represented by the formula:

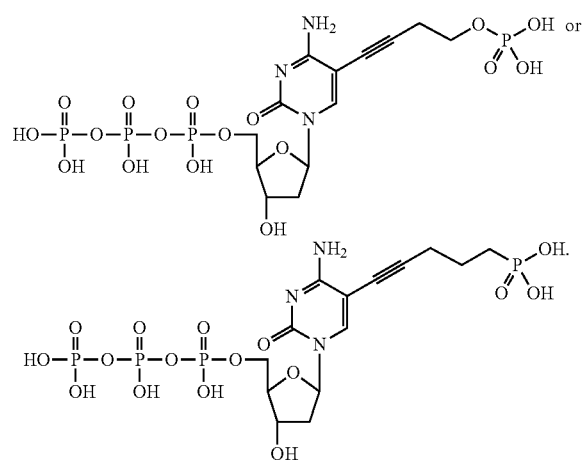

28. The polynucleotide oligomer of claim 1, wherein the polynucleotide oligomer further comprises a label selected from the group consisting of a chromophore, a radioisotope, a spin-label, an enzyme label, a chemiluminescent label, an electrochemiluminescent compound, a magnetic label, a microsphere, a colloidal metal, an immunological label, a ligand, a fluorescent dye, horseradish peroxidase, alkaline phosphatase, streptavidin, biotin, an epitope recognized by an antibody, coumarin, a coumarin derivative, a cyanine dye, an eosin, an erythrosin, a macrocyclic chelate of an lanthanide ion, a rhodamine dye, a fluorescent energy transfer dye.

29. The polynucleotide oligomer of claim 1, wherein, when written in its 5' to 3' direction, the at least one modified base is in a position selected from the group consisting of position 1 of the polynucleotide oligomer, position 2 of the polynucleotide oligomer, position 3 of the polynucleotide oligomer, position 4 of the polynucleotide oligomer, position 5 of the polynucleotide oligomer, position 6 of the polynucleotide oligomer, position 7 of the polynucleotide oligomer, position 8 of the polynucleotide oligomer, position 9 of the polynucleotide oligomer, position 10 of the polynucleotide oligomer, position 11 of the polynucleotide oligomer, position 12 of the polynucleotide oligomer, position 13 of the polynucleotide oligomer, position 14 of the polynucleotide oligomer, position 15 of the polynucleotide oligomer, position 16 of the polynucleotide oligomer, position 17 of the polynucleotide oligomer; position 18 of the polynucleotide oligomer; position 19 of the polynucleotide oligomer, and position 20 of the polynucleotide oligomer.

30. The polynucleotide oligomer of claim 1, wherein the polynucleotide oligomer is attached to a solid support.

31. The polynucleotide oligomer of claim 30, wherein the solid support is selected from the group consisting of a bead, an array, and a microarray.

32. The polynucleotide oligomer of claim 1, wherein the polynucleotide oligomer further comprises one or more nucleotides having attached a modified sugar moiety.

33. The polynucleotide oligomer of claim 32, wherein the modified sugar moiety is selected from the group consisting of a 2'-substituted sugar, a 2'-O-alkyl-ribose sugar, a 2'-amino-deoxyribose sugar, a 2'-fluoro-deoxyribose sugar, a 2'-fluoro-arabinose sugar, a 2'-O-methoxyethyl-ribose sugar, and a locked nucleic acid sugar.

34. The polynucleotide oligomer of claim 1, wherein the polynucleotide oligomer further comprises one or more non-standard bases.

35. The polynucleotide oligomer of claim 34, wherein the one or more non-standard base is selected from the group consisting of an unsubstituted pyrazolo[3,4-d]pyrimidine base, a 3-substituted pyrazolo[3,4-d]pyrimidine, a modified purine, a modified pyrimidine, and a 5-substituted pyrimidine.

36. The polynucleotide oligomer of claim 1, wherein the polynucleotide oligomer further comprises one or more pendant groups.

37. The polynucleotide oligomer of claim 36, wherein the one or more pendant group is selected from the group consisting of a lipophilic group, a minor groove binder, an intercalator, a chelating agent, and a cross-linking agent.

38. The polynucleotide oligomer of claim 1, wherein the polynucleotide oligomer further comprises a tail moiety attached either at the 3'-end, 5-end or at both ends of the polynucleotide oligomer.

39. The polynucleotide oligomer of claim 38, wherein the tail moiety is selected from the group consisting of a phosphate, a phosphate ester, an alkyl group, an aminoalkyl group, and a lipophilic group.

40. The method of claim 20, wherein the polynucleotide oligomer further comprises at least one deoxyribonucleotide moiety.

41. The method of claim 40, wherein the modified base is covalently linked to the deoxyribonucleotide moiety.

42. The method of claim 20, wherein the polynucleotide oligomer further comprises at least one peptide nucleic acid moiety.

43. The method of claim 42, wherein the modified base is covalently linked to the at least one peptide nucleic acid moiety in the polynucleotide oligomer.

44. The method of claim 20, wherein the polynucleotide oligomer is a PNA/DNA chimera.

45. The method of claim 20, wherein the polynucleotide oligomer further comprises at least two modified bases and wherein Z in the at least two modified bases is the same or different.

46. The method of claim 20, wherein the polynucleotide oligomer further comprises the modified base at its 3' end or at one base from its 3' end.

47. The method of claim 20, wherein the polynucleotide oligomer further comprises a minor groove binder or an intercalator.

48. The method of claim 20, wherein the polynucleotide oligomer further comprises a sugar modification.

49. The method of claim 48, wherein the sugar modification is selected from the group consisting of arabinose, d-arabino-hexitol, 2-fluoroarabinose, xylulose, hexose, and a bicyclic sugar.

50. The method of claim 20, wherein the polynucleotide oligomer further comprises a backbone modification.

51. The method of claim 50, wherein the backbone modification is selected from the group consisting of a modified sugar phosphate backbone, a locked nucleic acid backbone, a peptidic backbone, a phosphotriester backbone, a phosphoramidate backbone, a siloxane backbone, a carboxymethylester backbone, an acetamidate backbone, a carbamate backbone, a thioether backbone, a bridged methylene phosphonate backbone, a phosphorothioate backbone, a methylphosphonate backbone, an alkylphosphonate backbone, a phosphate ester backbone, an alkylphosphonothioate backbone, a phosphorodithioate backbone, a carbonate backbone, a phosphate triester backbone, a carboxymethyl ester backbone, a methylphosphorothioate backbone, a phosphorodithioate backbone, a backbone having p-ethoxy linkages, and a combinations of two or more of any of the foregoing.

52. The method of claim 20, wherein the polynucleotide oligomer further comprises a 3'-terminal nucleotide that is extendable by a DNA or RNA dependent polymerase enzyme.

53. The method of claim 52, wherein the polynucleotide oligomer further comprises fewer than 30 nucleotides.

54. The method of claim 53, wherein the oligonucleotide oligomer further comprises from about 9 to about 25 nucleotides.

55. The method of claim 20, wherein the step of detecting comprises detecting a detectable label attached to the polynucleotide oligomer.

56. The method of claim 55, wherein the detectable label is a fluorophore.

57. The method of claim 20, wherein the polynucleotide oligomer further comprises a fluorescence quencher.

58. The method of claim 20, wherein the polynucleotide oligomer further comprises a label selected from the group consisting of a chromophore, a radioisotope, a spin-label, an enzyme label, a chemiluminescent label, an electrochemiluminescent compound, a magnetic label, a microsphere, a colloidal metal, an immunological label, a ligand, a fluorescent dye, horseradish peroxidase, alkaline phosphatase, streptavidin, biotin, an epitope recognized by an antibody, coumarin, a coumarin derivative, a cyanine dye, an eosin, an erythrosin, a macrocyclic chelate of an lanthanide ion, a rhodamine dye, and a fluorescent energy transfer dye.

59. The method of claim 20, wherein, when written in its 5' to 3' direction, the at least one modified base is in a position selected from the group consisting of position 1 of the polynucleotide oligomer, position 2 of the polynucleotide oligomer, position 3 of the polynucleotide oligomer, position 4 of the polynucleotide oligomer, position 5 of the polynucleotide oligomer, position 6 of the polynucleotide oligomer, position 7 of the polynucleotide oligomer, position 8 of the polynucleotide oligomer, position 9 of the polynucleotide oligomer, position 10 of the polynucleotide oligomer, position 11 of the polynucleotide oligomer, position 12 of the polynucleotide oligomer, position 13 of the polynucleotide oligomer, position 14 of the polynucleotide oligomer, position 15 of the polynucleotide oligomer, position 16 of the polynucleotide oligomer, position 17 of the polynucleotide oligomer; position 18 of the polynucleotide oligomer; position 19 of the polynucleotide oligomer, and position 20 of the polynucleotide oligomer.

60. The method of claim 20, wherein the polynucleotide oligomer is attached to a solid support.

61. The method of claim 60, wherein the solid support is selected from the group consisting of a bead, an array, and a microarray.

62. The method of claim 20, wherein the polynucleotide oligomer further comprises one or more nucleotides having attached a modified sugar moiety.

63. The method of claim 62, wherein the modified sugar moiety is selected from the group consisting of a 2'-substituted sugar, a 2'-O-alkyl-ribose sugar, a 2'-amino-deoxyribose sugar, a 2'-fluoro-deoxyribose sugar, a 2'-fluoro-arabinose sugar, a 2'-O-methoxyethyl-ribose sugar, and a locked nucleic acid sugar.

64. The method of claim 20, wherein the polynucleotide oligomer further comprises one or more non-standard bases.

65. The method of claim 64, wherein the one or more non-standard base is selected from the group consisting of an unsubstituted pyrazolo[3,4-d]pyrimidine base, a 3-substituted pyrazolo[3,4-d]pyrimidine, a modified purine, a modified pyrimidine, and a 5-substituted pyrimidine.

66. The method of claim 20, wherein the polynucleotide oligomer further comprises one or more pendant groups.

67. The method of claim 66, wherein the one or more pendant group is selected from the group consisting of a lipophilic group, a minor groove binder, an intercalator, a chelating agent, and a cross-linking agent.

68. The method of claim 20, wherein the polynucleotide oligomer further comprises a tail moiety attached either at the 3'-end, 5-end or at both ends of the polynucleotide oligomer.

69. The method of claim 68, wherein the tail moiety is selected from the group consisting of a phosphate, a phosphate ester, an alkyl group, an aminoalkyl group, and a lipophilic group.

70. The method of claim 20, further comprising the step of:
(c) performing an amplification reaction.

71. The method of claim 70, wherein the amplification reaction is selected from the group consisting of polymerase chain reaction (PCR), reverse-transcriptase PCR, real-time PCR, nested PCR, multiplex PCR, quantitative PCR, nucleic acid sequence based amplification, transcription mediated amplification, ligase chain reaction, rolling circle amplification, and strand displacement amplification.

72. The method of claim 70, wherein the amplification reaction is carried out in an automated thermal cycler.

73. The method of claim 20, further comprising the step of:
(c) performing a DNA sequencing reaction.

74. The method of claim 20, further comprising the step of:
(c) performing a primer extension reaction.

75. The method of claim 20, further comprising the step of:
(c) attaching the polynucleotide oligomer to an array.

76. The method of claim 75, wherein the array is selected from the group consisting of a chip array, a platform array, a bead array, a liquid phase array, and a zip-code array.

77. The method of claim 75, wherein the array comprises nitrocellulose, glass, a silicon wafer, or an optical fiber.

78. The method of claim 20, further comprising the step of:
(c) performing a 5'-nuclease reaction.

79. The method of claim 20, wherein the step of detecting comprises detecting a detectable label, a fluorophore or a fluorescence quencher attached to the polynucleotide oligomer.

80. The duplex of claim 22, wherein the polynucleotide oligomer further comprises at least one deoxyribonucleotide moiety.

81. The duplex of claim 80, wherein the modified base is covalently linked to the deoxyribonucleotide moiety.

82. The duplex of claim 22, wherein the polynucleotide oligomer further comprises at least one peptide nucleic acid moiety.

83. The duplex of claim 82, wherein the modified base is covalently linked to the at least one peptide nucleic acid moiety in the polynucleotide oligomer.

84. The duplex of claim 22, wherein the polynucleotide oligomer is a PNA/DNA chimera.

85. The duplex of claim 22, wherein the polynucleotide oligomer comprises at least two modified bases and wherein Z in the at least two modified bases is the same or different.

86. The duplex of claim 22, wherein the polynucleotide oligomer comprises the modified base at its 3' end or at one base from its 3' end.

87. The duplex of claim 22, wherein the polynucleotide oligomer further comprises a minor groove binder or an intercalator.

88. The duplex of claim 22, wherein the polynucleotide oligomer further comprises a sugar modification.

89. The duplex of claim 88, wherein the sugar modification is selected from the group consisting of arabinose, d-arabino-hexitol, 2-fluoroarabinose, xylulose, hexose, and a bicyclic sugar.

90. The duplex of claim 22, wherein the polynucleotide oligomer further comprises a backbone modification.

91. The duplex of claim 90, wherein the backbone modification is selected from the group consisting of a modified sugar phosphate backbone, a locked nucleic acid backbone, a peptidic backbone, a phosphotriester backbone, a phosphoramidate backbone, a siloxane backbone, a carboxymethylester backbone, an acetamidate backbone, a carbamate backbone, a thioether backbone, a bridged methylene phosphonate backbone, a phosphorothioate backbone, a methylphosphonate backbone, an alkylphosphonate backbone, a phosphate ester backbone, an alkylphosphonothioate backbone, a phosphorodithioate backbone, a carbonate backbone, a phosphate triester backbone, a carboxymethyl ester backbone, a methylphosphorothioate backbone, a phosphorodithioate backbone, a backbone having p-ethoxy linkages, and a combinations of two or more of any of the foregoing.

92. The duplex of claim 22, wherein the polynucleotide oligomer further comprises a 3'-terminal nucleotide that is extendable by a DNA or RNA dependent polymerase enzyme.

93. The duplex of claim 92, wherein the polynucleotide oligomer comprises fewer than 30 nucleotides.

94. The duplex of claim 93, wherein the oligonucleotide oligomer comprises from about 9 to about 25 nucleotides.

95. The duplex of claim 22, wherein the polynucleotide oligomer further comprises at least one detectable label.

96. The duplex of claim 95, wherein the detectable label is a fluorophore.

97. The duplex of claim 20, wherein the polynucleotide oligomer further comprises a fluorescence quencher.

98. The duplex of claim 22, wherein the polynucleotide oligomer further comprises a label selected from the group consisting of a chromophore, a radioisotope, a spin-label, an enzyme label, a chemiluminescent label, an electrochemiluminescent compound, a magnetic label, a microsphere, a colloidal metal, an immunological label, a ligand, a fluorescent dye, horseradish peroxidase, alkaline phosphatase, streptavidin, biotin, an epitope recognized by an antibody, coumarin, a coumarin derivative, a cyanine dye, an eosin, an erythrosin, a macrocyclic chelate of an lanthanide ion, a rhodamine dye, and a fluorescent energy transfer dye.

99. The duplex of claim 22, wherein, when written in its 5' to 3' direction, the at least one modified base is in a position selected from the group consisting of position 1 of the polynucleotide oligomer, position 2 of the polynucleotide oligomer, position 3 of the polynucleotide oligomer, position 4 of the polynucleotide oligomer, position 5 of the polynucleotide oligomer, position 6 of the polynucleotide oligomer position 7 of the polynucleotide oligomer, position 8 of the polynucleotide oligomer, position 9 of the polynucleotide oligomer, position 10 of the polynucleotide oligomer, position 11 of the polynucleotide oligomer, position 12 of the polynucleotide oligomer, position 13 of the polynucleotide oligomer, position 14 of the polynucleotide oligomer, position 15 of the polynucleotide oligomer, position 16 of the polynucleotide oligomer, position 17 of the polynucleotide oligomer; position 18 of the polynucleotide oligomer; position 19 of the polynucleotide oligomer, and position 20 of the polynucleotide oligomer.

100. The duplex of claim 22, wherein the polynucleotide oligomer is attached to a solid support.

101. The duplex of claim 100, wherein the solid support is selected from the group consisting of a bead, an array, and a microarray.

102. The duplex of claim 22, wherein the polynucleotide oligomer further comprises one or more nucleotides having attached a modified sugar moiety.

103. The duplex of claim 102, wherein the modified sugar moiety is selected from the group consisting of a 2'-substituted sugar, a 2'-O-alkyl-ribose sugar, a 2'-amino-deoxyribose sugar, a 2'-fluoro-deoxyribose sugar, a 2'-fluoro-arabinose sugar, a 2'-O-methoxyethyl-ribose sugar, and a locked nucleic acid sugar.

104. The duplex of claim 22, wherein the polynucleotide oligomer further comprises one or more non-standard bases.

105. The duplex of claim 104, wherein the one or more non-standard base is selected from the group consisting of an unsubstituted pyrazolo[3,4-d]pyrimidine base, a 3-substituted pyrazolo[3,4-d]pyrimidine, a modified purine, a modified pyrimidine, and a 5-substituted pyrimidine.

106. The duplex of claim 22, wherein the polynucleotide oligomer further comprises one or more pendant groups.

107. The duplex of claim 106, wherein the one or more pendant group is selected from the group consisting of a lipophilic group, a minor groove binder, an intercalator, a chelating agent, and a cross-linking agent.

108. The duplex of claim 22, wherein the polynucleotide oligomer further comprises a tail moiety attached either at the 3'-end, 5-end or at both ends of the polynucleotide oligomer.

109. The duplex of claim 108, wherein the tail moiety is selected from the group consisting of a phosphate, a phosphate ester, an alkyl group, an aminoalkyl group, and a lipophilic group.

110. The duplex of claim 22, wherein the duplex is attached to a solid support.

111. The duplex of claim 110, wherein the solid support is selected from the group consisting of a bead, an array, and a microarray.

112. The modified nucleoside phosphoramidite of claim 24, wherein Z is O.

113. The modified nucleoside phosphoramidite of claim 24, wherein Q is trityl, methoxytrityl, or dimethoxytrityl.

114. The modified nucleoside phosphoramidite of claim 24, wherein the bidentate protecting group is o-benzylene, α-methyl-o-benzylene, or α,α-dimethyl-o-benzylene.

115. The modified nucleoside phosphoramidite of claim 24, wherein $X^1$ and $X^2$ independently have a structure represented by the formula:

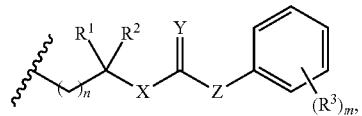

wherein $R^1$ and $R^2$ are independently hydrogen, $C_1$-$C_6$ alkyl, $C_2$-$C_6$ alkenyl, $C_2$-$C_6$ alkynyl, $C_3$-$C_6$ cycloalkyl, or phenyl;

n and m are independently 0, 1, 2, 3 or 4; X is O or $NR^4$;

Y is O or S;

Z is a bond, O or $NR^4$; and each $R^3$ is same or different and is, independently, $C_1$-$C_6$ alkyl, $C_2$-$C_6$ alkenyl, $C_2$-$C_6$ alkynyl, $C_3$-$C_6$ cycloalkyl, cyano, nitro, halogen, $C_1$-$C_6$ alkyloxy, $C_3$-$C_6$ cycloalkyloxy, $NR^{5a}R^{5b}$, or phenyl; wherein $R^4$, $R^{5a}$ and $R^{5b}$ are each independently $C_3$-$C_6$ cycloalkyl, or phenyl.

116. The modified nucleoside phosphoramidite of claim 24, wherein $X^1$ and $X^2$ independently have the structure

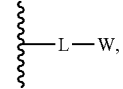

wherein L is a bond, $C_1$-$C_8$ alkylene or $C_2$-$C_8$ heteroalkylene, $C_2$-$C_8$ alkenylene; and W is H, cyano, $C(O)NR^aR^b$, $NO_2$, $N^+R^aR^c$, $C_6H_4NO_2$, $C_6H_4Cl$, $C_6H_3(NO_2)_2$, $C_6H_2(NO_2)_3$, $SO_2R^c$, or $S(O)_2OR^c$; $R^a$ and $R^b$ are independently H, $CF_3$, $C_1$-$C_8$ alkyl or $C_6$-$C_{10}$ aryl; and $R^c$ is $C_1$-$C_8$ alkyl or $C_6$-$C_{10}$ aryl.

117. The modified nucleoside phosphoramidite of claim 116, wherein L is a bond and W is H.

118. The modified nucleoside phosphoramidite of claim 24, wherein $X^1$ and $X^2$ each separately are pivaloyloxybenzyl groups.

119. The modified peptide nucleic acid monomer of claim 25, wherein $Q^1$ is H, $Q^2$ is Fmoc, and $Q^3$ is H.

* * * * *

```
                          SEQUENCE LISTING

<160> NUMBER OF SEQ ID NOS: 22

<210> SEQ ID NO 1
<211> LENGTH: 18
<212> TYPE: DNA
<213> ORGANISM: Artificial
<220> FEATURE:
<223> OTHER INFORMATION: Description of artificial sequence: C1 Sequence
<220> FEATURE:
<221> NAME/KEY: modified_base
<222> LOCATION: (7)..(7)
<223> OTHER INFORMATION: CBP moiety

<400> SEQUENCE: 1
tttagacttc ttggattt                                                 18

<210> SEQ ID NO 2
<211> LENGTH: 18
<212> TYPE: DNA
<213> ORGANISM: Artificial
<220> FEATURE:
<223> OTHER INFORMATION: Description of artificial sequence: C2 Sequence
<220> FEATURE:
<221> NAME/KEY: modified_base
<222> LOCATION: (10)..(10)
<223> OTHER INFORMATION: CBP moiety

<400> SEQUENCE: 2
tttagacttc ttggattt                                                 18

<210> SEQ ID NO 3
<211> LENGTH: 18
<212> TYPE: DNA
<213> ORGANISM: Artificial
<220> FEATURE:
<223> OTHER INFORMATION: Description of artificial sequence: C3 Sequence
<220> FEATURE:
<221> NAME/KEY: modified_base
<222> LOCATION: (7)..(7)
<223> OTHER INFORMATION: CBP moiety
<220> FEATURE:
<221> NAME/KEY: modified_base
<222> LOCATION: (10)..(10)
<223> OTHER INFORMATION: CBP moiety

<400> SEQUENCE: 3
tttagacttc ttggattt                                                 18

<210> SEQ ID NO 4
<211> LENGTH: 12
<212> TYPE: DNA
<213> ORGANISM: Artificial
<220> FEATURE:
<223> OTHER INFORMATION: Description of artificial sequence: Short
      complement Sequence

<400> SEQUENCE: 4
tccaagaagt ct                                                       12

<210> SEQ ID NO 5
<211> LENGTH: 18
<212> TYPE: DNA
<213> ORGANISM: Artificial
```

```
<220> FEATURE:
<223> OTHER INFORMATION: Description of artificial sequence: Long
      complement Sequence

<400> SEQUENCE: 5
aaatccaaga agtctaaa                                                  18

<210> SEQ ID NO 6
<211> LENGTH: 20
<212> TYPE: DNA
<213> ORGANISM: Artificial
<220> FEATURE:
<223> OTHER INFORMATION: Description of artificial sequence: F1 Sequence
<220> FEATURE:
<221> NAME/KEY: modified_base
<222> LOCATION: (19)..(19)
<223> OTHER INFORMATION: CBP moiety

<400> SEQUENCE: 6
aattcctgaa gctgacagca                                                20

<210> SEQ ID NO 7
<211> LENGTH: 17
<212> TYPE: DNA
<213> ORGANISM: Artificial
<220> FEATURE:
<223> OTHER INFORMATION: Description of artificial sequence: R1 Sequence
<220> FEATURE:
<221> NAME/KEY: modified_base
<222> LOCATION: (16)..(16)
<223> OTHER INFORMATION: CBP moiety

<400> SEQUENCE: 7
aaatagcctc caggcca                                                   17

<210> SEQ ID NO 8
<211> LENGTH: 22
<212> TYPE: DNA
<213> ORGANISM: Artificial
<220> FEATURE:
<223> OTHER INFORMATION: Description of artificial sequence: Pf1-C-1
      Sequence
<220> FEATURE:
<221> NAME/KEY: modified_base
<222> LOCATION: (1)..(1)
<223> OTHER INFORMATION: FAM moiety
<220> FEATURE:
<221> NAME/KEY: modified_base
<222> LOCATION: (1)..(1)
<223> OTHER INFORMATION: CBP moiety
<220> FEATURE:
<221> NAME/KEY: modified_base
<222> LOCATION: (22)..(22)
<223> OTHER INFORMATION: BHQ1 moiety

<400> SEQUENCE: 8
ctccgtggcc ttagctgtgc tc                                             22

<210> SEQ ID NO 9
<211> LENGTH: 22
<212> TYPE: DNA
<213> ORGANISM: Artificial
<220> FEATURE:
<223> OTHER INFORMATION: Description of artificial sequence: Pf1-C-2
      Sequence
<220> FEATURE:
<221> NAME/KEY: modified_base
<222> LOCATION: (1)..(1)
<223> OTHER INFORMATION: FAM moiety
<220> FEATURE:
<221> NAME/KEY: modified_base
```

```
<222> LOCATION: (3)..(3)
<223> OTHER INFORMATION: CBP moiety
<220> FEATURE:
<221> NAME/KEY: modified_base
<222> LOCATION: (22)..(22)
<223> OTHER INFORMATION: BHQ1 moiety

<400> SEQUENCE: 9
ctccgtggcc ttagctgtgc tc                                              22

<210> SEQ ID NO 10
<211> LENGTH: 22
<212> TYPE: DNA
<213> ORGANISM: Artificial
<220> FEATURE:
<223> OTHER INFORMATION: Description of artificial sequence: Pf1-C-3
      Sequence
<220> FEATURE:
<221> NAME/KEY: modified_base
<222> LOCATION: (1)..(1)
<223> OTHER INFORMATION: FAM moiety
<220> FEATURE:
<221> NAME/KEY: modified_base
<222> LOCATION: (4)..(4)
<223> OTHER INFORMATION: CBP moiety
<220> FEATURE:
<221> NAME/KEY: modified_base
<222> LOCATION: (22)..(22)
<223> OTHER INFORMATION: BHQ1 moiety

<400> SEQUENCE: 10
ctccgtggcc ttagctgtgc tc                                              22

<210> SEQ ID NO 11
<211> LENGTH: 22
<212> TYPE: DNA
<213> ORGANISM: Artificial
<220> FEATURE:
<223> OTHER INFORMATION: Description of artificial sequence: Pf1-C-4
      Sequence
<220> FEATURE:
<221> NAME/KEY: modified_base
<222> LOCATION: (1)..(1)
<223> OTHER INFORMATION: FAM moiety
<220> FEATURE:
<221> NAME/KEY: modified_base
<222> LOCATION: (1)..(1)
<223> OTHER INFORMATION: CBP moiety
<220> FEATURE:
<221> NAME/KEY: modified_base
<222> LOCATION: (4)..(4)
<223> OTHER INFORMATION: CBP moiety
<220> FEATURE:
<221> NAME/KEY: modified_base
<222> LOCATION: (22)..(22)
<223> OTHER INFORMATION: BHQ1 moiety

<400> SEQUENCE: 11
ctccgtggcc ttagctgtgc tc                                              22

<210> SEQ ID NO 12
<211> LENGTH: 22
<212> TYPE: DNA
<213> ORGANISM: Artificial
<220> FEATURE:
<223> OTHER INFORMATION: Description of artificial sequence: Pf1-C-5
      Sequence
<220> FEATURE:
<221> NAME/KEY: modified_base
<222> LOCATION: (1)..(1)
<223> OTHER INFORMATION: FAM moiety
<220> FEATURE:
<221> NAME/KEY: modified_base
```

```
<222> LOCATION: (4)..(4)
<223> OTHER INFORMATION: CBP moiety
<220> FEATURE:
<221> NAME/KEY: modified_base
<222> LOCATION: (9)..(9)
<223> OTHER INFORMATION: CBP moiety
<220> FEATURE:
<221> NAME/KEY: modified_base
<222> LOCATION: (22)..(22)
<223> OTHER INFORMATION: BHQ1 moiety

<400> SEQUENCE: 12
ctccgtggcc ttagctgtgc tc                                              22

<210> SEQ ID NO 13
<211> LENGTH: 22
<212> TYPE: DNA
<213> ORGANISM: Artificial
<220> FEATURE:
<223> OTHER INFORMATION: Description of artificial sequence: Pf1-C-6
      Sequence
<220> FEATURE:
<221> NAME/KEY: modified_base
<222> LOCATION: (1)..(1)
<223> OTHER INFORMATION: FAM moiety
<220> FEATURE:
<221> NAME/KEY: modified_base
<222> LOCATION: (1)..(1)
<223> OTHER INFORMATION: CBP moiety
<220> FEATURE:
<221> NAME/KEY: modified_base
<222> LOCATION: (4)..(4)
<223> OTHER INFORMATION: CBP moiety
<220> FEATURE:
<221> NAME/KEY: modified_base
<222> LOCATION: (9)..(9)
<223> OTHER INFORMATION: CBP moiety
<220> FEATURE:
<221> NAME/KEY: modified_base
<222> LOCATION: (22)..(22)
<223> OTHER INFORMATION: BHQ1 moiety

<400> SEQUENCE: 13
ctccgtggcc ttagctgtgc tc                                              22

<210> SEQ ID NO 14
<211> LENGTH: 22
<212> TYPE: DNA
<213> ORGANISM: Artificial
<220> FEATURE:
<223> OTHER INFORMATION: Description of artificial sequence: Pf1-C-7
      Sequence
<220> FEATURE:
<221> NAME/KEY: modified_base
<222> LOCATION: (1)..(1)
<223> OTHER INFORMATION: FAM moiety
<220> FEATURE:
<221> NAME/KEY: modified_base
<222> LOCATION: (10)..(10)
<223> OTHER INFORMATION: CBP moiety
<220> FEATURE:
<221> NAME/KEY: modified_base
<222> LOCATION: (15)..(15)
<223> OTHER INFORMATION: CBP moiety
<220> FEATURE:
<221> NAME/KEY: modified_base
<222> LOCATION: (20)..(20)
<223> OTHER INFORMATION: CBP moiety
<220> FEATURE:
<221> NAME/KEY: modified_base
<222> LOCATION: (22)..(22)
<223> OTHER INFORMATION: BHQ1 moiety

<400> SEQUENCE: 14
```

```
ctccgtggcc ttagctgtgc tc                                          22
```

```
<210> SEQ ID NO 15
<211> LENGTH: 22
<212> TYPE: DNA
<213> ORGANISM: Artificial
<220> FEATURE:
<223> OTHER INFORMATION: Description of artificial sequence: Pf1-C-8
      Sequence
<220> FEATURE:
<221> NAME/KEY: modified_base
<222> LOCATION: (1)..(1)
<223> OTHER INFORMATION: FAM moiety
<220> FEATURE:
<221> NAME/KEY: modified_base
<222> LOCATION: (1)..(1)
<223> OTHER INFORMATION: CBP moiety
<220> FEATURE:
<221> NAME/KEY: modified_base
<222> LOCATION: (4)..(4)
<223> OTHER INFORMATION: CBP moiety
<220> FEATURE:
<221> NAME/KEY: modified_base
<222> LOCATION: (10)..(10)
<223> OTHER INFORMATION: CBP moiety
<220> FEATURE:
<221> NAME/KEY: modified_base
<222> LOCATION: (15)..(15)
<223> OTHER INFORMATION: CBP moiety
<220> FEATURE:
<221> NAME/KEY: modified_base
<222> LOCATION: (20)..(20)
<223> OTHER INFORMATION: CBP moiety
<220> FEATURE:
<221> NAME/KEY: modified_base
<222> LOCATION: (22)..(22)
<223> OTHER INFORMATION: BHQ1 moiety

<400> SEQUENCE: 15
ctccgtggcc ttagctgtgc tc                                          22

<210> SEQ ID NO 16
<211> LENGTH: 20
<212> TYPE: DNA
<213> ORGANISM: Artificial
<220> FEATURE:
<223> OTHER INFORMATION: Description of artificial sequence: P1F
      Sequence
<220> FEATURE:
<221> NAME/KEY: modified_base
<222> LOCATION: (19)..(19)
<223> OTHER INFORMATION: CBP moiety

<400> SEQUENCE: 16
aattcctgaa gctgacagca                                             20

<210> SEQ ID NO 17
<211> LENGTH: 17
<212> TYPE: DNA
<213> ORGANISM: Artificial
<220> FEATURE:
<223> OTHER INFORMATION: Description of artificial sequence: P1R
      Sequence
<220> FEATURE:
<221> NAME/KEY: modified_base
<222> LOCATION: (16)..(16)
<223> OTHER INFORMATION: CBP moiety
```

```
<400> SEQUENCE: 17
aaatagcctc caggcca                                                17

<210> SEQ ID NO 18
<211> LENGTH: 20
<212> TYPE: DNA
<213> ORGANISM: Artificial
<220> FEATURE:
<223> OTHER INFORMATION: Description of artificial sequence: P2F
      Sequence

<400> SEQUENCE: 18
aattcctgaa gctgacagca                                             20

<210> SEQ ID NO 19
<211> LENGTH: 17
<212> TYPE: DNA
<213> ORGANISM: Artificial
<220> FEATURE:
<223> OTHER INFORMATION: Description of artificial sequence: P2R
      Sequence

<400> SEQUENCE: 19
aaatagcctc caggcca                                                17

<210> SEQ ID NO 20
<211> LENGTH: 9
<212> TYPE: DNA
<213> ORGANISM: Artificial
<220> FEATURE:
<223> OTHER INFORMATION: Description of artificial sequence: C-PNA
      Sequence
<220> FEATURE:
<221> NAME/KEY: modified_base
<222> LOCATION: (6)..(6)
<223> OTHER INFORMATION: CBP moiety

<400> SEQUENCE: 20 cgatactgc                                                          9

<210> SEQ ID NO 21
<211> LENGTH: 9
<212> TYPE: DNA
<213> ORGANISM: Artificial
<220> FEATURE:
<223> OTHER INFORMATION: Description of artificial sequence: Control DNA
      Sequence

<400> SEQUENCE: 21 cgatactgc                                                          9

<210> SEQ ID NO 22
<211> LENGTH: 15
<212> TYPE: DNA
<213> ORGANISM: Artificial
<220> FEATURE:
<223> OTHER INFORMATION: Description of artificial sequence: Target DNA
      Sequence

<400> SEQUENCE: 22
tttgcagtat cgttt                                                  15
```